(12) United States Patent
Castaigne et al.

(10) Patent No.: US 8,921,314 B2
(45) Date of Patent: Dec. 30, 2014

(54) CONJUGATES OF GLP-1 AGONISTS AND USES THEREOF

(75) Inventors: Jean-Paul Castaigne, Mont-Royal (CA); Michel Demeule, Beaconsfield (CA); Catherine Gagnon, Montréal-Nord (CA); Betty Lawrence, Bolton (CA)

(73) Assignee: Angiochem, Inc., Montreal (CA)

( * ) Notice: Subject to any disclaimer, the term of this patent is extended or adjusted under 35 U.S.C. 154(b) by 0 days.

(21) Appl. No.: 13/124,013

(22) PCT Filed: Oct. 15, 2009

(86) PCT No.: PCT/CA2009/001476
§ 371 (c)(1),
(2), (4) Date: Sep. 22, 2011

(87) PCT Pub. No.: WO2010/043047
PCT Pub. Date: Apr. 22, 2010

(65) Prior Publication Data
US 2012/0015876 A1    Jan. 19, 2012

Related U.S. Application Data

(60) Provisional application No. 61/105,618, filed on Oct. 15, 2008.

(51) Int. Cl.
| | | |
|---|---|---|
| A61K 38/00 | (2006.01) | |
| A61P 3/10 | (2006.01) | |
| A61P 3/04 | (2006.01) | |
| C07K 14/605 | (2006.01) | |
| C07K 14/575 | (2006.01) | |
| A61K 47/48 | (2006.01) | |

(52) U.S. Cl.
CPC ....... *C07K 14/57563* (2013.01); *C07K 2319/01* (2013.01); *A61K 47/48338* (2013.01); *A61K 47/48246* (2013.01); *A61K 38/00* (2013.01)
USPC ................ 514/7.2; 514/4.9; 514/6.8; 514/6.9

(58) Field of Classification Search
None
See application file for complete search history.

(56) References Cited

U.S. PATENT DOCUMENTS

| | | |
|---|---|---|
| 4,671,958 A | 6/1987 | Rodwell et al. |
| 4,801,575 A | 1/1989 | Pardridge |
| 4,902,505 A | 2/1990 | Pardridge et al. |
| 4,942,184 A | 7/1990 | Haugwitz et al. |
| 5,028,697 A | 7/1991 | Johnson et al. |
| 5,041,424 A | 8/1991 | Saulnier et al. |
| 5,118,668 A | 6/1992 | Auerswald et al. |
| 5,126,249 A | 6/1992 | Becker et al. |
| 5,169,933 A | 12/1992 | Anderson et al. |
| 5,204,354 A | 4/1993 | Chakravarty et al. |
| 5,223,409 A | 6/1993 | Ladner et al. |
| 5,258,499 A | 11/1993 | Konigsberg et al. |
| 5,362,831 A | 11/1994 | Mongelli et al. |
| 5,442,043 A | 8/1995 | Fukuta et al. |
| 5,506,120 A | 4/1996 | Yamamoto et al. |
| 5,578,451 A | 11/1996 | Nishimoto |
| 5,627,270 A | 5/1997 | Kahne et al. |
| RE35,524 E | 6/1997 | Saulnier et al. |
| 5,683,694 A | 11/1997 | Bagshawe et al. |
| 5,780,265 A | 7/1998 | Dennis et al. |
| 5,807,980 A | 9/1998 | Lasters et al. |
| 5,869,045 A | 2/1999 | Hellstrom et al. |
| 5,908,832 A | 6/1999 | Payza et al. |
| 5,922,754 A | 7/1999 | Burchett et al. |
| 5,948,750 A | 9/1999 | Garsky et al. |
| 5,948,888 A | 9/1999 | de la Monte et al. |
| 5,955,444 A | 9/1999 | Ingram et al. |
| 5,962,266 A | 10/1999 | White et al. |
| 5,981,564 A | 11/1999 | Pagé et al. |
| 6,093,692 A | 7/2000 | Shen et al. |
| 6,126,965 A | 10/2000 | Kasid et al. |
| 6,191,290 B1 | 2/2001 | Safavy |
| 6,245,359 B1 | 6/2001 | Milstein et al. |
| 6,290,961 B1 | 9/2001 | Aoki et al. |
| 6,306,993 B1 | 10/2001 | Rothbard et al. |
| 6,310,039 B1 | 10/2001 | Kratz |
| 6,316,024 B1 | 11/2001 | Allen et al. |
| 6,348,207 B1 | 2/2002 | Milstein et al. |
| 6,372,250 B1 | 4/2002 | Pardridge |

(Continued)

FOREIGN PATENT DOCUMENTS

| | | |
|---|---|---|
| CA | 2283474 | 9/1998 |
| CA | 2421042 A1 | 5/2002 |

(Continued)

OTHER PUBLICATIONS

Ballabh et al., "The Blood-Brain Barrier: An Overview Structure, Regulation, and Clinical Implications," *Neurobiol Dis.* 16:1-13 (2004).
Boado, "Blood-brain Barrier Transport of Non-viral Gene and RNAi Therapeutics," *Pharm Res.* 24:1772-1787 (2007).
Bork et al., "Go Hunting in Sequence Databases But Watch Out for the Traps," *Trends Genet.* 12:425-427 (1996).
Brenner, "Errors in Genome Annotation," *Trends Genet.* 15:132-133 (1999).
Castex et al., "2-Pyrrolinodoxorubicin and Its Peptide-vectorized Form Bypass Multidrug Resistance," *Anticancer Drugs.* 15:609-617 (2004).

(Continued)

*Primary Examiner* — Gyan Chandra
(74) *Attorney, Agent, or Firm* — Clark & Elbing LLP; Kristina Bieker-Brady

(57) ABSTRACT

The present invention features a compound having the formula A-X-B, where A is peptide vector capable of enhancing transport of the compound across the blood-brain barrier or into particular cell types, X is a linker, and B is a GLP-1 agonist (e.g., exendin-4 or an exendin-4 analog). The compounds of the invention can be used to treat any disease where increased GLP-1 activity is desired, for example, metabolic diseases, such as obesity and diabetes.

8 Claims, 11 Drawing Sheets

(56) References Cited

U.S. PATENT DOCUMENTS

| | | |
|---|---|---|
| 6,376,648 B2 | 4/2002 | White et al. |
| 6,391,305 B1 | 5/2002 | Feng et al. |
| 6,391,913 B1 | 5/2002 | Page et al. |
| 6,469,047 B1 | 10/2002 | Jackson et al. |
| 6,475,481 B2 | 11/2002 | Talmadge |
| 6,475,781 B1 | 11/2002 | Mercola et al. |
| 6,495,513 B1 | 12/2002 | Rueger et al. |
| 6,613,890 B2 | 9/2003 | White et al. |
| 6,660,525 B2 | 12/2003 | Martin et al. |
| 6,689,582 B1 | 2/2004 | Davies et al. |
| 6,713,454 B1 | 3/2004 | Ekwuribe et al. |
| 6,906,033 B2 | 6/2005 | White et al. |
| 6,929,919 B2 | 8/2005 | St. George-Hyslop et al. |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,271,149 B2 | 9/2007 | Glaesner et al. |
| 7,319,090 B2 | 1/2008 | Katz |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Beliveau et al. |
| 8,530,429 B2 | 9/2013 | Robbins et al. |
| 8,569,323 B2 | 10/2013 | Ren et al. |
| 2002/0086384 A1 | 7/2002 | Levine et al. |
| 2002/0156124 A1 | 10/2002 | Gao et al. |
| 2003/0129186 A1 | 7/2003 | Beliveau et al. |
| 2003/0170891 A1 | 9/2003 | McSwiggen |
| 2003/0220391 A1 | 11/2003 | Bogardus et al. |
| 2004/0052814 A1 | 3/2004 | Shi et al. |
| 2004/0058865 A1 | 3/2004 | Danishefsky et al. |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 | 8/2004 | Harris et al. |
| 2004/0220132 A1 | 11/2004 | Kaemmerer |
| 2004/0241174 A1 | 12/2004 | Amphlett et al. |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0107325 A1 | 5/2005 | Manoharan et al. |
| 2005/0178395 A1 | 8/2005 | Hunter et al. |
| 2005/0183731 A1 | 8/2005 | Hunter et al. |
| 2006/0019347 A1* | 1/2006 | Cho et al. ............... 435/69.1 |
| 2006/0029609 A1 | 2/2006 | Zankel et al. |
| 2006/0135428 A1 | 6/2006 | Bridon et al. |
| 2006/0182684 A1 | 8/2006 | Beliveau |
| 2006/0189515 A1 | 8/2006 | Beliveau et al. |
| 2006/0251713 A1 | 11/2006 | Ben-Sasson et al. |
| 2007/0031844 A1 | 2/2007 | Khvorova et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1* | 9/2007 | Bridon et al. ............... 514/12 |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0021883 A1 | 1/2009 | Delida |
| 2009/0082277 A1 | 3/2009 | Beliveau et al. |
| 2009/0215883 A1 | 8/2009 | Bouzada et al. |
| 2009/0221477 A1 | 9/2009 | Artymiuk et al. |
| 2009/0246211 A1 | 10/2009 | Henri et al. |
| 2010/0209429 A1 | 8/2010 | Erlich et al. |
| 2010/0256055 A1 | 10/2010 | Castaigne et al. |
| 2010/0284921 A1 | 11/2010 | Gordon et al. |
| 2011/0039785 A1 | 2/2011 | Beliveau et al. |
| 2011/0059187 A1 | 3/2011 | Basu et al. |
| 2011/0171128 A1 | 7/2011 | Beliveau et al. |
| 2011/0218152 A1 | 9/2011 | Beliveau et al. |
| 2011/0305750 A1 | 12/2011 | Beliveau et al. |
| 2011/0318322 A1 | 12/2011 | Bossard |
| 2012/0015876 A1 | 1/2012 | Castaigne et al. |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034572 A1 | 2/2013 | Stanimirovic et al. |
| 2013/0035069 A1 | 2/2013 | Fisher |
| 2013/0045873 A1 | 2/2013 | Hood et al. |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |
| 2014/0017166 A1 | 1/2014 | Hettmann et al. |
| 2014/0086921 A1 | 3/2014 | Griswold-Prenner et al. |
| 2014/0099303 A1 | 4/2014 | Griswold-Prenner et al. |
| 2014/0099304 A1 | 4/2014 | Griswold-Prenner et al. |
| 2014/0100214 A1 | 4/2014 | Castro et al. |
| 2014/0120083 A1 | 5/2014 | Stern et al. |
| 2014/0127196 A1 | 5/2014 | Van Vlasselaer et al. |
| 2014/0127208 A1 | 5/2014 | Van Vlasselaer et al. |
| 2014/0140933 A1 | 5/2014 | Van Vlasselaer et al. |

FOREIGN PATENT DOCUMENTS

| | | |
|---|---|---|
| CA | 2525236 A1 | 1/2005 |
| CA | 2637893 | 7/2007 |
| CA | 2638034 | 7/2007 |
| CA | 2688344 A1 | 12/2008 |
| CN | 101160403 A | 4/2008 |
| CN | 101262890 A | 9/2008 |
| CN | 102406949 A | 4/2012 |
| CN | 102552928 A | 7/2012 |
| CN | 102614105 A | 8/2012 |
| DE | 19953696 | 5/2001 |
| EP | 0393431 | 10/1990 |
| EP | 0495049 B1 | 7/1992 |
| EP | 1466924 A1 | 10/2004 |
| EP | 1982699 A1 | 10/2008 |
| EP | 2333074 A1 | 6/2011 |
| EP | 2719708 A2 | 4/2014 |
| GB | 2360453 A | 9/2001 |
| JP | 2007-509977 A | 4/2007 |
| JP | 2008-529539 A | 8/2008 |
| JP | 2009-500431 A | 1/2009 |
| JP | 2011-144174 A | 7/2011 |
| RU | 2172323 C2 | 10/1999 |
| WO | WO 87/05702 | 9/1987 |
| WO | WO 96/31531 | 10/1996 |
| WO | WO 96/35788 | 11/1996 |
| WO | WO-96/39160 A1 | 12/1996 |
| WO | WO 96/39183 | 12/1996 |
| WO | WO 96/40210 | 12/1996 |
| WO | WO 97/33996 | 9/1997 |
| WO | WO-97/40160 A1 | 10/1997 |
| WO | WO 97/40854 | 11/1997 |
| WO | WO-99/46575 A2 | 9/1999 |
| WO | WO 00/01417 | 1/2000 |
| WO | WO 00/71574 | 11/2000 |
| WO | WO 01/30319 | 5/2001 |
| WO | WO-02/13873 A2 | 2/2002 |
| WO | WO 02/33090 | 4/2002 |
| WO | WO-02/43765 A2 | 6/2002 |
| WO | WO-02/085923 A2 | 10/2002 |
| WO | WO 03/009815 | 2/2003 |
| WO | WO-03/102583 A1 | 12/2003 |
| WO | WO 2004/060403 | 7/2004 |
| WO | WO 2004/091623 | 10/2004 |
| WO | WO-2004/093897 A1 | 11/2004 |
| WO | WO-2004/108071 A2 | 12/2004 |
| WO | WO 2005/002515 | 1/2005 |

(56) References Cited

FOREIGN PATENT DOCUMENTS

| | | |
|---|---|---|
| WO | WO-2005/014625 A1 | 2/2005 |
| WO | WO-2005/021579 A2 | 3/2005 |
| WO | WO-2005/042029 A2 | 5/2005 |
| WO | WO-2006/009902 A2 | 1/2006 |
| WO | WO 2006/086870 | 8/2006 |
| WO | WO-2006/089290 A1 | 8/2006 |
| WO | WO-2006/108052 A2 | 10/2006 |
| WO | WO-2006/138343 A2 | 12/2006 |
| WO | WO 2007/009229 | 1/2007 |
| WO | WO 2007/020085 | 2/2007 |
| WO | WO 2007/030619 | 3/2007 |
| WO | WO-2007/035716 A2 | 3/2007 |
| WO | WO-2007/044323 A2 | 4/2007 |
| WO | WO-2007/070672 A2 | 6/2007 |
| WO | WO-2007/082978 A1 | 7/2007 |
| WO | WO-2007/082979 A1 | 7/2007 |
| WO | WO 2007/103515 | 9/2007 |
| WO | WO 2007/113172 | 10/2007 |
| WO | WO 2008/012629 | 1/2008 |
| WO | WO-2008/012629 A2 | 1/2008 |
| WO | WO-2008/036682 A2 | 3/2008 |
| WO | WO 2008/046228 | 4/2008 |
| WO | WO 2008/069876 | 6/2008 |
| WO | WO-2008/116171 A1 | 9/2008 |
| WO | WO 2008/144919 | 12/2008 |
| WO | WO 2009/039188 | 3/2009 |
| WO | WO 2009/046220 | 4/2009 |
| WO | WO 2009/070597 | 6/2009 |
| WO | WO 2009/079790 | 7/2009 |
| WO | WO 2009/105671 | 8/2009 |
| WO | WO 2009/127072 | 10/2009 |
| WO | WO-2010/006239 A2 | 1/2010 |
| WO | WO-2010/043047 A1 | 4/2010 |
| WO | WO 2010/043049 | 4/2010 |
| WO | WO 2010/063122 | 6/2010 |
| WO | WO 2010/063123 | 6/2010 |
| WO | WO 2010/063124 | 6/2010 |
| WO | WO 2010/069074 | 6/2010 |
| WO | WO 2010/121379 | 10/2010 |
| WO | WO 2010/142035 | 12/2010 |
| WO | WO 2011/000095 | 1/2011 |
| WO | WO-2011/008823 A2 | 1/2011 |
| WO | WO 2011/041897 | 4/2011 |
| WO | WO-2011/063507 A1 | 6/2011 |
| WO | WO-2011/112635 A1 | 9/2011 |
| WO | WO 2011/153642 | 12/2011 |
| WO | WO 2012/000118 | 1/2012 |
| WO | WO-2012/006239 A1 | 1/2012 |
| WO | WO 2012/037687 | 3/2012 |
| WO | WO-2012/064973 A2 | 5/2012 |
| WO | WO-2012/068531 A2 | 5/2012 |
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/153286 A1 | 11/2012 |
| WO | WO-2012149267 A1 | 11/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013012918 A1 | 1/2013 |
| WO | WO-2013/023184 A1 | 2/2013 |
| WO | WO-2013/032591 A1 | 3/2013 |
| WO | WO-2013/043232 A2 | 3/2013 |
| WO | WO-2013/049332 A1 | 4/2013 |
| WO | WO-2013/056096 A1 | 4/2013 |
| WO | WO-2013/063468 A1 | 5/2013 |
| WO | WO-2013/071272 A1 | 5/2013 |
| WO | WO-2013/078562 A2 | 6/2013 |
| WO | WO-2013/078564 A2 | 6/2013 |
| WO | WO-2013/090861 A1 | 6/2013 |
| WO | WO-2013/120107 A1 | 8/2013 |
| WO | WO-2013/131032 A1 | 9/2013 |
| WO | WO-2013/151774 A1 | 10/2013 |
| WO | WO-2013/162757 A1 | 10/2013 |
| WO | WO-2013/185235 A1 | 12/2013 |
| WO | WO-2014/028487 A1 | 2/2014 |
| WO | WO-2014/028777 A2 | 2/2014 |
| WO | WO-2014026283 A1 | 2/2014 |
| WO | WO-2014026286 A1 | 2/2014 |
| WO | WO-2014071109 A1 | 5/2014 |
| WO | WO-2014071206 A1 | 5/2014 |
| WO | WO-2014071531 A1 | 5/2014 |
| WO | WO-2014076655 A1 | 5/2014 |
| WO | WO-2014082065 A1 | 5/2014 |
| WO | WO-2014082163 A1 | 6/2014 |
| WO | WO-2014082184 A1 | 6/2014 |

OTHER PUBLICATIONS

Coon et al., "Solutol HS 15, Nontoxic Polyoxyethylene Esters of 12-hydroxystearic Acid, Reverses Multidrug Resistance," *Cancer Res.* 51:897-902 (1991).

D'Onofrio et al., "Glycomimetics as Decorating Motifs for Oligonucleotides: Solid-phase Synthesis, Stability, and Hybridization Properties of Carbopeptoid-oligonucleotide Conjugates," *Bioconjug Chem.* 16:1299-1309 (2005).

Dagenais et al., "Development of an In Situ Mouse Brain Perfusion Model and Its Application to mdr1a P-glycoprotein-deficient Mice," *J Cereb Blood Flow Metab.* 20:381-386 (2000).

Deane et al., "LRP/Amyloid β-Peptide Interaction Mediates Differential Brain Efflux of Aβ Isoforms," *Neuron.* 43:333-344 (2004).

Dehouck et al., "A New Function for the LDL Receptor: Transcytosis of LDL Across the Blood-Brain Barrier," *J Cell Biol.* 138:877-889 (1997).

Dehouck et al., "An Easier, Reproducible, and Mass-production Method to Study the Blood-brain Barrier in Vitro," *J Neurochem.* 54:1798-1801 (1990).

Dehouck et al., "Drug Transfer Across the Blood-Brain Barrier: Correlation Between in Vitro and in Vivo Models," *J Neurochem.* 58:1790-1797 (1992).

Demeule et al., "High Transcytosis of Melanotransferrin (P97) Across the Blood-Brain Barrier," *J Neurochem.* 83:924-933 (2002).

Demeule et al., "Identification and Design of Peptides As a New Drug Delivery System for the Brain," *J Pharmacol Exp Ther.* 324:1064-1072 (2008).

Demeule et al., "Isolation of Endothelial Cells from Brain, Lung, and Kidney: Expression of the Multidrug Resistance P-Glycoprotein Isoforms," *Biochem Biophys Res Commun.* 281:827-834 (2001).

Doerks et al., "Protein Annotation: Detective Work for Function Prediction," *Trends Genet.* 14:248-250 (1998).

Fillebeen et al., "Receptor-Mediated Transcytosis of Lactoferrin Through the Blood-Brain Barrier," *J Biol Chem.* 274:7011-7017 (1999).

Fromm, "P-glycoprotein: A Defense Mechanism Limiting Oral Bioavailability and CNS Accumulation of Drugs," *Int J Clin Pharmacol Ther.* 38:69-74 (2000).

Gelmon, "The Taxoids: Paclitaxel and Docetaxel," *Lancet.* 344:1267-1272 (1994).

Gewirtz, "A Critical Evaluation of the Mechanisms of Action Proposed for the Antitumor Effects of the Anthracycline Antibiotics Adriamycin and Daunorubicin," *Biochem Pharmacol.* 57:727-741 (1999).

Grabb et al., "Neoplastic and Pharmacological Influence on the Permeability of an in vitro Blood-Brain Barrier," *J Neurosurg.* 82:1053-1058 (1995).

Guillot et al., "Angiotensin Peptide Regulation of Bovine Brain Microvessel Endothelial Cell Monolayer Permeability," *J Cardiovasc Pharmacol.* 18:212-218 (1991).

Gumbleton et al., "Progress and Limitations in the Use of in Vitro Cell Cultures to Serve as a Permeability Screen for the Blood-Brain Barrier," *J Pharm Sci.* 90:1681-1698 (2001).

Hawkins et al., "The Blood-Brain Barrier/Neurovascular Unit in Health and Disease," *Pharmacol Rev.* 57:173-185 (2005).

Hussain et al., "The Mammalian Low-Density Lipoprotein Receptor Family," *Annu Rev Nutr.* 19:141-172 (1999).

Ito et al., "Functional Characterization of the Brain-to-Blood Efflux Clearance of Human Amyloid-β Peptide (1-40) Across the Rat Blood-Brain Barrier," *Neurosci Res.* 56:246-252 (2006).

(56) References Cited

OTHER PUBLICATIONS

Ke et al., "Gene Delivery Targeted to the Brain Using an Angiopep-conjugated Polyethyleneglycol-modified Polyamidoamine Dendrimer," *Biomaterials.* 30:6976-6985 (2009).
Kiernan et al., "Fluorescent-Labelled Aprotinin: A New Reagent for the Histochemical Detection of Acid Mucosubstances," *Histochemie.* 34: 77-84 (1973).
Kobayashi et al., "The Protease Inhibitor Bikunin, a Novel Anti-Metastatic Agent," *Biol Chem.* 384:749-754 (2003).
Koo et al., "Differential Expression of Amyloid Precursor Protein mRNAs in Cases of Alzheimer's Disease and in Aged Nonhuman Primates," *Neuron.* 2:97-104 (1990).
Kounnas et al, "LDL Receptor-related Protein, a Multifunctional ApoE Receptor, Binds Secreted Beta-amyloid Precursor Protein and Mediates Its Degradation," *Cell.* 82:331-340 (1995).
Koziara et al., "In Situ Blood-brain Barrier Transport of Nanoparticles," *Pharm Res.* 20:1772-1778 (2003).
Kreuter et al., "Apolipoprotein-Mediated Transport of Nanoparticle-Bound Drugs Across the Blood-Brain Barrier," *J Drug Target.* 10:317-325 (2002).
Kreuter et al., "Direct Evidence that Polysorbate-80-coated Poly(Butylcyanoacrylate) Nanoparticles Deliver Drugs to the CNS Via Specific Mechanisms Requiring Prior Binding of Drug to the Nanoparticles," *Pharm Res.* 20:409-416 (2003).
Kreuter, "Nanoparticulate Carriers for Drug Delivery to the Brain," *Nanoparticles as Drug Carriers*, Torchilin VP, Imperial College Press, London pp. 527-547 (2006).
Laccabue et al., "A Novel Taxane Active against an Orthotopically Growing Human Glioma Xenograft," *Cancer.* 92:3085-3092 (2001).
Lai et al., "The Critical Component to Establish in vitro BBB Model: Pericyte," *Brain Res Rev.* 50:258-265 (2005).
Larionova et al., "Carbohydrate-Containing Derivatives of the Trypsin-Kallikrein Inhibitor Aprotinin from Bovine Organs II. Inhibitor Coupled to the (Carboxymethyl)dextran Derivatives of D-Galactose," *Biol Chem Hoppe-Seyler.* 366:743-748 (1985).
Larsson, "Megalin, an Endocytotic Receptor With Signalling Potential," *Acta Universitatis Upsaliensis Uppsala* 1-60 (2006).
Ma et al., "Cationic Charge-Dependent Hepatic Delivery of Amidated Serum Albumin," *J Control Release.* 102:583-594 (2005).
Marinò et al., "Megalin-Mediated Transcytosis of Thyroglobulin by Thyroid Cells is a Calmodulin-Dependent Process," *Thyroid.* 10:461-469 (2000).
Marinò et al., "Transcytosis of Retinol-Binding Protein Across Renal Proximal Tubule Cells After Megalin (gp 330)-Mediated Endocytosis," *J Am Soc Nephrol.* 12:637-648 (2001).
Martel et al., "Transport of Apolipoproteins E and J at the Blood-Brain Barrier Relevance to Alzheimer's disease," *S. T.P. Pharma Sciences:* 7:28-36 (1997).
Mazel et al., "Doxorubicin-peptide Conjugates Overcome Multidrug Resistance," *Anticancer Drugs.* 12:107-116 (2001).
McCarty, "Cell Biology of the Neurovascular Unit: Implications for Drug Delivery Across the Blood-Brain Barrier," *Assay Drug Dev Technol.* 3:89-95 (2005).
Moestrup et al., "Evidence that Epithelial Glycoprotein 330/Megalin Mediates Uptake of Polybasic Drugs," *J.Clin. Invest.* 96:1404-1413 (1995).
Moore et al., "The Role of Flexible Tethers in Multiple Ligand-receptor Bond Formation Between Curved Surfaces," *Biophys J.* 91:1675-1687 (2006).
Muratovska et al., "Conjugate for Efficient Delivery of Short Interfering RNA (siRNA) Into Mammalian Cells," *FEBS Lett.* 558:63-68 (2004).
Ngo et al., "Computational Complexity; Protein Structure Prediction, and the Levinthal Paradox," *The Protein Folding Problem and Tertiary Structure Prediction* Merz, Jr. and Le Grand, Eds. 491-495 (1994).
Niola et al., "A Plasmid-encoded VEGF siRNA Reduces Glioblastoma Angiogenesis and Its Combination with Interleukin-4 Blocks Tumor Growth in a Xenograft Mouse Model," *Cancer Biol Ther.* 5:174-179 (2006).
Orlando et al., "Identification of the Second Cluster of Ligand-Binding Repeats in Megalin as a Site for Receptor-Ligand Interactions," *Proc Natl Acad Sci.* 94:2368-2373 (1997).
Pan et al., "Efficient Transfer of Receptor-Associated Protein (RAP) Across the Blood-Brain Barrier," *J Cell Sci.* 117:5071-5078 (2004).
Pardridge, "Blood-Brain Barrier Biology and Methodology," *J Neurovirol.* 5:556-569 (1999).
Pardridge, "CNS Drug Design Based on Principles of Blood-Brain Barrier Transport," *J Neurochem.* 70:1781-1792 (1998).
Pardridge, "Drug Targeting to the Brain," *Pharm Res.* 24:1733-1744 (2007).
Peri et al., "D-Glucose as a Regioselectively Addressable Scaffold for Combinatorial Chemistry on Solid Phase," *J Carbohydr Chem.* 22:57-71 (2003).
Prince et al., "Lipoprotein Receptor Binding, Cellular Uptake, and Lysosomal Delivery of Fusions Between the Receptor-Associated protein (RAP) and α-L-Iduronidase or Acid α-Glucosidase," *J Biol Chem.* 279:35037-35046 (2004).
Qu et al., "Carbohydrate-based Micelle Clusters Which Enhance Hydrophobic Drug Bioavailability by Up to 1 Order of Magnitude," *Biomacromolecules.* 7:3452-3459 (2006).
Ramakrishnan, "The Role of P-glycoprotein in the Blood-Brain Barrier," *Einstein Q J Biol Med.* 19:160-165 (2003).
Rawat et al., "Lipid Carriers: A Versatile Delivery Vehicle for Proteins and Peptides," *Yakugaku Zasshi.* 128:269-280 (2008).
Régina et al., "Antitumour Activity of ANG1005, a Conjugate Between Paclitaxel and the New Brain Delivery Vector Angiopep-2," *Br J Pharmacol.* 155:185-197 (2008).
Régina et al., "Differences in Multidrug Resistance Phenotype and Matrix Metalloproteinases Activity Between Endothelial Cells from Normal Brain and Glioma," *J Neurochem.* 84:316-324 (2003).
Scherrmann, "Drug Delivery to Brain Via the Blood-Brain Barrier," *Vascul Pharmacol.* 38:349-354 (2002).
Schinkel, "P-Glycoprotein, A Gatekeeper in the Blood-Brain Barrier," *Adv Drug Deliv Rev.* 36:179-194 (1999).
Seidel et al., "Effects of Trasylol on the Blood-Brain Barrier in Rats," *Naunyn Schmiedebergs Arch Pharmacol.* 284:R73 (1974).
Shibata et al., "Clearance of Alzheimer's Amyloid-$\beta_{1-40}$ Peptide From Brain by LDL Receptor-Related Protein-1 at the Blood-Brain Barrier," *J Clin Invest.* 106:1489-1499 (2000).
Shiiki et al., "Brain Insulin Impairs Amyloid-β(1-40) Clearance From the Brain," *J Neurosci.* 24:9632-9637 (2004).
Shimura et al., "Transport Mechanism of a New Behaviorally Highly Potent Adrenocorticotropic Hormone (ACTH) Analog, Ebiratide, through the Blood-Brain Barrier," *J Pharmacol Exp Ther.* 258:459-465 (1991).
Skolnick et al., "From Genes to Protein Structure and Function: Novel Applications of Computational Approaches in the Genomic Era," *Trends Biotechnol.* 18:34-39 (2000).
Smith, "Brain Perfusion Systems for Studies of Drug Uptake and Metabolism in the Central Nervous System," *Pharm Biotechnol.* 285-307 (1996).
Smith et al., "The Challenges of Genome Sequence Annotation or 'The Devil is in the Details'," *Nat Biotechnol.* 15:1222-1223 (1997).
Steiniger et al., "Chemotherapy of Glioblastoma in Rats Using Doxorubicin-loaded Nanoparticles," *Int J Cancer.* 109:759-767 (2004).
Tamai et al., "Structure-Internalization Relationship for Adsorptive-Mediated Endocytosis of Basic Peptides at the Blood-Brain Barrier," *J Pharmacol Exp Ther.* 280:410-415 (1997).
Temsamani et al., "Vector-Mediated Drug Delivery to the Brain," *Expert Opin Biol Ther.* 1:773-782 (2001).
Terasaki et al., "New Approaches to in vitro Models of Blood-Brain Barrier Drug Transport," *Drug Discov Today.* 8:944-954 (2003).
Triguero et al., "Capillary Depletion Method for Quantification of Blood-Brain Barrier Transport of Circulating Peptides and Plasma Proteins," *J Neurochem.* 54:1882-1888 (1990).
Turner et al., "RNA Targeting With Peptide Conjugates of Oligonucleotides, siRNA and PNA," *Blood Cells Mol Dis.* 38:1-7 (2007).
Veronese et al., "PEGylation, Successful Approach to Drug Delivery," *Drug Discov Today.* 10:1451-1458 (2005).

(56) References Cited

OTHER PUBLICATIONS

Wang et al., "DNA/dendrimer Complexes Mediate Gene Transfer into Murine Cardiac Transplants ex Vivo," *Mol Ther.* 2:602-608 (2000).
Wells, "Additivity of Mutational Effects in Proteins," *Biochemistry.* 29:8509-8517 (1990).
Witt et al., "Peptide Drug Modifications to Enhance Bioavailability and Blood-Brain Barrier Permeability," *Peptides.* 22:2329-2343 (2001).
Xu et al., "In Vitro and in Vivo Evaluation of Actively Targetable Nanoparticles for Paclitaxel Delivery," *Int J Pharm.* 288:361-368 (2005).
Yepes et al., "Tissue-Type Plasminogen Activator Induces Opening of the Blood-Brain Barrier Via the LDL Receptor-Related Protein," *J Clin Invest.* 112:1533-1540 (2003).
Zhang et al., "Intravenous RNA Interference Gene Therapy Targeting the Human Epidermal Growth Factor Receptor Prolongs Survival in Intracranial Brain Cancer," *Clin Cancer Res.* 10:3667-3677 (2004).
Zhang et al., "Silencing the Epidermal Growth Factor Receptor Gene with RNAi may be Developed as a Potential Therapy for Non Small Cell Lung Cancer," *Genet Vaccines Ther.* 3:5 (2005).
Zhang et al., "siRNA-containing Liposomes Modified with Polyarginine Effectively Silence the Targeted Gene," *J Control Release.* 112:229-239 (2006).
Zlokovic et al., "Glycoprotein 330/Megalin: Probable Role in Receptor-mediated Transport of Apolipoprotein J Alone and in a Complex With Alzheimer Disease Amyloid β at the Blood-Brain and Blood-Cerebrospinal Fluid Barriers," *Proc Natl Acad Sci USA.* 93:4229-4234 (1996).
U.S. Appl. No. 12/601,803, filed Nov. 24, 2009, Beliveau et al.
U.S. Appl. No. 12/632,557, filed Dec. 7, 2009, Castaigne et al.
Arpicco et al., "New Coupling Reagents for the Preparation of Disulfide Cross-Linked Conjugates with Increased Stability," *Bioconjugate Chem.* 8:327-337 (1997).
Banks, "Leptin Transport Across the Blood-Brain Barrier: Implications for the Cause and Treatment of Obesity," *Curr. Pharm. Des.* 7:125-133 (2001).
Banks, "The Blood-Brain Barrier as a Cause of Obesity," *Curr. Pharm. Des.* 14:1606-1614 (2008).
Bicamumpaka et al., "In Vitro Cytotoxicity of Paclitaxel-Transferrin Conjugate on H69 Cells," *Oncol. Rep.* 5:1381-1383 (1998).
Demeule et al., "Drug Transport to the Brain: Key Roles for the Efflux Pump P-Glycoprotein in the Blood-Brain Barrier," *Vascul. Pharmacol.* 38:339-348 (2002).
Dooley et al., "An All D-amino Acid Opioid Peptide with Central Analgesic Activity from a Combinatorial Library," *Science* 266:2019-2022 (1994).
Eigenbrot et al., "X-Ray Structure of Glial Cell-Derived Neurotrophic Factor at 1.9 Å Resolution and Implications for Receptor Binding," *Nat. Struct. Biol.* 4:435-438 (1997).
Gabius et al., "Targeting of Neoglycoprotein-Drug Conjugates to Cultured Human Embryonal Carcinoma Cells,"*J. Cancer Res. Clin. Oncol.* 113:126-130 (1987).
Gottschalk et al., "Protein Self-Association in Solution: The Bovine Pancreatic Trypsin Inhibitor Decamer," *Biophys. J.* 84: 3941-3958 (2003).
Harkavyi et al., "Glucagon-Like Peptide 1 Receptor Stimulation Reverses Key Deficits in Distinct Rodent Models of Parkinson's Disease," *J. Neuroinflammation.* 5:19(2008) (pp. 1-9).
Kalra, "Central Leptin Insufficiency Syndrome: An Interactive Etiology for Obesity, Metabolic and Neural Diseases and for Designing New Therapeutic Interventions," *Peptides* 29:127-138 (2008).
Karyekar et al., "Zonula Occludens Toxin Increases the Permeability of Molecular Weight Markers and Chemotherapeutic Agents Across the Bovine Brain Microvessel Endothelial Cells," *J. Pharm. Sci.* 92:414-423 (2003).
Kirsch et al., "Anti-Angiogenic Treatment Strategies for Malignant Brain Tumors," *J. Neurooncol.* 50:149-163 (2000).
Lewis et al., "Maleimidocysteineamido-DOTA Derivatives: New Reagents for Radiometal Chelate Conjugation to Antibody Sulfhydryl Groups Undergo pH-Dependent Cleavage Reactions," *Bioconjugate Chem.* 9:72-86 (1998).
Saito et al., "Drug Delivery Strategy Utilizing Conjugation Via Reversible Disulfide Linkages: Role and Site of Cellular Reducing Activities," *Adv. Drug. Deliv. Rev.* 55:199-215 (2003).
Samson et al., "Gene Therapy for Diabetes: Metabolic Effects of Helper-Dependent Adenoviral Exendin 4 Expression in a Diet-Induced Obesity Mouse Model," *Mol. Ther.* 16:1805-1812 (2008) (pp. 1-18).
Uekita et al., "Cytoplasmic Tail-Dependent Internalization of Membrane-Type 1 Matrix Metalloproteinase is Important for its Invasion-Promoting Activity," *J. Cell. Biol.* 155:1345-1356 (2001).
Uekita et al., "Membrane-Type 1 Matrix Metalloproteinase Cytoplasmic Tail-Binding Protein-1 is a New Member of the Cupin Superfamily. A Possible Multifunctional Protein Acting as an Invasion Suppressor Down-Regulated in Tumors," *J. Biol. Chem.* 279:12734-12743 (2004).
Akhtar et al., "Nonviral Delivery of Synthetic siRNAs in Vivo," *J. Clin. Invest.* 117: 3623-3632 (2007).
Anonymous, "Blood-Brain Barrier Tackled," <http:www.ecancermedicalscience.com/news-insider-news.asp?itemId=326> Oct. 22, 2008.
Bertrand et al., "Transport Characteristics of a Novel Peptide Platform for CNS Therapeutics," *J. Cell Mol. Med.* published online Oct. 10, 2009.
Boules et al., "Bioactive Analogs of Neurotensin: Focus on CNS Effects," *Peptides* 27: 2523-2533 (2006).
Chari, "Targeted Cancer Therapy: Conferring Specificity to Cytotoxic Drugs," *Acc. Chem. Res.* 41:98-107 (2008).
Ché et al., "New Angiopep-Modified Doxorubicin (ANG1007) and Etoposide (ANG1009) Chemotherapeutics with Increased Brain Penetration," *J. Med. Chem.* 53: 2814-2824 (2010).
Demeule et al., "Involvement of the Low-Density Lippprotein Receptor-Related Protein in the Transcytosis of the Brain Delivery Vector Angiopep-2," *J. Neurochem.* 106: 1534-1544 (2008).
Garsky et al., "The Synthesis of a Prodrug of Doxorubicin Designed to Provide Reduced Systemic Toxicity and Greater Target Efficacy," *J. Med. Chem.* 44: 4216-4224 (2001).
Huang et al., "Targeting Delivery of Paclitaxel into Tumor Cells via Somatostatin Receptor Endocytosis," *Chem. Biol.* 7: 453-461 (2000).
Kilic et al., "Intravenous TAT-GDNF is Protective after Focal Cerebral Ischemia in Mice," *Stroke* 34: 1304-1310 (2003).
Kumar et al., "Transvascular Delivery of Small Interfering RNA to the Central Nervous System," *Nature* 448: 39-43 (2007).
Rouselle et al., "New Advances in the Transport of Doxorubicin through the Blood-Brain Barrier by a Peptide Vector-Mediated Strategy," *Mol. Pharmacol.* 57: 679-686 (2000).
Takei et al., "A Small Interfering RNA Targeting Vascular Endothelial Growth Factor as Cancer Therapeutics," *Cancer Res.* 64: 3365-3370 (2004).
Trail et al., "Cure of Xenografted Human Carcinomas by BR96-Doxorubicin Immunoconjugates," *Science* 261:212-215 (1993).
U.S. Appl. No. 61/546,851, filed Oct. 13, 2011, Demeule et al.
Grimm et al., "Ten Year Biochemical Outcomes Following 125-Iodine Monotherapy for Early Stage Prostate Cancer." *Int. J. Rad. Oncol. Biol. Phys.* 48:146-147 (2000).
Kurzrock et al., "ANGI005: Results of a Phase I study in patients with advanced solid tumors and metastatic brain cancer" Poster B168, ACCR/NCI/EORTC Annual Meeting, 2009.
Mathupala, "Delivery of Small-interfering RNA (siRNA) to the Brain," *Exp. Opin. Ther. Pat.* 19: 137-140, (2009).
Nyalendo et al., "Impaired Tyrosine Phosphorylation of Membrane type 1-Matrix Metalloproteinase Reduces Tumor Cell Proliferation in Three-Dimensional Matrices and Abrogates Tumor Growth in Mice," *Carcinogenesis* 29:1655-1664, (2008).
Sadeghi-aliabadi et al., "Solvent optimization on Taxol extraction from *Taxus baccata* L., using HPLC and LC-MS," *DARU* 17:192-198, (2009).
Schiff and Horwitz, "Taxol Stabilizes Microtubules in Mouse Fibroblast Cells," *Proc Natl Acad Sci USA* 77:1561-1565, (1980).
Tilstra et al., "Protein Transduction: Identification, Characterization and Optimization," *Biochem. Soc. Trans.* 35:811-815, (2007).

(56) References Cited

OTHER PUBLICATIONS

Zhang et al., "Tat-modified Leptin is more Accessible to Hypothalamus Through Brain-blood Barrier with a Significant Inhibition of Body-weight Gain in High-fat-diet Fed Mice," *Exp. Clin. Endocrin. Diabet.* 118:31-37 (2010).
International Search Report and Written Opinion of the International Searching Authority for Application No. PCT/CA2009/001476, dated Jan. 26, 2010.
U.S. Appl. No. 61/138,375, Beliveau et al.
Author manuscript of Howes et al., "Rapid induction of therapeutic hypothermia using convective-immersion surface cooling: Safety, efficacy and outcomes," published in final edited form as: Resuscitation. 81(4):388-392 (2010); (13 pages).
Belkin et al., "Matrix-dependent proteolysis of surface transglutaminase by membrane-type metalloproteinase regulates cancer cell adhesion and locomotion," J Biol Chem. 276(21):18415-18422 (2001).
Bickel et al., "Delivery of peptides and proteins through the blood-brain barrier," Adv Drug Deliv Rev. 46:247-279 (2001).
Boado et al., "GDNF fusion protein for targeted-drug delivery across the human blood-brain barrier," Biotechnol Bioeng. 100(2):387-96 (2008).
Bork, "Powers and pitfalls in sequence analysis: the 70% hurdle," Genome Res. 10:398-400 (2000).
Brady et al., "Drug design. Refelections on a peptide." Nature. 368(6473):692-693 (1994).
Buvanendran et al., "Recent advances in nonopioid analgesics for acute pain management," Tech Reg Anesth Pain Man. 11(1):19-26 (2007).
Carell et al., "A novel procedure for the synthesis of libraries containing small organic molecules," Angew Chem Int Ed Engl. 33(20):2059-2061 (1994).
Carell et al., "A solution-phase screening procedure for the isolation of active compounds from a library of molecules," Angew Chem Int Ed Engl. 33(20):2061-2064 (1994).
Chen et al., "Synthesis of doxorubicin conjugates through hydrazone bonds to melanotransferrin P97," Synth Commun. 33(14):2377-2390 (2003).
Cho et al., "An unnatural biopolymer," Science. 261:1303-1305 (1993).
Chu et al., "Detection of soluble P-glycoprotein in culture media and extracellular fluids," Biochem Biophys Res Commun. 203(1):506-512 (1994).
Cui et al., "PAMAM-drug complex for delivering anticancer drug across blood-brain barrier in-vitro and in-vivo," Afr J Pharm Pharmacol. 3(5):227-233 (2009).
Cull et al., "Screening for receptor ligands using large libraries of peptides linked to the C terminus of the lac repressor," Proc Natl Acad Sci U S A. 89(5): 1865-1869 (1992).
D'Ortho et al., "Membrane-type matrix metalloproteinases 1 and 2 exhibit broad-spectrum proteolytic capacities comparable to many matrix metalloproteinases," Eur J Biochem. 250(3): 751-757 (1997).
Demeule et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
DeWitt et al., "'Diversomers': an approach to nonpeptide, nonoligomeric chemical diversity," Proc Natl Acad Sci U S A. 90(15):6909-6913 (1993).
Erb et al., "Recursive deconvolution of combinatorial chemical libraries," Proc Natl Acad Sci U S A. 91(24):11422-11426 (1994).
Evans et al., "Design of nonpeptidal ligands for a peptide receptor: Cholecystokinin antagonists," J Med Chem. 30(7):1229-1239 (1987).
Extended European Search Report for International Application No. PCT/CA2009001476, dated Mar. 22, 2013 (11 pages).
Fauchere et al., "Association with HeLa cells of *Campylobacter jejuni* and *Campylobacter coli* isolated from human feces," Infect Immun. 54(2):283-287 (1986).
Fioretti et al., "Aprotinin-like isoinhibitors in bovine organs," Biol Chem Hoppe Seyler. 369 Suppl:37-42 (1988).
Fodor et al., "Multiplexed biochemical assays with biological chips," Nature. 364(6437):555-556 (1993).
Furuta et al., "Structure-antinociceptive activity studies with neurotensin," Br J Pharmacol. 83(1):43-48 (1984).
Gabathuler, "Approaches to transport therapeutic drugs across the blood-brain barrier to treat brain diseases," Neurobiol Dis. 37(1):48-57 (2010).
Gallop et al., "Applications of combinatorial technologies to drug discovery. 1. Background and peptide combinatorial libraries," J Med Chem. 37(9):1233-1251 (1994).
Halab et al., "Design, synthesis, and conformational analysis of azacycloalkane amino acids as conformationally constrained probes for mimicry of peptide secondary structures," Biopolymers. 55(2):101-122 (2000).
Hanessian et al., "Synthesis of (4$S$)-hydroxymethyl-(2$R$)-(2-propyl)-butyrolactone: A quest for a practical route to an important hydroxyethylene isostere chiron," Tetrahedron. 53(18):6281-6294 (1997).
Hein et al., "Click chemistry, a powerful tool for pharmaceutical sciences," Pharm Res. 25(10):2216-2230 (2008).
Hijova, Matrix metalloproteinases: their biological functions and clinical implications, Bratisl Lek Listy. 106(3):127-132 (2005).
Hiraoka et al., "Matrix metalloproteinases regulate neovascularization by acting as pericellular fibrinolysins," Cell. 95(3):365-377 (1998).
Hong et al., "Coexpression of cyclooxygenase-2 and matrix metalloproteinases in human aortic atherosclerotic lesions," Yonsei Med J. 41(1):82-88 (2000).
Hotary et al., "Membrane type I matrix metalloproteinase usurps tumor growth control imposed by the three-dimensional extracellular matrix," Cell. 114(1):33-45 (2003).
Huang et al., "Production of bioactive human beta-defensin 5 and 6 in *Escherichia coli* by soluble fusion expression," Protein Expr Purif. 61(2):168-174 (2008).
Hudson et al., "Methionine enkephalin and isosteric analogues. I. Synthesis on a phenolic resin support," Int J Pept Protein Res. 14(3):177-185 (1979).
Imai et al., "Expression of membrane-type 1 matrix metalloproteinase and activation of progelatinase A in human osteoarthritic cartilage," Am J Pathol. 151(1):245-256 (1997).
Itoh et al., "MT1-MMP: a potent modifier of pericellular microenvironment," J Cell Physiol. 206(1):1-8 (2006).
Jameson et al., "A rationally designed CD4 analogue inhibits experimental allergic encephalomyelitis," Nature. 368(6473):744-746 (1994).
Kajita et al., "Membrane-type 1 matrix metalloproteinase cleaves CD44 and promotes cell migration" J Cell Biol. 153(5):893-904 (2001).
Kamps et al., "Uptake of long-circulating immunoliposomes, directed against colon adenocarcinoma cells, by liver metastases of colon cancer," J Drug Target. 8(4):235-245 (2000).
Kesari et al., "Phase II study of temozolomide, thalidomide, and celecoxib for newly diagnosed glioblastoma in adults," Neuro Oncol. 10(3):300-308 (2008).
Kirpotin et al., "Sterically stabilized anti-HER2 immunoliposomes: design and targeting to human breast cancer cells in vitro," Biochemistry. 36(1):66-75 (1997).
Konttinen et al., "Analysis of 16 different matrix metalloproteinases (MMP-1 to MMP-20) in the synovial membrane: different profiles in trauma and rheumatoid arthritis" Ann Rheum Dis. 58(11):691-7 (1999).
Kurzrock et al., "ANG1005, an Angiopep-2/paclitaxel conjugate: The first clinical trial in patients with advanced cancer and brain metastases: Preliminary safety and tolerability data," 20th EORTC-NCI-AACR Symposium on "Molecular Targets and Cancer Therapeutics", Euro J of Cancer. 6(12):133, Abstract 424 (2008).
Lachowicz et al., "Analgesic properties of a novel brain-penetrant Angiopep-2-neurotensin derivative (ANG2002) for treating chronic pain," Program No. 173.28/AA9 2012 Neuroscience Meeting Planner, New Orleans, LA: Society for Neuroscience (2012).

(56) References Cited

OTHER PUBLICATIONS

Lam et al., A new type of synthetic peptide library for identifying ligand-binding activity, Nature. 354(6348):82-4 (1991).
Lam, "Application of combinatorial library methods in cancer research and drug discovery," Anticancer Drug Des. 12(3):145-67 (1997).
Langer, "New methods of drug delivery," Science. 249(4976):1527-33 (1990).
Mamot et al., "Epidermal growth factor receptor (EGFR)-targeted immunoliposomes mediate specific and efficient drug delivery to EGFR- and EGFRvIII-overexpressing tumor cells," Cancer Res. 63(12):3154-61 (2003).
Markman et al., "Phase II trial of weekly single-agent paclitaxel in platinum/paclitaxel-refractory ovarian cancer," J Clin Oncol. 20(9):2365-9 (2002).
Martinez-Fong et al., "Neurotensin-SPDP-poly-L-lysine conjugate: a nonviral vector for targeted gene delivery to neural cells," Molecular Brain Research 69:249-262 (1999).
Michaud et al., "Risks and benefits of taxanes in breast and ovarian cancer," Drug Saf. 23(5):401-28 (2000).
Moase et al., "Anti-MUC-1 immunoliposomal doxorubicin in the treatment of murine models of metastatic breast cancer," Biochim Biophys Acta. 1510(1-2):43-55 (2001).
Nakada et al., "Expression and tissue localization of membrane-type 1, 2, and 3 matrix metalloproteinases in human astrocytic tumors," Am J Pathol. 154(2):417-28 (1999).
Nam et al., "Sterically stabilized anti-G(M3), anti-Le(x) immunoliposomes: targeting to B16BL6, HRT-18 cancer cells," Oncol Res. 11(1):9-16 (1999).
Nyalendo et al., "Src-dependent phosphorylation of membrane type I matrix metalloproteinase on cytoplasmic tyrosine 573: role in endothelial and tumor cell migration," J Biol Chem. 282(21):15690-9 (2007).
Office Action and its English translation for Chinese Patent Application No. 200980150216.3, mailed Dec. 18, 2013 (14 pages).
Pardridge et al. "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pardridge et al., "Selective transport of an anti-transferrin receptor antibody through the blood-brain barrier in vivo," J Pharmacol Exp Ther. 259(1):66-70 (1991).
Pardridge, "Vector-mediated drug delivery to the brain," Adv Drug Deliv Rev. 36(2-3):299-321 (1999).
Park et al., "Development of anti-p185HER2 immunoliposomes for cancer therapy," Proc Natl Acad Sci U S A. 92(5):1327-31 (1995).
Park et al., "Recombinant expression of biologically active rat leptin in *Escherichia coli*," Protein Expr Purif. 22(1):60-69 (2001).
Pathan et al. "CNS drug delivery systems: novel approaches," Recent Pat Drug Deliv Formul. 3(1):71-89 (2009).
Pei et al., "Transmembrane-deletion mutants of the membrane-type matrix metalloproteinase-1 process progelatinase A and express intrinsic matrix-degrading activity," J Biol Chem. 271(15):9135-9140 (1996).
Powell et al., "Peptide stability in drug development. II. Effect of single amino acid substitution and glycosylation on peptide reactivity in human serum," Pharm Res. 10(9):1268-73 (1993).
Rajavashisth et al., "Membrane type 1 matrix metalloproteinase expression in human atherosclerotic plaques: evidence for activation by proinflammatory mediators," Circulation. 99(24):3103-9 (1999).
Rizo et al. "Constrained peptides: models of bioactive peptides and protein substructures," Annu Rev Biochem. 61:387-418 (1992).
Rose et al., "Metastatic patterns in histologic variants of ovarian cancer. An autopsy study," Cancer. 64(7):1508-13 (1989).
Rudikoff et al., "Single amino acid substitution altering antigen-binding specificity," Proc Natl Acad Sci USA. 79:1979-83 (1982).
Sabeh et al. "Tumor cell traffic through the extracellular matrix is controlled by the membrane-anchored collagenase MT1-MMP," J Cell Biol. 167(4):769-81 (2004).

Sahm et al. "Receptor binding affinities and biological activities of linear and cyclic melanocortins in B16 murine melanoma cells expressing the native MC1 receptor," J Pharm Pharmacol. 48(2):197-200 (1996).
Scott et al. "Searching for peptide ligands with an epitope library," Science. 249(4967):386-90 (1990).
Seiden et al., "A phase II study of the MDR inhibitor biricodar (INCEL, VX-710) and paclitaxel in women with advanced ovarian cancer refractory to paclitaxel therapy," Gynecol Oncol. 86(3):302-10 (2002).
Shao et al., "Angiopep-2 modified PE-PEG based polymeric micelles for amphotericin B delivery targeted to the brain," J Control Release. 147(1):118-26 (2010).
Spatola et al., "Structure-activity relationships of enkephalins containing serially replaced thiomethylene amide bond surrogates," Life Sci. 38(14):1243-9 (1986).
Svenson et al., "Dendrimers in biomedical applications—reflections on the field," Adv Drug Deliv Rev. 57(15):2106-2129 (2005).
UniProt Consortium, "P08183 (MDR1_HUMAN)," <http://www.uniprot.org/uniprot/P08183>, retrieved on Sep. 18, 2013 (16 pages).
Vincent, "Neurotensin receptors: binding properties, transduction pathways, and structure," Cell Mol Neurobiol. 15(5):501-512 (1995).
Wang et al., "Polyamidoamine dendrimers with a modified Pentaerythritol core having high efficiency and low cytotoxicity as gene carriers," Biomacromolecules. 10(3):617-622 (2009).
Wang et al., "Synthesis and antinociceptive effects of endomorphin-1 analogs with C-terminal linked by oligoarginine," Peptides. 32(2):293-9 (2011).
Williamson et al., "Expression and purification of recombinant neurotensin in *Escherichia coli*," Protein Expr Purif. 19(2):271-5 (2000).
Yano et al., "Simultaneous activation of two different receptor systems by enkephalin/neurotensin conjugates having spacer chains of various lengths," Eur J Pharm Sci. 7:41-48 (1998).
Zhai et al. "Expression of membrane type 1 matrix metalloproteinase is associated with cervical carcinoma progression and invasion," Cancer Res. 65(15):6543-6550 (2005).
Zhang et al. "In vitro gene delivery using polyamidoamine dendrimers with a trimesyl core," Biomacromolecules. 6(1):341-350 (2005).
American College of Rheumatology Subcommittee on Rheumatoid Arthritis Guidelines, "Guidelines for the management of rheumatoid arthritis: 2002 update," Arthritis & Rheum, 46(2):328-46 (2002).
Barakat et al., "Modulation of p-glycoprotein function by caveolin-1 phosphorylation," J Neurochem. 101(1):1-8 (2007).
Becker, "Putative antigenic domains in glycoprotein G of rabies virus: is the RGK sequence involved in virus adsorption to cellular receptors?," Virus Genes. 3(3):277-84 (1990).
Castaigne et al., "425 POSTER ANG1005: Preliminary clinical safety and tolerability in patients with recurrent malignant glioma," Eur J Cancer. 6(12):133-134 (2008).
Chu et al., "H NMR spectra of diastereomeric aromatic dipeptides (Phe—Phe) in aqueous solution," Magn Reson Chem. 23(6):450-3 (1985).
Comereski et al., "BR96-doxorubicin conjugate (BMS-182248) versus doxorubicin: a comparative toxicity assessment in rats," Toxicol Pathol. 22(5):473-88 (1994).
Demeule et al., "Conjugation of a brain-penetrant peptide with neurotensin provides antinociceptive properties," J Clin Invest. 124(3), 2014 (15 pages).
Derossi et al., "The third helix of the Antennapedia homeodomain translocates through biological membranes," J Biol Chem. 269(14):10444-50 (1994).
Egger-Heigold, Barbara, Thesis: "The effect of excipients on pharmacokinetic parameters of parenteral drugs," Doctorate, University of Basel, 2005.
Gabathuler et al., "117 POSTER ANG1005, Paclitaxel conjugated to the angiopep brain transport vector for the treatment of brain cancer: preclinical studies," Eur J Cancer. 6(12):38-9 (2008).
Gabathuler et al., "147 POSTER A new Taxol delivery system for the treatment of brain primary or metastatic tumors," Eur J Cancer. 4(12):47-8 (2006).
Gaillard et al., "Targeted delivery across the blood-brain barrier," Expert Opin Drug Deliv. 2(2):299-309 (2005).

(56) References Cited

OTHER PUBLICATIONS

Gavrilov et al., "Therapeutic siRNA: principles, challenges, and strategies," Yale J Biol Med. 85(2):187-200 (2012).
Henderson et al., "Terminal amino acid sequences and proteolytic cleavage sites of mouse mammary tumor virus env gene products," J Virol. 48(1):314-9 (1983).
Jiang et al., "Tumor cell targeting of transferrin-PEG-TNF-alpha conjugate via a receptor-mediated delivery system: design, synthesis, and biological evaluation," Bioconjug Chem. 18(1):41-9 (2007).
Jodoin et al., "P-glycoprotein in blood-brain barrier endothelial cells: interaction and oligomerization with caveolins," J Neurochem. 87(4):1010-23 (2003).
Katz et al., "Neurotensin-induced hypothermia improves neurologic outcome after hypoxic-ischemia," Crit Care Med. 32(3):806-10 (2004).
Kurzrock et al., "424 POSTER ANG1005, an Angiopep-2/paclitaxel conjugate: the first clinical trial in patients with advanced cancer and brain metastases: Preliminary safety and tolerability data," Eur J Cancer. 6(12):133 (2008).
Li et al., "Expression of alpha2-macroglobulin receptor/low density lipoprotein receptor-related protein on surfaces of tumour cells: a study using flow cytometry," Cancer Lett. 111(1-2):199-205 (1997).
Mazza et al., "Cancer and the blood-brain barrier: 'Trojan horses' for courses?" Br J Pharmacol. 155(2):149-51 (2008).
Nagy et al., "Design, synthesis, and in vitro evaluation of cytotoxic analogs of bombesin-like peptides containing doxorubicin or its intensely potent derivative, 2-pyrrolinodoxorubicin," Proc Natl Acad Sci USA. 94(2):652-6 (1997).
Nagy et al., "Targeting of cytotoxic luteinizing hormone-releasing hormone analogs to breast, ovarian, endometrial, and prostate cancers," Biol Reprod. 73(5):851-9 (2005).
Notice of Reasons for Rejection for Japanese Patent Application No. 2011-531313, mailed on Apr. 15, 2014 (2 pages).
Patel et al., "Getting into the brain: approaches to enhance brain drug delivery," CNS Drugs. 23(1):35-58 (2009).
Regina et al., "Antitumour activity of ANG1005, a conjugate between paclitaxel and the new brain delivery vector Angiopep-2," Br J Pharmacol. 155(2):185-97 (2008).
Tripathi et al., "Membrane type 1 matrix metalloproteinase expression in human atherosclerotic plaques: evidence for activation by proinflammatory mediators," Circulation. 99(24):3103-9 (1999).
Tyler et al., "Evidence for additional neurotensin receptor subtypes: neurotensin analogs that distinguish between neurotensin-mediated hypothermia and antinociception," Brain Res. 792(2):246-52 (1998).
van de Waterbeemd et al., "Lipophilicity of amino acids," Amino Acids. 7(2):129-45 (1994).
Wei et al., "Retro-Inverso Isomer of Angiopep-2: A Stable d-Peptide Ligand Inspires Brain-Targeted Drug Delivery," Mol Pharm. Epub ahead of print, available online Mar. 2014, (8 pages).
Ziske et al., "Acute transient encephalopathy after paclitaxel infusion: report of three cases," Ann Oncol. 13(4):629-31 (2002).
Zuckermann et al., "Discovery of nanomolar ligands for 7-transmembrane G-protein-coupled receptors from a diverse N-(substituted)glycine peptoid library," J Med Chem. 37(17):2678-85 (1994).

* cited by examiner

| Peptides | Amino acid sequence |
|---|---|
| Exendin-4 native | HGEGTFTSDLSKQMEEEAVRLFIEWLKNGGPSSGAPPPS |
| Exendin-4-Lys(MHA) | HGEGTFTSDLSKQMEEEAVRLFIEWLKNGGPSSGAPPPK-(MHA) |
| (Cys32)-Exendin-4 | HGEGTFTSDLSKQMEEEAVRLFIEWLKNGGPCSGAPPPS |

| Series I | Qtty (mg) | Purity (%) | MW (g/mol) |
|---|---|---|---|
| Ex-4-AN2 (N-Terminal) | 4.9 | > 95 | 6825.45 |
| Ex-4-AN2 (C-Terminal) | 5.5 | > 95 | 6825.48 |
| Ex-4-AN1 | 5.3 | > 85 | 6739.38 |

First treatment

His-Gly-Glu-Gly-Thr-Phe-Thr-Ser-Asp-Leu-Ser-Lys-Gln-Met-Glu-Glu-Glu-Ala-Val-Arg-Leu-
Phe-Ile-Glu-Trp-Leu-Lys-Asn-Gly-Gly-Pro-Ser-Ser-Gly-Ala-Pro-Pro-Pro-(Lys39)

SEQUENCE LISTING

<160> NUMBER OF SEQ ID NOS: 140

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Phe Tyr Tyr Gly Gly Cys Leu Gly Asn Lys Asn Asn Tyr Leu Arg
1               5                   10                  15

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (19)..(19)
<223> OTHER INFORMATION: C-term may or may not be amidated

```
<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Phe Tyr Gly Gly Cys Arg Ala Lys Lys Asn Asn Tyr Lys Arg
1               5                   10                  15

Ala Lys Tyr

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Phe Gln Tyr Gly Gly Cys Arg Ala Lys Arg Asn Asn Phe Lys Arg
1               5                   10                  15

Ala Lys Tyr

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Phe Phe Tyr Gly Gly Cys Gly Ala Asn Arg Asn Asn Phe Lys Arg
1               5                   10                  15

Ala Lys Tyr

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 25

Thr Phe Phe Tyr Gly Gly Ser Arg Gly Asn Arg Asn Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Phe Phe Tyr Gly Gly Cys Leu Gly Asn Gly Asn Asn Phe Lys Arg
1               5                   10                  15

Ala Lys Tyr

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Phe Phe Tyr Gly Gly Ser Arg Gly Lys Gly Asn Asn Phe Asp Arg
1               5                   10                  15

Ala Lys Tyr

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Phe Phe Tyr Gly Gly Cys Leu Gly Lys Gly Asn Asn Phe Leu Thr
1               5                   10                  15

Ala Lys Tyr

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Phe Phe Tyr Gly Gly Cys Gly Gly Asn Lys Asn Asn Phe Val Arg
1               5                   10                  15

Glu Lys Tyr

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Phe Phe Tyr Gly Gly Ser Met Gly Asn Lys Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Phe Phe Tyr Gly Gly Cys Leu Gly Asn Arg Asn Tyr Val Arg
1               5                   10                  15

Glu Lys Tyr

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Phe Phe Tyr Gly Gly Cys Leu Gly Asn Arg Asn Phe Val Arg
1               5                   10                  15

Glu Lys Tyr

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Phe Phe Tyr Gly Gly Cys Leu Gly Asn Lys Asn Tyr Val Arg
1               5                   10                  15

Glu Lys Tyr

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Phe Phe Tyr Gly Gly Cys Gly Gly Asn Gly Asn Phe Leu Thr
1               5                   10                  15

Ala Lys Tyr
```

```
<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Phe Phe Tyr Gly Gly Cys Arg Gly Asn Gly Asn Asn Phe Lys Ser
1               5                   10                  15

Ala Glu Tyr

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Phe Phe Tyr Gly Gly Cys Arg Gly Lys Arg Asn Asn Phe Lys Thr
1               5                   10                  15

Glu Glu Asp
```

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Phe Phe Tyr Gly Gly Cys Gly Gly Asn Gly Asn Asn Phe Leu Arg
1               5                   10                  15

Glu Lys Tyr

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Phe Phe Tyr Gly Gly Cys Leu Gly Asn Gly Asn Asn Phe Val Arg
1               5                   10                  15

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Phe Phe Tyr Gly Gly Cys Leu Gly Asn Gly Asn Asn Tyr Leu Arg
1               5                   10                  15

Glu Lys Tyr

```
<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Phe Phe Tyr Gly Gly Cys Leu Gly Lys Gly Asn Asn Phe Val Ser
1               5                   10                  15

Ala Glu Tyr

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Phe Phe Tyr Gly Gly Cys Leu Gly Asn Arg Asn Asn Phe Asp Arg
1               5                   10                  15

Ala Glu Tyr

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Phe Phe Tyr Gly Gly Cys Leu Gly Asn Arg Asn Asn Phe Leu Arg
1               5                   10                  15
```

Glu Glu Tyr

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Phe Phe Tyr Gly Gly Ser Gly Gly Asn Arg Asn Asn Tyr Leu Arg
1               5                   10                  15

Glu Glu Tyr

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Arg Pro Asp Phe Cys Leu Glu Pro Pro Tyr Thr Gly Pro Cys Val
1               5                   10                  15

Ala Arg Ile

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Arg Ile Ile Arg Tyr Phe Tyr Asn Ala Lys Ala Gly Leu Cys Gln
1               5                   10                  15

```
Thr Phe Val Tyr Gly
            20

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Gly Gly Cys Arg Ala Lys Arg Asn Asn Tyr Lys Ser Ala Glu Asp
1               5                   10                  15

Cys Met Arg Thr Cys Gly
            20

<210> SEQ ID NO 66
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Asp Phe Cys Leu Glu Pro Pro Tyr Thr Gly Pro Cys Val Ala Arg
1               5                   10                  15

Ile Ile Arg Tyr Phe Tyr
            20

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (19)..(19)
<223> OTHER INFORMATION: C-term may or may not be amidated

<400> SEQUENCE: 67

Thr Phe Phe Tyr Gly Gly Cys Arg Gly Lys Arg Asn Asn Phe Lys Thr
1               5                   10                  15

Glu Glu Tyr

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Phe Phe Tyr Gly Gly Cys Arg Gly Lys Arg Asn Asn Phe Lys Thr
1               5                   10                  15

Glu Glu Tyr Cys
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr Phe Phe Tyr Gly Ser Cys Arg Gly Lys Arg Asn Asn Phe Lys
1               5                   10                  15

Thr Glu Glu Tyr
            20
```

```
<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Phe Phe Tyr Gly Gly Cys Arg Gly Lys Arg Asn Asn Phe Lys Thr
1               5                   10                  15

Glu Glu Tyr

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (19)..(19)
<223> OTHER INFORMATION: C-term may or may not be amidated

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Phe Phe Tyr Gly Gly Lys Arg Gly Lys Arg Asn Asn Phe Lys Thr
1               5                   10                  15

Glu Glu Tyr

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

```
Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Phe Phe Tyr Gly Gly Lys Arg Gly Lys Arg Asn Asn Phe Lys Thr
1               5                   10                  15

Ala Gly Tyr

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Phe Phe Tyr Gly Gly Lys Arg Gly Lys Arg Asn Asn Phe Lys Arg
1               5                   10                  15

Ala Lys Tyr

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

```
Thr Phe Phe Tyr Gly Gly Cys Leu Gly Asn Arg Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Phe Phe Tyr Gly Gly Arg Cys Gly Lys Arg Asn Asn Phe Lys Thr
1               5                   10                  15

Glu Glu Tyr

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Phe Phe Tyr Gly Gly Cys Leu Gly Asn Gly Asn Asn Phe Asp Thr
1               5                   10                  15

Glu Glu Glu

<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Phe Gln Tyr Gly Gly Cys Arg Gly Lys Arg Asn Asn Phe Lys Thr
1               5                   10                  15

Glu Glu Tyr

<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 88

Tyr Asn Lys Glu Phe Gly Thr Phe Asn Thr Lys Gly Cys Glu Arg Gly
1               5                   10                  15

Tyr Arg Phe

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Phe Lys Tyr Gly Gly Cys Leu Gly Asn Met Asn Asn Phe Glu Thr
1               5                   10                  15

Leu Glu Glu

<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Phe Lys Tyr Gly Gly Cys Leu Gly Asn Lys Asn Asn Phe Leu Arg
1               5                   10                  15

Leu Lys Tyr

<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (19)..(19)
<223> OTHER INFORMATION: C-term may or may not be amidated

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20

<210> SEQ ID NO 93
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Gly Gly Arg Leu Ser Tyr Ser Arg Arg Phe Ser Thr Ser Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Leu Ser Tyr Ser Arg Arg Arg Phe
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Phe Phe Tyr Gly Gly Ser Arg Gly Lys Arg Asn Asn Phe Lys Thr
1               5                   10                  15

Glu Glu Tyr

<210> SEQ ID NO 98
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
            20                  25                  30

Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
    50                  55

<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Phe Lys Tyr Gly Gly Cys Leu Gly Asn Lys Asn Asn Tyr Leu Arg
1               5                   10                  15

Leu Lys Tyr

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Phe Phe Tyr Gly Gly Cys Arg Ala Lys Arg Asn Asn Phe Lys Arg
1               5                   10                  15

Ala Lys Tyr

<210> SEQ ID NO 102
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
            20                  25                  30
```

Gly Gly Ala
        35

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Gly Gly Cys Arg Ala Lys Arg Asn Asn Phe Lys Ser Ala Glu Asp
1               5                   10                  15

Cys Met Arg Thr Cys Gly Gly Ala
            20

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Leu Cys Gln Thr Phe Val Tyr Gly Gly Cys Arg Ala Lys Arg Asn
1               5                   10                  15

Asn Phe Lys Ser Ala Glu
            20

<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
atgagaccag atttctgcct cgagccgccg tacactgggc cctgcaaagc tcgtatcatc      60
cgttacttct acaatgcaaa ggcaggcctg tgtcagacct tcgtatacgg cggctgcaga     120
gctaagcgta caacttcaa atccgcggaa gactgcatgc gtacttgcgg tggtgcttag      180

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic

```
                    peptide
<220> FEATURE:
<221> NAME/KEY: MISC_FEATURE
<222> LOCATION: (19)..(19)
<223> OTHER INFORMATION: C-term may or may not be amidated

<400> SEQUENCE: 107

Thr Phe Phe Tyr Gly Gly Ser Arg Gly Lys Arg Asn Asn Phe Lys Thr
1               5                   10                  15

Glu Glu Tyr

<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Phe Phe Tyr Gly Gly Ser Arg Gly Lys Arg Asn Asn Phe Lys Thr
1               5                   10                  15

Glu Glu Tyr

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (19)..(19)
<223> OTHER INFORMATION: C-term may or may not be amidated

<400> SEQUENCE: 109

Arg Phe Phe Tyr Gly Gly Ser Arg Gly Lys Arg Asn Asn Phe Lys Thr
1               5                   10                  15

Glu Glu Tyr

<210> SEQ ID NO 110
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (19)..(19)
<223> OTHER INFORMATION: C-term may or may not be amidated

<400> SEQUENCE: 110

Arg Phe Phe Tyr Gly Gly Ser Arg Gly Lys Arg Asn Asn Phe Arg Thr
1               5                   10                  15

Glu Glu Tyr

<210> SEQ ID NO 111
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111
```

Thr Phe Phe Tyr Gly Gly Ser Arg Gly Lys Arg Asn Asn Phe Arg Thr
1               5                   10                  15

Glu Glu Tyr

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Phe Phe Tyr Gly Gly Ser Arg Gly Arg Arg Asn Asn Phe Arg Thr
1               5                   10                  15

Glu Glu Tyr

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 114
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Thr Phe Phe Tyr Gly Gly Ser Arg Gly Arg Arg Asn Asn Phe Arg
1               5                   10                  15

Thr Glu Glu Tyr
            20

<210> SEQ ID NO 116
<211> LENGTH: 20
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 116

Thr Phe Phe Tyr Gly Gly Ser Arg Gly Arg Arg Asn Asn Phe Arg Thr
1               5                  10                  15

Glu Glu Tyr Cys
            20

<210> SEQ ID NO 117
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

His Gly Glu Gly Thr Phe Thr Ser Asp Leu Ser Lys Gln Met Glu Glu
1               5                  10                  15

Glu Ala Val Arg Leu Phe Ile Glu Trp Leu Lys Asn Gly Gly Pro Ser
            20                  25                  30

Ser Gly Ala Pro Pro Lys
        35

<210> SEQ ID NO 118
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

His Gly Glu Gly Thr Phe Thr Ser Asp Leu Ser Lys Gln Met Glu Glu
1               5                  10                  15

Glu Ala Val Arg Leu Phe Ile Glu Trp Leu Lys Asn Gly Gly Pro Cys
            20                  25                  30

Ser Gly Ala Pro Pro Ser
        35

<210> SEQ ID NO 119
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Tyr Lys Gly Glu Arg Tyr Arg Gly Phe Lys Glu Thr Asn Phe Asn
1               5                  10                  15

Thr Phe Ser

<210> SEQ ID NO 120
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

His Gly Glu Gly Thr Phe Thr Ser Asp Leu Ser Lys Gln Met Glu Glu
```

```
  1               5                  10                  15
Glu Ala Val Arg Leu Phe Ile Glu Trp Leu Lys Asn Gly Gly Pro Ser
         20                  25                  30
Ser Gly Ala Pro Pro Ser
         35

<210> SEQ ID NO 121
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, Arg or Tyr
<220> FEATURE:
<221> NAME/KEY: MOD_RES
<222> LOCATION: (2)..(2)
<223> OTHER INFORMATION: Ser, Gly, Ala or Thr
<220> FEATURE:
<221> NAME/KEY: MOD_RES
<222> LOCATION: (3)..(3)
<223> OTHER INFORMATION: Asp or Glu
<220> FEATURE:
<221> NAME/KEY: MOD_RES
<222> LOCATION: (6)..(6)
<223> OTHER INFORMATION: Phe, Tyr or Nal
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (9)..(9)
<223> OTHER INFORMATION: Asp or Glu
<220> FEATURE:
<221> NAME/KEY: MOD_RES
<222> LOCATION: (10)..(10)
<223> OTHER INFORMATION: Leu, Ile, Val, pGly or Met
<220> FEATURE:
<221> NAME/KEY: MOD_RES
<222> LOCATION: (14)..(14)
<223> OTHER INFORMATION: Leu, Ile, pGly, Val or Met
<220> FEATURE:
<221> NAME/KEY: MOD_RES
<222> LOCATION: (22)..(22)
<223> OTHER INFORMATION: Phe, Tyr or Nal
<220> FEATURE:
<221> NAME/KEY: MOD_RES
<222> LOCATION: (23)..(23)
<223> OTHER INFORMATION: Ile, Val, Leu, pGly, t-BuGly or Met
<220> FEATURE:
<221> NAME/KEY: MOD_RES
<222> LOCATION: (24)..(24)
<223> OTHER INFORMATION: Glu or Asp
<220> FEATURE:
<221> NAME/KEY: MOD_RES
<222> LOCATION: (25)..(25)
<223> OTHER INFORMATION: Trp, Phe, Tyr or Nal
<220> FEATURE:
<221> NAME/KEY: MOD_RES
<222> LOCATION: (31)..(31)
<223> OTHER INFORMATION: Pro, HPro, 3Hyp, 4Hyp, TPro, N-alkylglycine,
      N-alkyl-pGly or N-alkylalanine
<220> FEATURE:
<221> NAME/KEY: MOD_RES
<222> LOCATION: (36)..(38)
<223> OTHER INFORMATION: Pro, HPro, 3Hyp, 4Hyp, TPro, N-alkylglycine,
      N-alkyl-pGly or N-alkylalanine
<220> FEATURE:
```

```
<221> NAME/KEY: MOD_RES
<222> LOCATION: (39)..(39)
<223> OTHER INFORMATION: Ser, Thr or Tyr

<400> SEQUENCE: 121

Xaa Xaa Xaa Gly Thr Xaa Xaa Xaa Xaa Xaa Ser Lys Gln Xaa Glu Glu
1               5                   10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
        35

<210> SEQ ID NO 122
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, Arg or Tyr
<220> FEATURE:
<221> NAME/KEY: MOD_RES
<222> LOCATION: (2)..(2)
<223> OTHER INFORMATION: Ser, Gly, Ala or Thr
<220> FEATURE:
<221> NAME/KEY: MOD_RES
<222> LOCATION: (3)..(3)
<223> OTHER INFORMATION: Asp or Glu
<220> FEATURE:
<221> NAME/KEY: MOD_RES
<222> LOCATION: (5)..(5)
<223> OTHER INFORMATION: Ala or Thr
<220> FEATURE:
<221> NAME/KEY: MOD_RES
<222> LOCATION: (6)..(6)
<223> OTHER INFORMATION: Ala, Phe, Tyr or Nal
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Ala, Ser or Thr
<220> FEATURE:
<221> NAME/KEY: MOD_RES
<222> LOCATION: (9)..(9)
<223> OTHER INFORMATION: Asp or Glu
<220> FEATURE:
<221> NAME/KEY: MOD_RES
<222> LOCATION: (10)..(10)
<223> OTHER INFORMATION: Ala, Leu, Ile, Val, pGly or Met
<220> FEATURE:
<221> NAME/KEY: MOD_RES
<222> LOCATION: (11)..(11)
<223> OTHER INFORMATION: Ala or Ser
<220> FEATURE:
<221> NAME/KEY: MOD_RES
<222> LOCATION: (12)..(12)
<223> OTHER INFORMATION: Ala or Lys
<220> FEATURE:
<221> NAME/KEY: MOD_RES
<222> LOCATION: (13)..(13)
<223> OTHER INFORMATION: Ala or Gln
<220> FEATURE:
<221> NAME/KEY: MOD_RES
<222> LOCATION: (14)..(14)
<223> OTHER INFORMATION: Ala, Leu, Ile, pGly, Val or Met
<220> FEATURE:
<221> NAME/KEY: MOD_RES
<222> LOCATION: (15)..(17)
<223> OTHER INFORMATION: Ala or Glu
```

```
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Ala or Arg
<220> FEATURE:
<221> NAME/KEY: MOD_RES
<222> LOCATION: (21)..(21)
<223> OTHER INFORMATION: Ala or Leu
<220> FEATURE:
<221> NAME/KEY: MOD_RES
<222> LOCATION: (22)..(22)
<223> OTHER INFORMATION: Phe, Tyr or Nal
<220> FEATURE:
<221> NAME/KEY: MOD_RES
<222> LOCATION: (23)..(23)
<223> OTHER INFORMATION: Ile, Val, Leu, pGly, t-BuGly or Met
<220> FEATURE:
<221> NAME/KEY: MOD_RES
<222> LOCATION: (24)..(24)
<223> OTHER INFORMATION: Ala, Glu or Asp
<220> FEATURE:
<221> NAME/KEY: MOD_RES
<222> LOCATION: (25)..(25)
<223> OTHER INFORMATION: Ala, Trp, Phe, Tyr or Nal
<220> FEATURE:
<221> NAME/KEY: MOD_RES
<222> LOCATION: (26)..(26)
<223> OTHER INFORMATION: Ala or Leu
<220> FEATURE:
<221> NAME/KEY: MOD_RES
<222> LOCATION: (27)..(27)
<223> OTHER INFORMATION: Ala or Lys
<220> FEATURE:
<221> NAME/KEY: MOD_RES
<222> LOCATION: (28)..(28)
<223> OTHER INFORMATION: Ala or Asn
<220> FEATURE:
<221> NAME/KEY: MOD_RES
<222> LOCATION: (29)..(30)
<223> OTHER INFORMATION: Gly or absent
<220> FEATURE:
<221> NAME/KEY: MOD_RES
<222> LOCATION: (31)..(31)
<223> OTHER INFORMATION: Pro, HPro, 3Hyp, 4Hyp, TPro, N-alkylglycine,
     N-alkyl-pGly, N-alkylalanine or absent
<220> FEATURE:
<221> NAME/KEY: MOD_RES
<222> LOCATION: (32)..(33)
<223> OTHER INFORMATION: Ser or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Ala or absent
<220> FEATURE:
<221> NAME/KEY: MOD_RES
<222> LOCATION: (36)..(38)
<223> OTHER INFORMATION: Pro, HPro, 3Hyp, 4Hyp, TPro, N-alkylglycine,
     N-alkyl-pGly, N-alkylalanine or absent

<400> SEQUENCE: 122

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa
        35
```

-continued

```
<210> SEQ ID NO 123
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide. see specification as filed for detailed description of
      substitutions and preferred embodiments
<220> FEATURE:
<221> NAME/KEY: MOD_RES
<222> LOCATION: (1)..(1)
<223> OTHER INFORMATION: His, Arg, Tyr, Ala, Norval, Val or Norleu
<220> FEATURE:
<221> NAME/KEY: MOD_RES
<222> LOCATION: (2)..(2)
<223> OTHER INFORMATION: Ser, Gly, Ala or Thr
<220> FEATURE:
<221> NAME/KEY: MOD_RES
<222> LOCATION: (3)..(3)
<223> OTHER INFORMATION: Ala, Asp or Glu
<220> FEATURE:
<221> NAME/KEY: MOD_RES
<222> LOCATION: (4)..(4)
<223> OTHER INFORMATION: Ala, Norval, Val, Norleu or Gly
<220> FEATURE:
<221> NAME/KEY: MOD_RES
<222> LOCATION: (5)..(5)
<223> OTHER INFORMATION: Ala or Thr
<220> FEATURE:
<221> NAME/KEY: MOD_RES
<222> LOCATION: (6)..(6)
<223> OTHER INFORMATION: Phe, Tyr or Nal
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Ala, Ser or Thr
<220> FEATURE:
<221> NAME/KEY: MOD_RES
<222> LOCATION: (9)..(9)
<223> OTHER INFORMATION: Ala, Norval, Val, Norleu, Asp or Glu
<220> FEATURE:
<221> NAME/KEY: MOD_RES
<222> LOCATION: (10)..(10)
<223> OTHER INFORMATION: Ala, Leu, Ile, Val, pGly or Met
<220> FEATURE:
<221> NAME/KEY: MOD_RES
<222> LOCATION: (11)..(11)
<223> OTHER INFORMATION: Ala or Ser
<220> FEATURE:
<221> NAME/KEY: MOD_RES
<222> LOCATION: (12)..(12)
<223> OTHER INFORMATION: Ala or Lys
<220> FEATURE:
<221> NAME/KEY: MOD_RES
<222> LOCATION: (13)..(13)
<223> OTHER INFORMATION: Ala or Gln
<220> FEATURE:
<221> NAME/KEY: MOD_RES
<222> LOCATION: (14)..(14)
<223> OTHER INFORMATION: Ala, Leu, Ile, pGly, Val or Met
<220> FEATURE:
<221> NAME/KEY: MOD_RES
<222> LOCATION: (15)..(17)
<223> OTHER INFORMATION: Ala or Glu
<220> FEATURE:
<221> NAME/KEY: MOD_RES
<222> LOCATION: (19)..(19)
<223> OTHER INFORMATION: Ala or Val
<220> FEATURE:
<221> NAME/KEY: MOD_RES
<222> LOCATION: (20)..(20)
<223> OTHER INFORMATION: Ala or Arg
<220> FEATURE:
<221> NAME/KEY: MOD_RES
<222> LOCATION: (21)..(21)
```

```
<223> OTHER INFORMATION: Ala or Leu
<220> FEATURE:
<221> NAME/KEY: MOD_RES
<222> LOCATION: (22)..(22)
<223> OTHER INFORMATION: Phe, Tyr or Nal
<220> FEATURE:
<221> NAME/KEY: MOD_RES
<222> LOCATION: (23)..(23)
<223> OTHER INFORMATION: Ile, Val, Leu, pGly, t-BuGly or Met
<220> FEATURE:
<221> NAME/KEY: MOD_RES
<222> LOCATION: (24)..(24)
<223> OTHER INFORMATION: Ala, Glu or Asp
<220> FEATURE:
<221> NAME/KEY: MOD_RES
<222> LOCATION: (25)..(25)
<223> OTHER INFORMATION: Ala, Trp, Phe, Tyr or Nal
<220> FEATURE:
<221> NAME/KEY: MOD_RES
<222> LOCATION: (26)..(26)
<223> OTHER INFORMATION: Ala or Leu
<220> FEATURE:
<221> NAME/KEY: MOD_RES
<222> LOCATION: (27)..(27)
<223> OTHER INFORMATION: Ala or Lys
<220> FEATURE:
<221> NAME/KEY: MOD_RES
<222> LOCATION: (28)..(28)
<223> OTHER INFORMATION: Ala or Asn
<220> FEATURE:
<221> NAME/KEY: MOD_RES
<222> LOCATION: (29)..(30)
<223> OTHER INFORMATION: Gly or absent
<220> FEATURE:
<221> NAME/KEY: MOD_RES
<222> LOCATION: (31)..(31)
<223> OTHER INFORMATION: Pro, HPro, 3Hyp, 4Hyp, TPro, N-alkylglycine,
     N-alkyl-pGly, N-alkylalanine or absent
<220> FEATURE:
<221> NAME/KEY: MOD_RES
<222> LOCATION: (32)..(33)
<223> OTHER INFORMATION: Ser or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Ala or absent
<220> FEATURE:
<221> NAME/KEY: MOD_RES
<222> LOCATION: (36)..(38)
<223> OTHER INFORMATION: Pro, HPro, 3Hyp, 4Hyp, TPro, N-alkylglycine,
     N-alkyl-pGly, N-alkylalanine or absent
<220> FEATURE:
<221> NAME/KEY: misc_feature
<222> LOCATION: (38)..(38)
<223> OTHER INFORMATION: C-term may or may not be amidated

<400> SEQUENCE: 123

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa
        35

<210> SEQ ID NO 124
<211> LENGTH: 40
<212> TYPE: PRT
<213> ORGANISM: Artificial Sequence
<220> FEATURE:
<223> OTHER INFORMATION: Description of Artificial Sequence: Synthetic
     polypeptide
```

```
<220> FEATURE:
<221> NAME/KEY: MOD_RES
<222> LOCATION: (14)..(14)
<223> OTHER INFORMATION: Arg, Leu, Ile or Met
<220> FEATURE:
<221> NAME/KEY: MOD_RES
<222> LOCATION: (20)..(20)
<223> OTHER INFORMATION: His, Arg or Lys
<220> FEATURE:
<221> NAME/KEY: MOD_RES
<222> LOCATION: (40)..(40)
<223> OTHER INFORMATION: Arg, Lys, or absent
<220> FEATURE:
<221> NAME/KEY: MISC_FEATURE
<222> LOCATION: (40)..(40)
<223> OTHER INFORMATION: C-term may or may not be amindated

<400> SEQUENCE: 124

His Gly Glu Gly Thr Phe Thr Ser Asp Leu Ser Lys Gln Xaa Glu Glu
1               5                   10                  15

Glu Ala Val Xaa Leu Phe Ile Glu Trp Leu Lys Asn Gly Gly Pro Ser
            20                  25                  30

Ser Gly Ala Pro Pro Pro Ser Xaa
        35                  40

<210> SEQ ID NO 125
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Phe or Tyr
<220> FEATURE:
<221> NAME/KEY: MOD_RES
<222> LOCATION: (14)..(14)
<223> OTHER INFORMATION: Met, Ile or Leu
<220> FEATURE:
<221> NAME/KEY: MOD_RES
<222> LOCATION: (30)..(30)
<223> OTHER INFORMATION: Gly or absent
<220> FEATURE:
<221> NAME/KEY: MOD_RES
<222> LOCATION: (32)..(32)
<223> OTHER INFORMATION: Arg or absent

<400> SEQUENCE: 125

His Gly Glu Gly Thr Xaa Thr Ser Asp Leu Ser Lys Gln Xaa Glu Glu
1               5                   10                  15

Glu Ala Val Lys Leu Phe Ile Glu Trp Leu Lys Asn Gly Xaa Pro Xaa
            20                  25                  30

<210> SEQ ID NO 126
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any neutral amino acid, Asp, N-acylated His,
      alkylated His or His
<220> FEATURE:
<221> NAME/KEY: MISC_FEATURE
<222> LOCATION: (1)..(1)
<223> OTHER INFORMATION: May be an N-acylated or N-alkyated amion acid
<220> FEATURE:
```

```
<221> NAME/KEY: MOD_RES
<222> LOCATION: (2)..(2)
<223> OTHER INFORMATION: Any small neutral amino acid or Ala
<220> FEATURE:
<221> NAME/KEY: MOD_RES
<222> LOCATION: (3)..(3)
<223> OTHER INFORMATION: Any acidic amino acid, a neutral amino acid
      or Glu
<220> FEATURE:
<221> NAME/KEY: MOD_RES
<222> LOCATION: (4)..(4)
<223> OTHER INFORMATION: Any neutral amino acid or Gly
<220> FEATURE:
<221> NAME/KEY: MOD_RES
<222> LOCATION: (9)..(9)
<223> OTHER INFORMATION: Any acidic amino acid or Asp
<220> FEATURE:
<221> NAME/KEY: MOD_RES
<222> LOCATION: (10)..(10)
<223> OTHER INFORMATION: Tyr or Val
<220> FEATURE:
<221> NAME/KEY: MOD_RES
<222> LOCATION: (12)..(12)
<223> OTHER INFORMATION: Lys or Ser
<220> FEATURE:
<221> NAME/KEY: MOD_RES
<222> LOCATION: (15)..(15)
<223> OTHER INFORMATION: Asp or Glu
<220> FEATURE:
<221> NAME/KEY: MOD_RES
<222> LOCATION: (16)..(16)
<223> OTHER INFORMATION: Ser or Gly
<220> FEATURE:
<221> NAME/KEY: MOD_RES
<222> LOCATION: (17)..(17)
<223> OTHER INFORMATION: Arg or Gln
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (20)..(20)
<223> OTHER INFORMATION: Any neutral amino acid, Arg, D-Lys, Gln or Lys
<220> FEATURE:
<221> NAME/KEY: MOD_RES
<222> LOCATION: (25)..(25)
<223> OTHER INFORMATION: Any oxidation-resistant amino acid or Trp
<220> FEATURE:
<221> NAME/KEY: MOD_RES
<222> LOCATION: (28)..(28)
<223> OTHER INFORMATION: Any neutral amino acid, Arg, D-Lys or Lys
<220> FEATURE:
<221> NAME/KEY: MOD_RES
<222> LOCATION: (29)..(29)
<223> OTHER INFORMATION: Gly or absent
<220> FEATURE:
<221> NAME/KEY: MOD_RES
<222> LOCATION: (30)..(30)
<223> OTHER INFORMATION: Any neutral amino acid, Lys, D-Arg, Arg or
      absent
<220> FEATURE:
<221> NAME/KEY: MOD_RES
<222> LOCATION: (31)..(31)
<223> OTHER INFORMATION: Gly or absent

<400> SEQUENCE: 126

Xaa Xaa Xaa Xaa Thr Phe Thr Ser Xaa Xaa Ser Xaa Tyr Leu Xaa Xaa
1               5                   10                  15

Xaa Xaa Ala Xaa Glu Phe Ile Ala Xaa Leu Val Xaa Xaa Xaa Xaa
            20                  25                  30

<210> SEQ ID NO 127
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala or absent
<220> FEATURE:
<221> NAME/KEY: MOD_RES
<222> LOCATION: (2)..(2)
<223> OTHER INFORMATION: Glu or absent
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Thr or absent
<220> FEATURE:
<221> NAME/KEY: MOD_RES
<222> LOCATION: (5)..(5)
<223> OTHER INFORMATION: Phe or absent
<220> FEATURE:
<221> NAME/KEY: MOD_RES
<222> LOCATION: (6)..(6)
<223> OTHER INFORMATION: Thr or absent
<220> FEATURE:
<221> NAME/KEY: MOD_RES
<222> LOCATION: (7)..(7)
<223> OTHER INFORMATION: Ser or absent
<220> FEATURE:
<221> NAME/KEY: MOD_RES
<222> LOCATION: (8)..(8)
<223> OTHER INFORMATION: Asp or absent
<220> FEATURE:
<221> NAME/KEY: MOD_RES
<222> LOCATION: (9)..(9)
<223> OTHER INFORMATION: Val or absent
<220> FEATURE:
<221> NAME/KEY: MOD_RES
<222> LOCATION: (10)..(10)
<223> OTHER INFORMATION: Ser or absent
<220> FEATURE:
<221> NAME/KEY: MOD_RES
<222> LOCATION: (27)..(27)
<223> OTHER INFORMATION: Lys or Arg
<220> FEATURE:
<221> NAME/KEY: MISC_FEATURE
<222> LOCATION: (29)..(30)
<223> OTHER INFORMATION: C-terminal may or may not be amidated
<220> FEATURE:
<221> NAME/KEY: MOD_RES
<222> LOCATION: (30)..(30)
<223> OTHER INFORMATION: Gly or absent

<400> SEQUENCE: 127

Xaa Xaa Xaa Xaa Xaa Xaa Xaa Xaa Xaa Xaa Ser Tyr Leu Glu Gly Gln
1               5                   10                  15

Ala Ala Lys Glu Phe Ile Ala Trp Leu Val Xaa Gly Arg Xaa
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Lys or absent
<220> FEATURE:
<221> NAME/KEY: MOD_RES
<222> LOCATION: (29)..(29)
```

<223> OTHER INFORMATION: Gly or absent
<220> FEATURE:
<221> NAME/KEY: MOD_RES
<222> LOCATION: (30)..(30)
<223> OTHER INFORMATION: Arg or absent

<400> SEQUENCE: 128

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Xaa Xaa
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 130
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: His, D-His, desamino-His, 2-amino-His, beta-
      hydroxy-His, homohistidine, alpha-fluoromethyl-His or alpha-
      methyl-His
<220> FEATURE:
<221> NAME/KEY: MOD_RES
<222> LOCATION: (2)..(2)
<223> OTHER INFORMATION: Met, Asp, Lys, Thr, Leu, Asn, Gln, Phe, Val or
      Tyr
<220> FEATURE:
<221> NAME/KEY: MOD_RES
<222> LOCATION: (15)..(15)
<223> OTHER INFORMATION: Glu, Gln, Ala, Thr, Ser or Gly
<220> FEATURE:
<221> NAME/KEY: MOD_RES
<222> LOCATION: (21)..(21)
<223> OTHER INFORMATION: Glu, Gln, Ala, Thr, Ser or Gly
<220> FEATURE:
<221> NAME/KEY: MISC_FEATURE
<222> LOCATION: (30)..(30)
<223> OTHER INFORMATION: C-terminal is amidated, if amino acid 31 is
      absent
<220> FEATURE:
<221> NAME/KEY: MOD_RES
<222> LOCATION: (31)..(31)
<223> OTHER INFORMATION: Gly or absent

<400> SEQUENCE: 130

Xaa Xaa Glu Gly Thr Phe Thr Ser Asp Val Ser Ser Tyr Leu Xaa Gly
1               5                   10                  15

Gln Ala Ala Lys Xaa Phe Ile Ala Trp Leu Val Lys Gly Arg Xaa
            20                  25                  30

<210> SEQ ID NO 131
<211> LENGTH: 31

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: 4-imidazopropionyl (des-amino-histidyl),
      4-imidazoacetyl or 4-imidazo-alpha,alpha-dimethyl-acetyl
<220> FEATURE:
<221> NAME/KEY: MOD_RES
<222> LOCATION: (20)..(20)
<223> OTHER INFORMATION: Lys or Arg
<220> FEATURE:
<221> NAME/KEY: MOD_RES
<222> LOCATION: (28)..(28)
<223> OTHER INFORMATION: Lys or Lys having a C6-10 unbranched acyl
      bound to its side chain
<220> FEATURE:
<221> NAME/KEY: MISC_FEATURE
<222> LOCATION: (30)..(30)
<223> OTHER INFORMATION: C-terminal is amidated, if amino acid 30
      is absent
<220> FEATURE:
<221> NAME/KEY: MOD_RES
<222> LOCATION: (31)..(31)
<223> OTHER INFORMATION: Gly or absent

<400> SEQUENCE: 131

Xaa Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Xaa Gly Arg Xaa
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gly, Ala, Val, Leu, Ile, Ser or Thr
<220> FEATURE:
<221> NAME/KEY: MOD_RES
<222> LOCATION: (5)..(5)
<223> OTHER INFORMATION: Asp, Glu, Arg, Thr, Ala, Lys or His
<220> FEATURE:
<221> NAME/KEY: MOD_RES
<222> LOCATION: (6)..(6)
<223> OTHER INFORMATION: His, Trp, Phe or Tyr
<220> FEATURE:
<221> NAME/KEY: MOD_RES
<222> LOCATION: (10)..(10)
<223> OTHER INFORMATION: Leu, Ser, Thr, Trp, His, Phe, Asp, Val, Tyr,
      Glu or Ala
<220> FEATURE:
<221> NAME/KEY: MOD_RES
<222> LOCATION: (16)..(16)
<223> OTHER INFORMATION: Gly, Asp, Glu, Gln, Asn, Lys, Arg, Cys or Cya
<220> FEATURE:
<221> NAME/KEY: MOD_RES
<222> LOCATION: (17)..(17)
<223> OTHER INFORMATION: His, Asp, Lys, Glu or Gln
<220> FEATURE:
<221> NAME/KEY: MOD_RES
<222> LOCATION: (18)..(18)
<223> OTHER INFORMATION: Glu, His, Ala or Lys
<220> FEATURE:
<221> NAME/KEY: MOD_RES
<222> LOCATION: (20)..(20)
<223> OTHER INFORMATION: Asp, Lys, Glu or His
<220> FEATURE:
```

```
<221> NAME/KEY: MOD_RES
<222> LOCATION: (21)..(21)
<223> OTHER INFORMATION: Ala, Glu, His, Phe, Tyr, Trp, Arg or Lys
<220> FEATURE:
<221> NAME/KEY: MOD_RES
<222> LOCATION: (25)..(25)
<223> OTHER INFORMATION: Ala, Glu, Asp, Ser or His
<220> FEATURE:
<221> NAME/KEY: MOD_RES
<222> LOCATION: (27)..(27)
<223> OTHER INFORMATION: Asp, Arg, Val, Lys, Ala, Gly or Glu
<220> FEATURE:
<221> NAME/KEY: MOD_RES
<222> LOCATION: (28)..(28)
<223> OTHER INFORMATION: Glu, Lys or Asp
<220> FEATURE:
<221> NAME/KEY: MOD_RES
<222> LOCATION: (29)..(29)
<223> OTHER INFORMATION: Thr, Ser, Lys, Arg, Trp, Tyr, Phe, Asp, Gly,
     Pro, His or Glu
<220> FEATURE:
<221> NAME/KEY: MOD_RES
<222> LOCATION: (30)..(30)
<223> OTHER INFORMATION: Arg, Glu or His
<220> FEATURE:
<221> NAME/KEY: MISC_FEATURE
<222> LOCATION: (30)..(32)
<223> OTHER INFORMATION: C-terminal may or may not be amidated
<220> FEATURE:
<221> NAME/KEY: MOD_RES
<222> LOCATION: (31)..(31)
<223> OTHER INFORMATION: Lys, Arg, Thr, Ser, Glu, Asp, Trp, Tyr, Phe,
     His, Gly or absent
<220> FEATURE:
<221> NAME/KEY: MOD_RES
<222> LOCATION: (32)..(32)
<223> OTHER INFORMATION: Pro or absent

<400> SEQUENCE: 132

His Xaa Glu Gly Xaa Xaa Thr Ser Asp Xaa Ser Ser Tyr Leu Glu Xaa
1               5                   10                  15

Xaa Xaa Ala Xaa Xaa Phe Ile Ala Xaa Leu Xaa Xaa Xaa Xaa Xaa Xaa
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (2)..(2)
<223> OTHER INFORMATION: Gly, Ala, Val, Leu, Ile, Ser or Thr
<220> FEATURE:
<221> NAME/KEY: MOD_RES
<222> LOCATION: (6)..(6)
<223> OTHER INFORMATION: His, Trp, Phe or Tyr
<220> FEATURE:
<221> NAME/KEY: MOD_RES
<222> LOCATION: (10)..(10)
<223> OTHER INFORMATION: Leu, Ser, Thr, Trp, His, Phe, Asp, Val, Glu or
     Ala
<220> FEATURE:
<221> NAME/KEY: MOD_RES
<222> LOCATION: (16)..(16)
<223> OTHER INFORMATION: Gly, Asp, Glu, Gln, Asn, Lys, Arg, Cys or Cya
<220> FEATURE:
<221> NAME/KEY: MOD_RES
<222> LOCATION: (17)..(17)
<223> OTHER INFORMATION: His, Asp, Lys, Glu or Gln
<220> FEATURE:
<221> NAME/KEY: MOD_RES
<222> LOCATION: (20)..(20)
<223> OTHER INFORMATION: Asp, Lys, Glu or His
```

```
<220> FEATURE:
<221> NAME/KEY: MOD_RES
<222> LOCATION: (24)..(24)
<223> OTHER INFORMATION: Ala, Glu, Asp, Ser or His
<220> FEATURE:
<221> NAME/KEY: MOD_RES
<222> LOCATION: (29)..(29)
<223> OTHER INFORMATION: Thr, Ser, Lys, Arg, Trp, Tyr, Phe, Asp, Gly,
      Pro, His or Glu
<220> FEATURE:
<221> NAME/KEY: MISC_FEATURE
<222> LOCATION: (30)..(32)
<223> OTHER INFORMATION: C-terminal may be amidated
<220> FEATURE:
<221> NAME/KEY: MOD_RES
<222> LOCATION: (31)..(31)
<223> OTHER INFORMATION: Lys, Arg, Thr, Ser, Glu, Asp, Trp, Tyr, Phe,
      His, Gly or absent
<220> FEATURE:
<221> NAME/KEY: MOD_RES
<222> LOCATION: (32)..(32)
<223> OTHER INFORMATION: Pro or absent

<400> SEQUENCE: 133

His Xaa Glu Gly Thr Xaa Thr Ser Asp Xaa Ser Ser Tyr Leu Glu Xaa
1               5                   10                  15

Xaa Ala Ala Xaa Glu Phe Ile Xaa Trp Leu Val Lys Xaa Arg Xaa Xaa
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gly, Ala, Val, Leu, Ile, Ser or Thr
<220> FEATURE:
<221> NAME/KEY: MOD_RES
<222> LOCATION: (16)..(16)
<223> OTHER INFORMATION: Gly, Asp, Glu, Gln, Asn, Lys, Arg, Cys or Cya
<220> FEATURE:
<221> NAME/KEY: MOD_RES
<222> LOCATION: (17)..(17)
<223> OTHER INFORMATION: His, Asp, Lys, Glu or Gln
<220> FEATURE:
<221> NAME/KEY: MOD_RES
<222> LOCATION: (21)..(21)
<223> OTHER INFORMATION: Ala, Glu, His, Phe, Tyr, Trp, Arg or Lys
<220> FEATURE:
<221> NAME/KEY: MOD_RES
<222> LOCATION: (24)..(24)
<223> OTHER INFORMATION: Ala, Glu, Asp, Ser or His
<220> FEATURE:
<221> NAME/KEY: MISC_FEATURE
<222> LOCATION: (30)..(32)
<223> OTHER INFORMATION: C-terminal may or may not be amidated
<220> FEATURE:
<221> NAME/KEY: MOD_RES
<222> LOCATION: (31)..(31)
<223> OTHER INFORMATION: Lys, Arg, Thr, Ser, Glu, Asp, Trp, Tyr, Phe,
      His, Gly or absent
<220> FEATURE:
<221> NAME/KEY: MOD_RES
<222> LOCATION: (32)..(32)
<223> OTHER INFORMATION: Pro or absent

<400> SEQUENCE: 134

His Xaa Glu Gly Thr Phe Thr Ser Asp Val Ser Ser Tyr Leu Glu Xaa
1               5                   10                  15

Xaa Ala Ala Lys Xaa Phe Ile Xaa Trp Leu Val Lys Gly Arg Xaa Xaa
```

<210> SEQ ID NO 135
<211> LENGTH: 31
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (1)..(1)
<223> OTHER INFORMATION: L-His, D-His, desamino-His, 2amino-His, beta-
    hydroxy-His, homo-His, alpha-fluoromethyl-His or alpha-methyl-His
<220> FEATURE:
<221> NAME/KEY: MOD_RES
<222> LOCATION: (2)..(2)
<223> OTHER INFORMATION: Gly, Ala, Val, Leu, Ile, Ser or Thr
<220> FEATURE:
<221> NAME/KEY: MOD_RES
<222> LOCATION: (16)..(16)
<223> OTHER INFORMATION: Asp, Glu, Gln, Asn, Lys, Arg, Cys or Cya
<220> FEATURE:
<221> NAME/KEY: MISC_FEATURE
<222> LOCATION: (30)..(31)
<223> OTHER INFORMATION: C-terminal may or may not be amidated
<220> FEATURE:
<221> NAME/KEY: MOD_RES
<222> LOCATION: (31)..(31)
<223> OTHER INFORMATION: Gly or absent

<400> SEQUENCE: 135

Xaa Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Xaa
            20                  25                  30

<210> SEQ ID NO 136
<211> LENGTH: 31
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<221> NAME/KEY: MOD_RES
<222> LOCATION: (1)..(1)
<223> OTHER INFORMATION: L-His, D-His, desamino-His, 2-amino-His, beta-
    hydroxy-His, homohistidine, alpha-fluoromethyl-His or alpha-
    methyl-His
<220> FEATURE:
<221> NAME/KEY: MOD_RES
<222> LOCATION: (2)..(2)
<223> OTHER INFORMATION: Ala, Gly, Val, Leu, Ile, Ser or Thr
<220> FEATURE:
<221> NAME/KEY: MOD_RES
<222> LOCATION: (6)..(6)
<223> OTHER INFORMATION: Phe, Trp or Tyr
<220> FEATURE:
<221> NAME/KEY: MOD_RES
<222> LOCATION: (10)..(10)
<223> OTHER INFORMATION: Val, Trp, Ile, Leu, Phe or Tyr
<220> FEATURE:
<221> NAME/KEY: MOD_RES
<222> LOCATION: (12)..(12)
<223> OTHER INFORMATION: Ser, Trp, Tyr, Phe, Lys, Ile, Leu or Val
<220> FEATURE:
<221> NAME/KEY: MOD_RES
<222> LOCATION: (13)..(13)
<223> OTHER INFORMATION: Tyr, Trp or Phe
<220> FEATURE:
<221> NAME/KEY: MOD_RES
<222> LOCATION: (14)..(14)
<223> OTHER INFORMATION: Leu, Phe, Tyr or Trp
<220> FEATURE:

```
<221> NAME/KEY: MOD_RES
<222> LOCATION: (16)..(16)
<223> OTHER INFORMATION: Gly, Glu, Asp or Lys
<220> FEATURE:
<221> NAME/KEY: MOD_RES
<222> LOCATION: (19)..(19)
<223> OTHER INFORMATION: Ala, Val, Ile or Leu
<220> FEATURE:
<221> NAME/KEY: MOD_RES
<222> LOCATION: (21)..(21)
<223> OTHER INFORMATION: Glu, Ile or Ala
<220> FEATURE:
<221> NAME/KEY: MOD_RES
<222> LOCATION: (24)..(24)
<223> OTHER INFORMATION: Ala or Glu
<220> FEATURE:
<221> NAME/KEY: MOD_RES
<222> LOCATION: (27)..(27)
<223> OTHER INFORMATION: Val or Ile
<220> FEATURE:
<221> NAME/KEY: MISC_FEATURE
<222> LOCATION: (30)..(31)
<223> OTHER INFORMATION: C-terminal may or may not be amidated
<220> FEATURE:
<221> NAME/KEY: MOD_RES
<222> LOCATION: (31)..(31)
<223> OTHER INFORMATION: Gly, His or absent

<400> SEQUENCE: 136

Xaa Xaa Glu Gly Thr Xaa Thr Ser Asp Xaa Ser Xaa Xaa Xaa Glu Xaa
 1               5                  10                  15

Gln Ala Xaa Lys Xaa Phe Ile Xaa Trp Leu Xaa Lys Gly Arg Xaa
            20                  25                  30

<210> SEQ ID NO 137
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: L-His, D-His, desamino-His, 2-amino-His, beta-
      hydroxy-His, homohistidine, alpha-fluoromethyl-His or alpha-
      methyl-His
<220> FEATURE:
<221> NAME/KEY: MOD_RES
<222> LOCATION: (2)..(2)
<223> OTHER INFORMATION: Gly, Ala, Val, Leu, Ile, Ser or Thr
<220> FEATURE:
<221> NAME/KEY: MOD_RES
<222> LOCATION: (10)..(10)
<223> OTHER INFORMATION: Val, Phe, Tyr or Trp
<220> FEATURE:
<221> NAME/KEY: MOD_RES
<222> LOCATION: (12)..(12)
<223> OTHER INFORMATION: Ser, Tyr, Trp, Phe, Lys, Ile, Leu or Val
<220> FEATURE:
<221> NAME/KEY: MOD_RES
<222> LOCATION: (16)..(16)
<223> OTHER INFORMATION: Gly, Glu, Asp or Lys
<220> FEATURE:
<221> NAME/KEY: MOD_RES
<222> LOCATION: (19)..(19)
<223> OTHER INFORMATION: Ala, Val, Ile or Leu
<220> FEATURE:
<221> NAME/KEY: MOD_RES
<222> LOCATION: (27)..(27)
<223> OTHER INFORMATION: Val or Ile
<220> FEATURE:
<221> NAME/KEY: MISC_FEATURE
<222> LOCATION: (30)..(31)
<223> OTHER INFORMATION: C-terminal may or may not be amidated
<220> FEATURE:
```

```
<221> NAME/KEY: MOD_RES
<222> LOCATION: (31)..(31)
<223> OTHER INFORMATION: Gly or absent

<400> SEQUENCE: 137

Xaa Xaa Glu Gly Thr Phe Thr Ser Asp Xaa Ser Xaa Tyr Leu Glu Xaa
1               5                   10                  15

Gln Ala Xaa Lys Glu Phe Ile Ala Trp Leu Xaa Lys Gly Arg Xaa
            20                  25                  30

<210> SEQ ID NO 138
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(5)
<223> OTHER INFORMATION: This sequence may encompass 1-6 'Gly-Gly-Gly-
      Gly-Ser' repeating units

<400> SEQUENCE: 138

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 139
<211> LENGTH: 25
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(4)
<223> OTHER INFORMATION: Thr or Ser
<220> FEATURE:
<221> NAME/KEY: MISC_FEATURE
<222> LOCATION: (1)..(5)
<223> OTHER INFORMATION: This sequence may encompass 1-5 'Xaa-Xaa-Xaa-
      Xaa-Gly' repeating units.  See specification as filed for detailed
      description of substitutions and preferred embodiments
<220> FEATURE:
<221> NAME/KEY: MOD_RES
<222> LOCATION: (6)..(9)
<223> OTHER INFORMATION: Thr or Ser
<220> FEATURE:
<221> NAME/KEY: MOD_RES
<222> LOCATION: (11)..(14)
<223> OTHER INFORMATION: Thr or Ser
<220> FEATURE:
<221> NAME/KEY: MOD_RES
<222> LOCATION: (16)..(19)
<223> OTHER INFORMATION: Thr or Ser
<220> FEATURE:
<221> NAME/KEY: MOD_RES
<222> LOCATION: (21)..(24)
<223> OTHER INFORMATION: Thr or Ser

<400> SEQUENCE: 139

Xaa Xaa Xaa Xaa Gly Xaa Xaa Xaa Xaa Gly Xaa Xaa Xaa Xaa Gly Xaa
1               5                   10                  15

Xaa Xaa Xaa Gly Xaa Xaa Xaa Xaa Gly
            20                  25

<210> SEQ ID NO 140
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ser Ser Ser Ser Gly
1               5
```

CONJUGATES OF GLP-1 AGONISTS AND USES THEREOF

CROSS-REFERENCE TO RELATED APPLICATIONS

This application is the U.S. national stage filing under 35 U.S.C. §371 of international application PCT/CA2009/001476, filed Oct. 15, 2009, which claims benefit of the filing date of U.S. Provisional Application No. 61/105,618, filed Oct. 15, 2008, each of which is incorporated by reference.

BACKGROUND OF THE INVENTION

The invention relates to compounds including a GLP-1 agonist (e.g., exendin-4), bound to a peptide vector and uses thereof. Such uses include the treatment, prevention, and reduction of metabolic disorders including diabetes and obesity.

As the levels of blood glucose rise postprandially, insulin is secreted and stimulates cells of the peripheral tissues (skeletal muscles and fat) to actively take up glucose from the blood as a source of energy. Loss of glucose homeostasis as a result of faulty insulin secretion or action typically results in metabolic disorders such as diabetes, which may be co-triggered or further exacerbated by obesity. Because these conditions are often fatal, strategies to restore adequate glucose clearance from the bloodstream are required.

Although diabetes may arise secondary to any condition that causes extensive damage to the pancreas (e.g., pancreatitis, tumors, administration of certain drugs such as corticosteroids or pentamidine, iron overload (e.g., hemochromatosis), acquired or genetic endocrinopathies, and surgical excision), the most common forms of diabetes typically arise from primary disorders of the insulin signaling system. There are two major types of diabetes, namely type 1 diabetes (also known as insulin dependent diabetes (IDDM)) and type 2 diabetes (also known as insulin independent or non-insulin dependent diabetes (NIDDM)), which share common long-term complications in spite of their different pathogenic mechanisms.

Type 1 diabetes, which accounts for approximately 10% of all cases of primary diabetes, is an organ-specific autoimmune disease characterized by the extensive destruction of the insulin-producing beta cells of the pancreas. The consequent reduction in insulin production inevitably leads to the deregulation of glucose metabolism. While the administration of insulin provides significant benefits to patients suffering from this condition, the short serum half-life of insulin is a major impediment to the maintenance of normoglycemia. An alternative treatment is islet transplantation, but this strategy has been associated with limited success.

Type 2 diabetes, which affects a larger proportion of the population, is characterized by a deregulation in the secretion of insulin and/or a decreased response of peripheral tissues to insulin, i.e., insulin resistance. While the pathogenesis of type 2 diabetes remains unclear, epidemiologic studies suggest that this form of diabetes results from a collection of multiple genetic defects or polymorphisms, each contributing its own predisposing risks and modified by environmental factors, including excess weight, diet, inactivity, drugs, and excess alcohol consumption. Although various therapeutic treatments are available for the management of type 2 diabetes, they are associated with various debilitating side effects. Accordingly, patients diagnosed with or at risk of having type 2 diabetes are often advised to adopt a healthier lifestyle, including loss of weight, change in diet, exercise, and moderate alcohol intake. Such lifestyle changes, however, are not sufficient to reverse the vascular and organ damages caused by diabetes.

Given that the strategies currently available for the management of metabolic disorders such as diabetes are suboptimal, there is a compelling need for treatments that are more effective and are not associated with such debilitating side effects.

SUMMARY OF THE INVENTION

We have developed compounds that include a GLP-1 agonist (e.g., exendin-4) and a peptide vector. These compounds are useful in treating metabolic disorders such as diabetes and obesity. The peptide vector is capable of transporting the GLP-1 agonist either across the blood-brain barrier (BBB) or into a particular cell type (e.g., liver, lung, kidney, spleen, and muscle). Because the conjugates are targeted across the BBB or to particular cell types, therapeutic efficacy can be achieved using lower doses or less frequent dosings as compared to unconjugated GLP-1 agonists, thus reducing the severity of or incidence of side effects and/or increasing efficacy. The conjugate may also exhibit increased stability, improved pharmacokinetics, or reduced degradation in vivo.

Accordingly, in a first aspect the invention features a compound having the formula:

A-X-B where A is a peptide vector capable of being transported across the blood-brain barrier (BBB) or into a particular cell type (e.g., liver, lung, kidney, spleen, and muscle), X is a linker, and B is a GLP-1 agonist (e.g., any described herein such as a peptide agonist). The transport across the BBB or into the cell may be increased by at least 10%, 25%, 50%, 75%, 100%, 200%, 500%, 750%, 1000%, 1500%, 2000%, 5000%, or 10,000%. The compound may be substantially pure. The compound may be formulated with a pharmaceutically acceptable carrier (e.g., any described herein).

In another aspect, the invention features methods of making the compound A-X-B. In one embodiment, the method includes conjugating the peptide vector (A) to a linker (X), and conjugating the peptide vector-linker (A-X) to a GLP-1 agonist (B), thereby forming the compound A-X-B. In another embodiment, the method includes conjugating the GLP-1 agonist (B) to a linker (X), and conjugating the GLP-1 agonist/linker (X-B) to a peptide vector (A), thereby forming the compound A-X-B. In another embodiment, the method includes conjugating the peptide vector (A) to a GLP-1 agonist (B), where either A or B optionally include a linker (X), to form the compound A-X-B.

In another aspect, the invention features a nucleic acid molecule that encodes the compound A-X-B, where the compound is a polypeptide. The nucleic acid molecule may be operably linked to a promoter and may be part of a nucleic acid vector. The vector may be in a cell, such as a prokaryotic cell (e.g., bacterial cell) or eukaryotic cell (e.g., yeast or mammalian cell, such as a human cell).

In another aspect, the invention features methods of making a compound of the formula A-X-B, where A-X-B is a polypeptide. In one embodiment, the method includes expressing a nucleic acid vector of the previous aspect in a cell to produce the polypeptide; and purifying the polypeptide.

In another aspect, the invention features a method of treating (e.g., prophylactically) a subject having a metabolic disorder. The method includes administering a compound of the first aspect in an amount sufficient to treat the disorder. The metabolic disorder may be diabetes (e.g., Type I or Type II), obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, a cardiovascular disease, or hypertension.

In another aspect, the invention features a method of reducing food intake by, or reducing body weight of, a subject. The method includes administering a compound of the first aspect to a subject in an amount sufficient to reduce food intake or reduce body weight. The subject may be overweight, obese, or bulimic.

In another aspect, the invention features a method of treating (e.g., prophylactically) a disorder selected from the group consisting of anxiety, movement disorder, aggression, psychosis, seizures, panic attacks, hysteria, sleep disorders, Alzheimer's disease, and Parkinson's disease. The method includes administering a compound of the first aspect to a subject in an amount sufficient to treat or prevent the disorder.

The invention also features a method of increasing neurogenesis in a subject. The method includes administering a compound of the first aspect to a subject. The subject may desire, or may be in need of neurogenesis. In certain embodiments, the subject may be suffering from a disease or disorder of the central nervous system such as Parkinson's Disease, Alzheimer's Disease, Huntington's Disease, ALS, stroke, ADD, and neuropsychiatric syndromes. In other embodiments, the increase in neurogenesis can improve learning or enhance neuroprotection.

In another aspect, the invention features a method for converting liver stem/progenitor cells into functional pancreatic cells; preventing beta-cell deterioration and stimulation of beta-cell proliferation; treating obesity; suppressing appetite and inducing satiety; treating irritable bowel syndrome; reducing the morbidity and/or mortality associated with myocardial infarction and stroke; treating acute coronary syndrome characterized by an absence of Q-wave myocardial infarction; attenuating post-surgical catabolic changes; treating hibernating myocardium or diabetic cardiomyopathy; suppressing plasma blood levels of norepinepherine; increasing urinary sodium excretion, decreasing urinary potassium concentration; treating conditions or disorders associated with toxic hypervolemia, e.g., renal failure, congestive heart failure, nephrotic syndrome, cirrhosis, pulmonary edema, and hypertension; inducing an inotropic response and increasing cardiac contractility; treating polycystic ovary syndrome; treating respiratory distress; improving nutrition via a non-alimentary route, i.e., via intravenous, subcutaneous, intramuscular, peritoneal, or other injection or infusion; treating nephropathy; treating left ventricular systolic dysfunction (e.g., with abnormal left ventricular ejection fraction); inhibiting antro-duodenal motility (e.g., for the treatment or prevention of gastrointestinal disorders such as diarrhea, postoperative dumping syndrome and irritable bowel syndrome, and as premedication in endoscopic procedures; treating critical illness polyneuropathy (CIPN) and systemic inflammatory response syndrome (SIRS; modulating triglyceride levels and treating dyslipidemia; treating organ tissue injury caused by reperfusion of blood flow following ischemia; or treating coronary heart disease risk factor (CHDRF) syndrome in a subject by administering and effective amount of a GLP-1 agonist.

In another aspect, the invention features a method of increasing GLP-1 receptor activity in a subject. The method includes administering a compound of the first aspect to a subject in an amount sufficient to increase GLP-1 receptor activity. The method may reduce glucose levels in a subject.

In any of the methods involving administration of a compound to a subject, the amount sufficient may be less than 90%, 75%, 50%, 40%, 30%, 20%, 15%, 10%, 5%, 4%, 3%, 2%, 1%, or 0.1% of the amount required for an equivalent dose of the GLP-1 agonist when not conjugated to the peptide vector. The amount sufficient may reduce side effects (e.g., vomiting, nausea, or diarrhea) as compared to administration of an effective amount of the GLP-1 agonist when not conjugated to the peptide vector. The subject may be a mammal such as a human.

In any of the above aspects, the peptide vector may be a polypeptide substantially identical to any of the sequences set Table 1, or a fragment thereof. In certain embodiments, the vector polypeptide has a sequence of Angiopep-1 (SEQ ID NO:67), Angiopep-2 (SEQ ID NO:97), Angiopep-3 (SEQ ID NO:107), Angiopep-4-a (SEQ ID NO:108), Angiopep-4-b (SEQ ID NO:109), Angiopep-5 (SEQ ID NO:110), Angiopep-6 (SEQ ID NO:111), or Angiopep-7 (SEQ ID NO:112)). The peptide vector or conjugate may be efficiently transported into a particular cell type (e.g., any one, two, three, four, or five of liver, lung, kidney, spleen, and muscle) or may cross the mammalian BBB efficiently (e.g., Angiopep-1, -2, -3, -4-a, -4-b, -5, and -6). In another embodiment, the peptide vector or conjugate is able to enter a particular cell type (e.g., any one, two, three, four, or five of liver, lung, kidney, spleen, and muscle) but does not cross the BBB efficiently (e.g., a conjugate including Angiopep-7). The peptide vector may be of any length, for example, at least 6, 7, 8, 9, 10, 11, 12, 13, 14, 15, 16, 17, 18, 19, 20, 21, 25, 35, 50, 75, 100, 200, or 500 amino acids, or any range between these numbers. In certain embodiments, the peptide vector is 10 to 50 amino acids in length. The polypeptide may be produced by recombinant genetic technology or chemical synthesis.

TABLE 1

Exemplary Polypeptides

| SEQ ID NO: | | | | | | | | | | | | | | | | | | |
|---|---|---|---|---|---|---|---|---|---|---|---|---|---|---|---|---|---|---|
| 1 | T | F | V | Y | G | G | C | R | A | K | R | N | N | F | K | S | A | E | D |
| 2 | T | F | Q | Y | G | G | C | M | G | N | G | N | N | F | V | T | E | K | E |
| 3 | P | F | F | Y | G | G | C | G | G | N | R | N | N | F | D | T | E | E | Y |
| 4 | S | F | Y | Y | G | G | C | L | G | N | K | N | N | Y | L | R | E | E | E |
| 5 | T | F | F | Y | G | G | C | R | A | K | R | N | N | F | K | R | A | K | Y |
| 6 | T | F | F | Y | G | G | C | R | G | K | R | N | N | F | K | R | A | K | Y |
| 7 | T | F | F | Y | G | G | C | R | A | K | K | N | N | Y | K | R | A | K | Y |
| 8 | T | F | F | Y | G | G | C | R | G | K | K | N | N | F | K | R | A | K | Y |
| 9 | T | F | Q | Y | G | G | C | R | A | K | R | N | N | F | K | R | A | K | Y |
| 10 | T | F | Q | Y | G | G | C | R | G | K | K | N | N | F | K | R | A | K | Y |
| 11 | T | F | F | Y | G | G | C | L | G | K | R | N | N | F | K | R | A | K | Y |
| 12 | T | F | F | Y | G | G | S | L | G | K | R | N | N | F | K | R | A | K | Y |
| 13 | P | F | F | Y | G | G | C | G | G | K | K | N | N | F | K | R | A | K | Y |
| 14 | T | F | F | Y | G | G | C | R | G | K | G | N | N | Y | K | R | A | K | Y |
| 15 | P | F | F | Y | G | G | C | R | G | K | R | N | N | F | L | R | A | K | Y |
| 16 | T | F | F | Y | G | G | C | R | G | K | R | N | N | F | K | R | E | K | Y |

TABLE 1-continued

Exemplary Polypeptides

| SEQ ID NO: | Sequence |
|---|---|
| 17 | P F F Y G G C R A K K N N F K R A K E |
| 18 | T F F Y G G C R G K R N N F K R A K D |
| 19 | T F F Y G G C R A K R N N F D R A K Y |
| 20 | T F F Y G G C R G K K N N F K R A E Y |
| 21 | P F F Y G G C G A N R N N F K R A K Y |
| 22 | T F F Y G G C G G K K N N F K T A K Y |
| 23 | T F F Y G G C R G N R N N F L R A K Y |
| 24 | T F F Y G G C R G N R N N F K T A K Y |
| 25 | T F F Y G G S R G N R N N F K T A K Y |
| 26 | T F F Y G G C L G N G N N F K R A K Y |
| 27 | T F F Y G G C L G N R N N F L R A K Y |
| 28 | T F F Y G G C L G N R N N F K T A K Y |
| 29 | T F F Y G G C R G N G N N F K S A K Y |
| 30 | T F F Y G G C R G K K N N F D R E K Y |
| 31 | T F F Y G G C R G K R N N F L R E K E |
| 32 | T F F Y G G C R G K G N N F D R A K Y |
| 33 | T F F Y G G S R G K G N N F D R A K Y |
| 34 | T F F Y G G C R G N G N N F V T A K Y |
| 35 | P F F Y G G C G G K G N N Y V T A K Y |
| 36 | T F F Y G G C L G K G N N F L T A K Y |
| 37 | S F F Y G G C L G N K N N F L T A K Y |
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G N R N N F K T E E Y |
| 49 | T F F Y G G C R G K R N N F K T E E D |
| 50 | P F F Y G G C G G N G N N F V R E K Y |
| 51 | S F F Y G G C M G N G N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |
| 68 | K F F Y G G C R G K R N N F K T E E Y |
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | T F F Y G G C R G K R N N F K T E E Y C |
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |
| 77 | T F F Y G G K R G K R N N F K T E E Y |
| 78 | T F F Y G G C R G K R N N F K T K R Y |
| 79 | T F F Y G G K R G K R N N F K T A E Y |
| 80 | T F F Y G G K R G K R N N F K T A G Y |
| 81 | T F F Y G G K R G K R N N F K R E K Y |
| 82 | T F F Y G G K R G K R N N F K R A K Y |
| 83 | T F F Y G G C L G N R N N F K T E E Y |
| 84 | T F F Y G C R G K R N N F K T E E Y |
| 85 | T F F Y G G R C G K R N N F K T E E Y |
| 86 | T F F Y G G C L G N G N N F D T E E E |
| 87 | T F Q Y G G C R G K R N N F K T E E Y |
| 88 | Y N K E F G T F N T K G C E R G Y R F |
| 89 | R F K Y G G C L G N M N N F E T L E E |
| 90 | R F K Y G G C L G N K N N F L R L K Y |

TABLE 1-continued

Exemplary Polypeptides

| SEQ ID NO: | |
|---|---|
| 91 | R F K Y G G C L G N K N N Y L R L K Y |
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R R F |
| 96 | R Q I K I W F Q N R R M K W K K |
| 97 | T F F Y G G S R G K R N N F K T E E Y |
| 98 | M R P D F C L E P P Y T G P C V A R I I R Y F Y N A K A G L C Q T F V Y G G C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F E S A E D C M R T C G G A |
| 103 | Y G G C R A K R N N F K S A E D C M R T C G G A |
| 104 | G L C Q T F V Y G G C R A K R N N F K S A E |
| 105 | L C Q T F V Y G G C E A K R N N F K S A |
| 107 | T F F Y G G S R G K R N N F K T E E Y |
| 108 | R F F Y G G S R G K R N N F K T E E Y |
| 109 | R F F Y G G S R G K R N N F K T E E Y |
| 110 | R F F Y G G S R G K R N N F R T E E Y |
| 111 | T F F Y G G S R G K R N N F R T E E Y |
| 112 | T F F Y G G S R G R R N N F R T E E Y |
| 113 | C T F F Y G G S R G K R N N F K T E E Y |
| 114 | T F F Y G G S R G K R N N F K T E E Y C |
| 115 | C T F F Y G G S R G R R N N F R T E E Y |
| 116 | T F F Y G G S R G R R N N F R T E E Y C |

Polypeptides Nos. 5, 67, 76, and 91, include the sequences of SEQ ID NOS: 5, 67, 76, and 91, respectively, and are amidated at the C-terminus.
Polypeptides Nos. 107, 109, and 110 include the sequences of SEQ ID NOS: 97, 109, and 110, respectively, and are acetylated at the N-terminus.

In any of the above aspects, the peptide vector may include an amino acid sequence having the formula:

X1-X2-X3-X4-X5-X6-X7-X8-X9-X10-X11-X12-X13-X14-X15-X16-X17-X18-X19 where each of X1-X19 (e.g., X1-X6, X8, X9, X11-X14, and X16-X19) is, independently, any amino acid (e.g., a naturally occurring amino acid such as Ala, Arg, Asn, Asp, Cys, Gln, Glu, Gly, His, Ile, Leu, Lys, Met, Phe, Pro, Ser, Thr, Trp, Tyr, and Val) or absent and at least one (e.g., 2 or 3) of X1, X10, and X15 is arginine. In some embodiments, X7 is Ser or Cys; or X10 and X15 each are independently Arg or Lys. In some embodiments, the residues from X1 through X19, inclusive, are substantially identical to any of the amino acid sequences of any one of SEQ ID NOS:1-105 and 107-116 (e.g., Angiopep-1, Angiopep-2, Angiopep-3, Angiopep-4-a, Angiopep-4-b, Angiopep-5, Angiopep-6, and Angiopep-7). In some embodiments, at least one (e.g., 2, 3, 4, or 5) of the amino acids X1-X19 is Arg. In some embodiments, the polypeptide has one or more additional cysteine residues at the N-terminal of the polypeptide, the C-terminal of the polypeptide, or both.

In any of the above aspects, the GLP-1 agonist may be a peptide agonist. The GLP-1 agonist may GLP-1, exendin-4, exendin-3, or analog or fragment thereof (e.g., any analog or fragment described herein). In particular embodiments, the GLP-1 agonist is an exendin-4 analog selected from the group consisting of [Lys$^{39}$]exendin-4 and [Cys$^{32}$]exendin-4.

In certain embodiments of any of the above aspects, the peptide vector or peptide GLP-1 agonist is modified (e.g., as described herein). The polypeptide may be amidated, acetylated, or both. Such modifications to polypeptides may be at the amino or carboxy terminus of the polypeptide. The polypeptide may also include peptidomimetics (e.g., those described herein) of any of the polypeptides described herein. The polypeptide may be in a multimeric form, for example, dimeric form (e.g., formed by disulfide bonding through cysteine residues).

In certain embodiments, the polypeptide has an amino acid sequence described herein with at least one amino acid substitution (e.g., 2, 3, 4, 5, 6, 7, 8, 9, 10, 11, or 12 substitutions), insertion, or deletion. The polypeptide may contain, for example, 1 to 12, 1 to 10, 1 to 5, or 1 to 3 amino acid substitutions, for example, 1 to 10 (e.g., to 9, 8, 7, 6, 5, 4, 3, 2) amino acid substitutions. The amino acid substitution(s) may be conservative or non-conservative. For example, the peptide vector may have an arginine at one, two, or three of the positions corresponding to positions 1, 10, and 15 of the amino acid sequence of any of SEQ ID NO:1, Angiopep-1, Angiopep-2, Angiopep-3, Angiopep-4-a, Angiopep-4-b, Angiopep-5, Angiopep-6, and Angiopep-7. The GLP-1 agonist may have a cysteine or lysine substitution or addition at any position (e.g., a lysine substitution at the N- or C-terminal position, or a cysteine substitution at the position corresponding to amino acid 32 of the exendin-4 sequence).

In any of the above aspects, the compound may specifically exclude a polypeptide including or consisting of any of SEQ ID NOS:1-105 and 107-116 (e.g., Angiopep-1, Angiopep-2, Angiopep-3, Angiopep-4-a, Angiopep-4-b, Angiopep-5, Angiopep-6, and Angiopep-7). In some embodiments, the polypeptides and conjugates of the invention exclude the polypeptides of SEQ ID NOs:102, 103, 104, and 105.

In any of the above aspects, the linker (X) may be any linker known in the art or described herein. In particular embodiments, the linker is a covalent bond (e.g., a peptide bond), a chemical linking agent (e.g., those described herein), an amino acid or a peptide (e.g., 2, 3, 4, 5, 8, 10, or more amino acids). In certain embodiments, the linker has the formula:

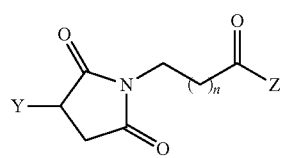

where n is an integer between 2 and 15 (e.g., 2, 3, 4, 5, 6, 7, 8, 9, 10, 11, 12, 13, 14, or 15); and either Y is a thiol on A and Z is a primary amine on B or Y is a thiol on B and Z is a primary amino on A.

By "GLP-1 agonist" is meant any compound capable of activating a GLP-1 receptor (e.g., a mammalian or human GLP-1 receptor). Agonists can include peptides or small molecule compounds (e.g., any of those described herein). Assays for determining whether a particular compound is a GLP-1 agonist are known in the art and described herein.

By "peptide vector" is meant a compound or molecule such as a polypeptide or a polypeptide mimetic that can be transported into a particular cell type (e.g., liver, lungs, kidney, spleen, or muscle) or across the BBB. The vector may be attached to (covalently or not) or conjugated to an agent (e.g., a GLP-1 agonist) and thereby may be able to transport the agent into a particular cell type or across the BBB. In certain embodiments, the vector may bind to receptors present on cancer cells or brain endothelial cells and thereby be transported into the cancer cell or across the BBB by transcytosis. The vector may be a molecule for which high levels of transendothelial transport may be obtained, without affecting the cell or BBB integrity. The vector may be a polypeptide or a peptidomimetic and may be naturally occurring or produced by chemical synthesis or recombinant genetic technology.

By "substantially identical" is meant a polypeptide or nucleic acid exhibiting at least 35%, 40%, 50%, 55%, 60%, 65%, 70%, 75%, 85%, 90%, 95%, or even 99% identity to a reference amino acid or nucleic acid sequence. For polypeptides, the length of comparison sequences will generally be at least 4 (e.g., at least 5, 6, 7, 8, 9, 10, 11, 12, 13, 14, 15, 16, 17, 18, 19, 20, 25, 50, or 100) amino acids. For nucleic acids, the length of comparison sequences will generally be at least 60 nucleotides, preferably at least 90 nucleotides, and more preferably at least 120 nucleotides, or full length. It is to be understood herein that gaps may be found between the amino acids of an analogs that are identical or similar to amino acids of the original polypeptide. The gaps may include no amino acids, one or more amino acids that are not identical or similar to the original polypeptide. Biologically active analogs of the vectors (polypeptides) of the invention are encompassed herewith. Percent identity may be determined, for example, with n algorithm GAP, BESTFIT, or FASTA in the Wisconsin Genetics Software Package Release 7.0, using default gap weights.

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence of (e.g., preventing) a disease, disorder or condition or reducing the severity of the disease, disorder, or condition by administering a therapeutic agent to the subject.

A subject who is being treated for a metabolic disorder is one who a medical practitioner has diagnosed as having such a condition. Diagnosis may be performed by any suitable means, such as those described herein. A subject in whom the development of diabetes or obesity is being prevented may or may not have received such a diagnosis. One in the art will understand that subject of the invention may have been subjected to standard tests or may have been identified, without examination, as one at high risk due to the presence of one or more risk factors, such as family history, obesity, particular ethnicity (e.g., African Americans and Hispanic Americans), gestational diabetes or delivering a baby that weighs more than nine pounds, hypertension, having a pathological condition predisposing to obesity or diabetes, high blood levels of triglycerides, high blood levels of cholesterol, presence of molecular markers (e.g., presence of autoantibodies), and age (over 45 years of age). An individual is considered obese when their weight is 20% (25% in women) or more over the maximum weight desirable for their height. An adult who is more than 100 pounds overweight, is considered to be morbidly obese. Obesity is also defined as a body mass index (BMI) over 30 kg/m$^2$.

By "a metabolic disorder" is meant any pathological condition resulting from an alteration in a subject's metabolism. Such disorders include those resulting from an alteration in glucose homeostasis resulting, for example, in hyperglycemia. According to this invention, an alteration in glucose levels is typically an increase in glucose levels by at least 5%, 10%, 20%, 30%, 40%, 50%, 60%, 70%, 80%, 90%, or even 100% relative to such levels in a healthy individual. Metabolic disorders include obesity and diabetes (e.g., diabetes type I, diabetes type II, MODY, and gestational diabetes), satiety, and endocrine deficiencies of aging.

By "reducing glucose levels" is meant reducing the level of glucose by at least 10%, 20%, 30%, 40%, 50%, 60%, 70%, 80%, 90%, 95%, or 100% relative to an untreated control. Desirably, glucose levels are reduced to normoglycemic levels, i.e., between 150 to 60 mg/dL, between 140 to 70 mg/dL, between 130 to 70 mg/dL, between 125 to 80 mg/dL, and preferably between 120 to 80 mg/dL. Such reduction in glucose levels may be obtained by increasing any one of the biological activities associated with the clearance of glucose from the blood (e.g., increase insulin production, secretion, or action).

By "subject" is meant a human or non-human animal (e.g., a mammal).

By "increasing GLP-1 receptor activity" is meant increasing the level of receptor activation measured using standard techniques (e.g., cAMP activation) by, for example, at least %, 20%, 50%, 75%, 100%, 200%, or 500% as compared to an untreated control.

By "equivalent dosage" is meant the amount of a compound of the invention required to achieve the same molar amount of the GLP-1 agonist in the compound, as compared to the unconjugated GLP-1 agonist. For example, the equivalent dosage of 1.0 µg exendin-4 is about 1.6 µg of the [Lys$^{39}$-MHA]exendin-4/Angiopep-2-Cys-NH$_2$ conjugate described herein.

By a polypeptide which is "efficiently transported across the BBB" is meant a polypeptide that is able to cross the BBB at least as efficiently as Angiopep-6 (i.e., greater than 38.5% that of Angiopep-1 (250 nM) in the in situ brain perfusion assay described in U.S. patent application Ser. No. 11/807, 597, filed May 29, 2007, hereby incorporated by reference). Accordingly, a polypeptide which is "not efficiently transported across the BBB" is transported to the brain at lower levels (e.g., transported less efficiently than Angiopep-6).

By a polypeptide or compound which is "efficiently transported to a particular cell type" is meant that the polypeptide or compound is able to accumulate (e.g., either due to increased transport into the cell, decreased efflux from the cell, or a combination thereof) in that cell type to at least a 10% (e.g., 25%, 50%, 100%, 200%, 500%, 1,000%, 5,000%, or 10,000%) greater extent than either a control substance, or, in the case of a conjugate, as compared to the unconjugated agent. Such activities are described in detail in International application Publication No. WO 2007/009229, hereby incorporated by reference.

Other features and advantages of the invention will be apparent from the following Detailed Description, the drawings, and the claims.

DETAILED DESCRIPTION

Figure 1:
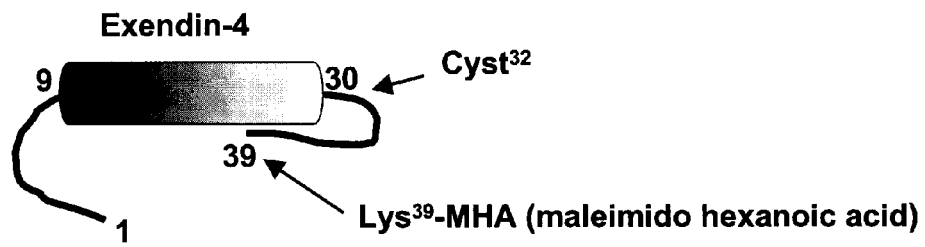
FIG. 1 is table and schematic diagram showing exendin-4 (SEQ ID NO:120) and the exendin-4 analogs (SEQ ID NOS: 117 and 118) used in experiments described herein.

We have developed GLP-1 agonist/peptide conjugates having an enhanced ability to cross the blood-brain barrier (BBB) or to enter particular cell type(s) (e.g., liver, lung, kidney, spleen, and muscle) using the exemplary GLP-1 agonist exendin-4 and exendin-4 analogs. The peptide conjugates of the invention can include a GLP-1 agonist and a peptide vector that enhance transport across the BBB.

We have also shown that lower doses of the compounds of the invention, as compared to unconjugated GLP-1 agonists, are effective in treating GLP-1 related disorders including a reduction in glycemia. By administering lower doses of the conjugated peptides, side effects such as vomiting, nausea, and diarrhea observed with the unconjugated agonists can be reduced or eliminated. Alternatively, increased efficacy at higher doses may be obtained.

The GLP-1 agonist can be any GLP-1 agonist known in the art and including peptides such as those described below. Particular GLP-1 agonists include exendin-4, GLP-1, and exendin-3 fragments, substitutions (e.g., conservative or non-conservative substitutions, or substitutions of non-naturally occurring amino acids), and chemical modifications to the amino acid sequences (e.g., those described herein). Particular GLP-1 agonists are described in detail below.

GLP-1 Agonists

The conjugates of the invention can include any GLP-1 agonist known in the art. Particular GLP-1 agonists include GLP-1, exendin-4, and analogs thereof. Exemplary analogs are described below.

Exendin-4 and Exendin-4 Analogs

Exendin-4 and exendin-4 analogs can also be used in the compositions, methods, and kits of the invention. The compounds of the invention can include fragments of the exendin-4 sequence. Exendin-4 has the sequence.

```
                                    (SEQ ID NO: 120)
His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser-NH2
```

Particular exendin-4 analogs include those having a cysteine substitution (e.g., [Cys$^{32}$]exendin-4) or a lysine substitution (e.g., [Lys$^{39}$]exendin-4).

Exendin analogs are also described in U.S. Pat. No. 7,157,555 and include those of the formula:

```
                                    (SEQ ID NO: 121)
X1-X2-X3-Gly-Thr-X4-X5-X6-X7-X8-Ser-Lys-Gln-X9-Glu-

Glu-Glu-Ala-Val-Arg-Leu-X10-X11-X12-X13-Leu-Lys-

Asn-Gly-Gly-X14-Ser-Ser-Gly-Ala-X15-X16-X17-X18-Z
``` where $X_1$ is His, Arg or Tyr; $X_2$ is Ser, Gly, Ala or Thr; $X_3$ is Asp or Glu; $X_4$ is Phe, Tyr or Nal; $X_5$ is Thr or Ser; $X_6$ is Ser or Thr; $X_7$ is Asp or Glu; $X_8$ is Leu, Ile, Val, pGly or Met; $X_9$ is Leu, Ile, pGly, Val or Met; $X_{10}$ is Phe, Tyr, or Nal; $X_{11}$ is Ile, Val, Leu, pGly, t-BuG or Met; $X_{12}$ is Glu or Asp; $X_{13}$ is Trp, Phe, Tyr, or Nal; $X_{14}$, $X_{15}$, $X_{16}$ and $X_{17}$ are independently Pro, HPro, 3Hyp, 4Hyp, TPro, N-alkylglycine, N-alkyl-pGly, or N-alkylalanine; $X_{18}$ is Ser, Thr, or Tyr; and Z is —OH or —NH$_2$ (e.g., with the proviso that the compound is not exendin-3 or exendin-4).

Preferred N-alkyl groups for N-alkylglycine, N-alkyl-pGly and N-alkylalanine include lower alkyl groups (e.g., $C_{1-6}$ alkyl or $C_{1-4}$ alkyl).

In certain embodiments, $X_1$ is His or Tyr (e.g., His). $X_2$ can be Gly. $X_9$ can be Leu, pGly, or Met. $X_{13}$ can be Trp or Phe. $X_4$ can be Phe or Nal; $X_{11}$ can be Ile or Val, and $X_{14}$, $X_{15}$, $X_{16}$ and $X_{17}$ can be independently selected from Pro, HPro, TPro, or N-alkylalanine (e.g., where N-alkylalanine has a N-alkyl group of 1 to about 6 carbon atoms). In one aspect, X15, X16, and X17 are the same amino acid residue. X18 may be Ser or Tyr (e.g., Ser). Z can be —NH$_2$.

In other embodiments, $X_1$ is His or Tyr (e.g., His); $X_2$ is Gly; $X_4$ is Phe or Nal; $X_9$ is Leu, pGly, or Met; $X_{10}$ is Phe or Nal; $X_{11}$ is Ile or Val; $X_{14}$, $X_{15}$, $X_{16}$, and $X_{17}$ are independently selected from Pro, HPro, TPro, or N-alkylalanine; and $X_{18}$ is Ser or Tyr, (e.g., Ser). Z can be —NH$_2$.

In other embodiments, $X_1$ is His or Arg; $X_2$ is Gly; $X_3$ is Asp or Glu; $X_4$ is Phe or napthylalanine; $X_5$ is Thr or Ser; $X_6$ is Ser or Thr; $X_7$ is Asp or Glu; $X_8$ is Leu or pGly; $X_9$ is Leu or pGly; $X_{10}$ is Phe or Nal; $X_{11}$ is Ile, Val, or t-butyltylglycine; $X_{12}$ is Glu or Asp; $X_{13}$ is Trp or Phe; $X_{14}$, $X_{15}$, $X_{16}$, and $X_{17}$ are independently Pro, HPro, TPro, or N-methylalanine; $X_{18}$ is Ser or Tyr: and Z is —OH or —NH$_2$ (e.g., where the compound is not exendin-3 or exendin-4). Z can be —NH$_2$.

In another embodiment, $X_9$ is Leu, Ile, Val, or pGly (e.g., Leu or pGly) and $X_{13}$ is Phe, Tyr, or Nal (e.g., Phe or Nal). These compounds can exhibit advantageous duration of action and be less subject to oxidative degradation, both in vitro and in vivo, as well as during synthesis of the compound.

Other exendin analogs also described in U.S. Pat. Nos. 7,157,555 and 7,223,725, include compounds of the formula:

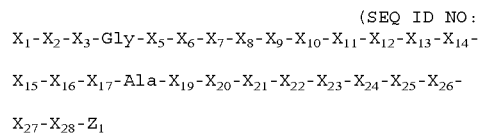
(SEQ ID NO: 122)

where $X_1$ is His, Arg, or Tyr; $X_2$ is Ser, Gly, Ala, or Thr; $X_3$ is Asp or Glu; $X_5$ is Ala or Thr; $X_6$ is Ala, Phe, Tyr, or Nal; $X_7$ is Thr or Ser; $X_8$ is Ala, Ser, or Thr; $X_9$ is Asp or Glu; $X_{10}$ is Ala, Leu, Ile, Val, pGly, or Met; $X_{11}$ is Ala or Ser; $X_{12}$ is Ala or Lys; $X_{13}$ is Ala or Gln; $X_{14}$ is Ala, Leu, Ile, pGly, Val, or Met; $X_{15}$ is Ala or Glu; $X_{16}$ is Ala or Glu; $X_{17}$ is Ala or Glu; $X_{19}$ is Ala or Val; $X_{20}$ is Ala or Arg; $X_{21}$ is Ala or Leu; $X_{22}$ is Phe, Tyr, or Nal; $X_{23}$ is Ile, Val, Leu, pGly, t-BuG, or Met; $X_{24}$ is Ala, Glu, or Asp; $X_{25}$ is Ala, Trp, Phe, Tyr, or Nal; $X_{26}$ is Ala or Leu; $X_{27}$ is Ala or Lys; $X_{28}$ is Ala or Asn; $Z_1$ is —OH, —NH$_2$, Gly-Z$_2$, Gly-Gly-Z$_2$, Gly-Gly-X$_{31}$-Z$_2$, Gly-Gly-X$_{31}$-Ser-Z$_2$, Gly-Gly-X$_{31}$-Ser-Ser-Z$_2$, Gly-Gly-X$_{31}$-Ser-Ser-Gly-Z$_2$, Gly-Gly-X$_{31}$-Ser-Ser-Gly-Ala-Z$_2$, Gly-Gly-X$_{31}$-Ser-Ser-Gly-Ala-X$_{36}$-Z$_2$, Gly-Gly-X$_{31}$-Ser-Ser-Gly-Ala-X$_{36}$-X$_{37}$-Z$_2$ or Gly-Gly-X$_{31}$-Ser-Ser-Gly-Ala-X$_{36}$-X$_{37}$-X$_{38}$-Z$_2$; X$_{31}$, X$_{36}$, X$_{37}$, and X$_{38}$ are independently Pro, HPro, 3Hyp, 4Hyp, TPro, N-alkylglycine, N-alkyl-pGly or N-alkylalanine; and $Z_2$ is —OH or —NH$_2$ (e.g., provided that no more than three of X$_5$, X$_6$, X$_8$, X$_{10}$, X$_{11}$, X$_{12}$, X$_{13}$, X$_{14}$, X$_{15}$, X$_{16}$, X$_{17}$, X$_{19}$, X$_{20}$, X$_{21}$, X$_{24}$, X$_{25}$, X$_{26}$, X$_{27}$ and X$_{28}$ are Ala). Preferred N-alkyl groups for N-alkylglycine, N-alkyl-pGly and N-alkylalanine include lower alkyl groups of 1 to about 6 carbon atoms (e.g., 1 to 4 carbon atoms).

In certain embodiments, $X_1$ is His or Tyr (e.g., His). $X_2$ can be Gly. $X_{14}$ can be Leu, pGly, or Met. $X_{25}$ can be Trp or Phe. In some embodiments, $X_6$ is Phe or Nal, $X_{22}$ is Phe or Nal, and $X_{23}$ is Ile or Val. $X_{31}$, $X_{36}$, $X_{37}$, and $X_{38}$ can be independently selected from Pro, HPro, TPro, and N-alkylalanine. In certain embodiments, $Z_1$ is —NH$_2$ or $Z_2$ is —NH$_2$.

In another embodiment, $X_1$ is His or Tyr (e.g., His); $X_2$ is Gly; $X_6$ is Phe or Nal; $X_{14}$ is Leu, pGly, or Met; $X_{22}$ is Phe or Nal; $X_{23}$ is Ile or Val; $X_{31}$, $X_{36}$, $X_{37}$, and $X_{38}$ are independently selected from Pro, HPro, TPro, or N-alkylalanine. In particular embodiments, $Z_1$ is —NH$_2$.

In another embodiment, $X_1$ is His or Arg; $X_2$ is Gly or Ala; $X_3$ is Asp or Glu; $X_5$ is Ala or Thr; $X_6$ is Ala, Phe, or naphthylalanine; $X_7$ is Thr or Ser; $X_8$ is Ala, Ser, or Thr; $X_9$ is Asp or Glu; $X_{10}$ is Ala, Leu, or pGly; $X_{11}$ is Ala or Ser; $X_{12}$ is Ala or Lys; $X_{13}$ is Ala or Gln; $X_{14}$ is Ala, Leu, or pGly; $X_{15}$ is Ala or Glu; $X_{16}$ is Ala or Glu; $X_{17}$ is Ala or Glu; $X_{19}$ is Ala or Val; $X_{20}$ is Ala or Arg; $X_{21}$ is Ala or Leu; $X_{22}$ is Phe or Nal; $X_{23}$ is Ile, Val or t-BuG; $X_{24}$ is Ala, Glu or Asp; $X_{25}$ is Ala, Trp or Phe; $X_{26}$ is Ala or Leu; $X_{27}$ is Ala or Lys; $X_{28}$ is Ala or Asn; $Z_1$ is —OH, —NH$_2$, Gly-Z$_2$, Gly-Gly-Z$_2$, Gly-Gly-X$_{31}$-Z$_2$, Gly-Gly X$_{31}$-Ser-Z$_2$, Gly-Gly-X$_{31}$ Ser-Ser-Z$_2$, Gly-Gly-X$_{31}$ Ser-Ser-Gly-Z$_2$, Gly-Gly-X$_{31}$ Ser-Ser-Gly Ala-Z$_2$, Gly-Gly-X$_{31}$ Ser-Ser-Gly-Ala-X$_{36}$-Z$_2$, Gly-Gly-X$_{31}$-Ser-Ser-Gly-Ala-X$_{36}$-X$_{37}$-Z$_2$, Gly-Gly-X$_{31}$-Ser-Ser-Gly-Ala-X$_{36}$-X$_{37}$-X$_{38}$-Z$_2$; X$_{31}$, X$_{36}$, X$_{37}$ and X$_{38}$ being independently Pro HPro, TPro or N-methylalanine; and $Z_2$ being —OH or —NH$_2$ (e.g., provided that no more than three of X$_3$, X$_5$, X$_6$, X$_8$, X$_{10}$, X$_{11}$, X$_{12}$, X$_{13}$, X$_{14}$, X$_{15}$, X$_{16}$, X$_{17}$, X$_{19}$, X$_{20}$, X$_{21}$, X$_{24}$, X$_{25}$, X$_{26}$, X$_{27}$ and X$_{28}$ are Ala).

In yet another embodiment, $X_{14}$ is Leu, Ile, Val, or pGly (e.g., Leu or pGly), and $X_{25}$ is Phe, Tyr or Nal (e.g., Phe or Nal).

Exendin analogs described in U.S. Pat. No. 7,220,721 include compounds of the formula:

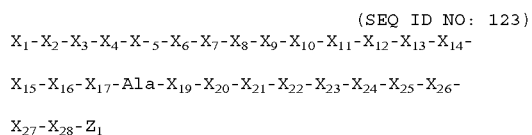
(SEQ ID NO: 123)

where $X_1$ is His, Arg, Tyr, Ala, Norval, Val, or Norleu; $X_2$ is Ser, Gly, Ala, or Thr; $X_3$ is Ala, Asp, or Glu; $X_4$ is Ala, Norval, Val, Norleu, or Gly; $X_5$ is Ala or Thr; $X_6$ is Phe, Tyr or Nal; $X_7$ is Thr or Ser; $X_8$ is Ala, Ser or Thr; $X_9$ is Ala, Norval, Val, Norleu, Asp, or Glu; $X_{10}$ is Ala, Leu, Ile, Val, pGly, or Met; $X_{11}$ is Ala or Ser; $X_{12}$ is Ala or Lys; $X_{13}$ is Ala or Gln; $X_{14}$ is Ala, Leu, Ile, pGly, Val, or Met; $X_{15}$ is Ala or Glu; $X_{16}$ is Ala or Glu; $X_{17}$ is Ala or Glu; $X_{19}$ is Ala or Val; $X_{20}$ is Ala or Arg; $X_{21}$ is Ala or Leu; $X_{22}$ is Phe, Tyr, or Nal; $X_{23}$ is Ile, Val, Leu, pGly, t-BuG, or Met; $X_{24}$ is Ala, Glu, or Asp; $X_{25}$ is Ala, Trp, Phe, Tyr, or Nal; $X_{26}$ is Ala or Leu; $X_{27}$ is Ala or Lys; $X_{28}$ is Ala or Asn; $Z_1$ is —OH, —NH$_2$, Gly-Z$_2$, Gly-Gly-Z$_2$, Gly-Gly-X$_{31}$-Z$_2$, Gly-Gly-X$_{31}$-Ser-Z$_2$, Gly-Gly-X$_{31}$-Ser-Ser-Z$_2$, Gly-Gly-X$_{31}$-Ser-Ser-Gly-Z$_2$, Gly-Gly-X$_{31}$ Ser-Ser-Gly-Ala-Z$_2$, Gly-Gly-X$_{31}$-Ser-Ser-Gly-Ala-X$_{13}$-Z$_2$, Gly-Gly-X$_{31}$ Ser-Ser-Gly-Ala-X$_{36}$-X$_{37}$-Z$_2$, Gly-Gly X$_{31}$ Ser Ser Gly Ala X$_{36}$ X$_{37}$ X$_{31}$-Z$_2$ or Gly Gly X$_{31}$ Ser Ser Gly Ala X$_{36}$ X$_{37}$ X$_{38}$ X$_{39}$-Z$_2$; where X$_{31}$, X$_{36}$, X$_{37}$, and X$_{38}$ are independently Pro, HPro, 3Hyp, 4Hyp, TPro, N-alkylglycine, N-alkyl-pGly, or N-alkylalanine; and $Z_2$ is —OH or —NH$_2$ (e.g., provided that no more than three of X$_3$, X$_4$, X$_5$, X$_8$, X$_9$, X$_{10}$, X$_{11}$, X$_{12}$, X$_{13}$, X$_{14}$, X$_{15}$, X$_{16}$, X$_{17}$, X$_{19}$, X$_{20}$, X$_{21}$, X$_{24}$, X$_{25}$, X$_{26}$, X$_{27}$ and X$_{28}$ are Ala and/or provided also that, if X$_1$ is His, Arg, or Tyr, then at least one of X$_3$, X$_4$ and X$_9$ is Ala).

Particular examples of exendin-4 analogs include exendin-4(1-30), exendin-4(1-30) amide, exendin-4(1-28) amide, [Leu$^{14}$,Phe$^{25}$]exendin-4 amide, [Leu$^{14}$,Phe$^{25}$]exendin-4(1-28) amide, and [Leu$^{14}$,Ala$^{22}$,Phe$^{25}$]exendin-4(1-28) amide.

U.S. Pat. No. 7,329,646 describes exendin-4 analogs having the general formula:

(SEQ ID NO: 124)
His-Gly-Glu-Gly-Thr-Phe-Thr-Ser-Asp-Leu-Ser-Lys-

Gln-$X_{14}$-Glu-Glu-Glu-Ala-Val-$X_{20}$-Leu-Phe-Ile-Glu-

Trp-Leu-Lys-Asn-Gly-Gly-Pro-Ser-Ser-Gly-Ala-Pro-

Pro-Pro-Ser-$X_{40}$.

where $X_{14}$ is Arg, Leu, Ile, or Met; $X_{20}$ is His, Arg, or Lys; $X_{40}$ is Arg-OH, —OH, —NH$_2$ or Lys-OH. In certain embodiments, when $X_{14}$ is Met and $X_{20}$ is Arg, $X_{40}$ cannot be —NH$_2$. Other exendin-4 derivatives include [(Ile/Leu/Met)$^{14}$,(His/Lys)$^{20}$,Arg$^{40}$]exendin-4; [(not Lys/not Arg)$^{12}$, (not Lys/not Arg)$^{20}$, (not Lys/not Arg)$^{27}$,Arg$^{40}$]exendin-4; and [(not Lys/not Arg)$^{20}$,Arg$^{40}$]exendin-4. Particular exendin-4 analogs include [Lys$^{20}$,Arg$^{40}$]exendin-4,[His$^{20}$,Arg$^{40}$]exendin-4; and [Leu$^{14}$,Lys$^{20}$,Arg$^{40}$]exendin-4.

The invention may also use truncated forms of exendin-4 or any of the exendin analogs described herein. The truncated forms may include deletions of 1, 2, 3, 4, 5, 6, 7, 8, 9, 10, 11, 12, 13, 14, 15, 16, 17, 18, 19, or 20 amino acids from the N-terminus, from the C-terminus, or a combination thereof. Particular exendin-4 fragments include Exendin-4(1-31). Other fragments of exendin-4 are described in U.S. Patent Application Publication No. 2007/0037747 and have the formula:

(SEQ ID NO: 125)
His-Gly-Glu-Gly-Thr-$X_6$-Thr-Ser-Asp-Leu-Ser-Lys-

Gln-$X_{14}$-Glu-Glu-Glu-Ala-Val-$X_{20}$-Leu-Phe-Ile-Glu-

Trp-Leu-Lys-Asn-Gly-$X_{30}$-Pro-$X_{32}$ where $X_6$ is Phe or Tyr, $X_{14}$ is Met, Ile or Leu, $X_{20}$ is Lys; $X_{30}$ is Gly or is absent; and $X_{32}$ is Arg or is absent.

GLP-1 and GLP-1 Analogs

The GLP-1 agonist used in the compositions, methods, and kits of the invention can be GLP-1 or a GLP-1 analog. In certain embodiments, the GLP-1 analog is a peptide, which can be truncated, may have one or more substitutions of the wild type sequence (e.g., the human wild type sequence), or may have other chemical modifications. GLP-1 agonists can also be non-peptide compounds, for example, as described in U.S. Pat. No. 6,927,214. Particular analogs include LY548806, CJC-1131, and Liraglutide.

The GLP-1 analog can be truncated form of GLP-1. The GLP-1 peptide may be truncated by 1, 2, 3, 4, 5, 6, 7, 8, 9, 10, 11, 12, 13, 15, 20, or more residues from its N-terminus, its C-terminus, or a combination thereof. In certain embodiments, the truncated GLP-1 analog is the GLP-1 (7-34), GLP-1 (7-35), GLP-1 (7-36), or GLP-1 (7-37) human peptide or the C-terminal amidated forms thereof.

In other embodiments of the invention, modified forms of truncated GLP-1 peptides are used. Exemplary analogs are described in U.S. Pat. No. 5,545,618 and have the amino acid sequence:

(SEQ ID NO: 126)
His-Ala-Glu-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-Lys-(Gly)-(Arg)-(Gly)

where (Gly), (Arg), and (Gly) are present or absent depending on indicated chain length, with at least one modification selected from the group consisting of (a) substitution of a neutral amino acid, Arg, or a D form of Lys for Lys at position 26 and/or 34 and/or a neutral amino acid, Lys, or a D form of Arg for Arg at position 36; (b) substitution of an oxidation-resistant amino acid for Trp at position 31; (c) substitution according to at least one of: Tyr for Val at position 16; Lys for Ser at position 18; Asp for Glu at position 21; Ser for Gly at position 22; Arg for Gln at position 23; Arg for Ala at position 24; and Gln for Lys at position 26; (d) a substitution comprising at least one of an alternative small neutral amino acid for Ala at position 8; an alternative acidic amino acid or neutral amino acid for Glu at position 9; an alternative neutral amino acid for Gly at position 10; and an alternative acidic amino acid for Asp at position 15; and (e) substitution of an alternative neutral amino acid or the Asp or N-acylated or alkylated form of His for His at position 7. With respect to modifications (a), (b), (d), and (e), the substituted amino acids may be in the D form. The amino acids substituted at position 7 can also be the N-acylated or N-alkylated amino acids. Exemplary GLP-1 analogs include [D-His$^7$]GLP-1(7-37), [Tyr$^7$]GLP-1(7-37), [N-acetyl-His$^7$]GLP-1(7-37), [N-isopropyl-His$^7$]GLP-1(7-37), [D-Ala$^8$]GLP-1(7-37), [D-Glu$^9$]GLP-1(7-37), [Asp$^9$]GLP-1(7-37), [D-Asp$^9$]GLP-1(7-37), [D-Phe$^{10}$]GLP-1(7-37), [Ser$^{22}$,Arg$^{23}$,Arg$^{24}$,Gln$^{26}$] GLP-1 (7-37), and [Ser$^8$,Gln$^9$,Tyr$^{16}$,Lys$^{18}$,Asp$^{21}$] GLP-1(7-37).

Other GLP-1 fragments are described in U.S. Pat. No. 5,574,008 have the formula:

(SEQ ID NO: 127)
$R_1$-Ser-Tyr-Leu-Glu-Gly-Gln-Ala-Ala-Lys-Glu-Phe-

Ile-Ala-Trp-Leu-Val-X-Gly-Arg-$R_2$ where $R_1$ is H$_2$N; H$_2$N-Ser; H$_2$N-Val-Ser; H$_2$N-Asp-Val-Ser; H$_2$N-Ser-Asp-Val-Ser; H$_2$N-Thr-Ser-Asp-Val-Ser; H$_2$N-Phe-Thr-Ser-Asp-Val-Ser; H$_2$N-Thr-Phe-Thr-Ser-Asp-Val-Ser; H$_2$N-Gly-Thr-Phe-Thr-Ser-Asp-Val-Ser; H$_2$N-Glu-Gly-Thr-Phe-Thr-Ser-Asp-Val-Ser; or H$_2$N-Ala-Glu-Gly-Thr-Phe-Thr-Ser-Asp-Val-Ser; X is Lys or Arg; and $R_2$ is NH$_2$, OH, Gly-NH$_2$, or Gly-OH.

Other GLP-1 analogs, described in U.S. Pat. No. 5,118,666, include the sequence His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-X, where X is Lys, Lys-Gly, or Lys-Gly-Arg (SEQ ID NO:128).

GLP-1 analogs also include peptides of the formula: H$_2$N—X—CO—$R_1$, where $R_1$ is OH, OM, or —NR$_2$R$_3$; M is a pharmaceutically acceptable cation or a lower branched or unbranched alkyl group (e.g., C$_{1-6}$ alkyl); R$_2$ and R$_3$ are independently selected from the group consisting of hydrogen and a lower branched or unbranched alkyl group (e.g., C$_{1-6}$ alkyl); X is a peptide comprising the sequence His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQ ID NO:129); NH$_2$ is the amine group of the amino terminus of X; and CO is the carbonyl group of the carboxy terminus of X; acid addition salts thereof; and the protected or partially protected derivatives thereof. These compounds may have insulinotropic activity exceeding that of GLP-1(1-36) or GLP-1(1-37).

Other GLP-1 analogs are described in U.S. Pat. No. 5,981,488 and have the formula:

(SEQ ID NO: 130)
$R_1$-X-Glu-Gly-Thr-Phe-Thr-Ser-Asp-Val-Ser-Ser-Tyr-

Leu-Y-Gly-Gln-Ala-Ala-Lys-Z-Phe-Ile-Ala-Trp-Leu-

Val-Lys-Gly-Arg-$R_2$ where $R_1$ is His, D-His, desamino-His, 2-amino-His, β-hydroxy-His, homohistidine, α-fluoromethyl-His, or α-methyl-His; X is Met, Asp, Lys, Thr, Leu, Asn, Gln, Phe, Val, or Tyr; Y and Z are independently selected from Glu, Gln, Ala, Thr, Ser, and Gly; and $R_2$ is selected from $NH_2$ and Gly-OH (e.g., provided that, if $R_1$ is His, X is Val, Y is Glu, and Z is Glu, then $R_2$ is $NH_2$).

Other GLP-1 analogs are described in U.S. Pat. No. 5,512,549 and have the formula:

(SEQ ID NO: 131)
$R_1$-Ala-Glu-Gly-Thr-Phe-Thr-Ser-Asp-Val-Ser-Ser-

Tyr-Leu-Glu-Gly-Gln-Ala-Ala-Xaa-Glu-Phe-Ile-Ala-

Trp-Leu-Val-Lys($R_2$)-Gly-Arg-$R_3$ where $R_1$ is 4-imidazopropionyl (des-amino-histidyl), 4-imidazoacetyl, or 4-imidazo-α, αdimethyl-acetyl; $R_2$, which is bound to the side chain of the Lys (e.g., through the ε amino group), is $C_{6-10}$ unbranched acyl or is absent; $R_3$ is Gly-OH or $NH_2$; and Xaa is Lys or Arg.

Still other GLP-1 analogs are described in U.S. Pat. No. 7,084,243. In one embodiment, the GLP-1 analog has the formula:

(SEQ ID NO: 132)
His-$X_8$-Glu-Gly-$X_{11}$-$X_{12}$-Thr-Ser-Asp-$X_{16}$-Ser-Ser-

Tyr-Leu-Glu-$X_{22}$-$X_{23}$-$X_{24}$-Ala-$X_{26}$-$X_{27}$-Phe-Ile-Ala- $X_{31}$-Leu-$X_{33}$-$X_{34}$-$X_{35}$-$X_{36}$-R where $X_8$ is Gly, Ala, Val, Leu, Ile, Ser, or Thr; $X_{11}$ is Asp, Glu, Arg, Thr, Ala, Lys, or His; $X_{12}$ is His, Trp, Phe, or Tyr; $X_{16}$ is Leu, Ser, Thr, Trp, His, Phe, Asp, Val, Tyr, Glu, or Ala; $X_{22}$ is Gly, Asp, Glu, Gln, Asn, Lys, Arg, Cys, or Cya; $X_{23}$ is His, Asp, Lys, Glu, or Gln; $X_{24}$ is Glu, His, Ala, or Lys; $X_{26}$ is Asp, Lys, Glu, or His; $X_{27}$ is Ala, Glu, His, Phe, Tyr, Trp, Arg, or Lys; $X_{30}$ is Ala, Glu, Asp, Ser, or His; $X_{33}$ is Asp, Arg, Val, Lys, Ala, Gly, or Glu; $X_{34}$ is Glu, Lys, or Asp; $X_{35}$ is Thr, Ser, Lys, Arg, Trp, Tyr, Phe, Asp, Gly, Pro, His, or Glu; $X_{36}$ is Arg, Glu, or His; R is Lys, Arg, Thr, Ser, Glu, Asp, Trp, Tyr, Phe, His, —$NH_2$, Gly, Gly-Pro, or Gly-Pro-$NH_2$, or is deleted (e.g., provided that the polypeptide does not have the sequence of GLP-1(7-37)OH or GLP-1(7-36)—$NH_2$ and provided that the polypeptide is not $Gly^8$-GLP-1(7-37)OH, $Gly^8$-GLP-1(7-36)$NH_2$, $Val^8$-GLP-1(7-37)OH, $Val^8$-GLP-1(7-36)$NH_2$, $Leu^8$-GLP-1(7-37)OH, $Leu^8$-GLP-1(7-36)$NH_2$, $Ile^8$-GLP-1 (7-37)OH, $Ile^x$-GLP-1 (7-36)$NH_2$, $Ser^8$-GLP-1(7-37)OH, $Ser^8$-GLP-1(7-36)$NH_2$, $Thr^8$-GLP-1 (7-37)OH, or $Thr^8$-GLP-1 (7-36)$NH_2$, $Ala^{11}$-Glp-1(7-37)OH, $Ala^{11}$-Glp-1(7-36)$NH_2$, $Ala^{16}$-Glp-1 (7-37)OH, $Ala^{16}$-Glp-1 (7-36) $NH_2$, $Ala^{27}$-Glp-1(7-37)OH, $Ala^{27}$-Glp-1(7-36)$NH_2$, $Ala^{27}$-Glp-1(7-37)OH, $Ala^{27}$-Glp-1(7-36)$NH_2$, $Ala^{33}$-Glp-1(7-37)OH, or $Ala^{33}$-Glp-1(7-36)$NH_2$).

In another embodiment, the polypeptide has the amino acid sequence:

(SEQ ID NO: 133)
His-$X_8$-Glu-Gly-Thr-$X_{12}$-Thr-Ser-Asp-$X_{16}$-Ser-Ser-

Tyr-Leu-Glu-$X_{22}$-$X_{23}$-Ala-Ala-$X_{26}$-Glu-Phe-Ile-$X_{30}$-

Trp-Leu-Val-Lys-$X_{35}$-Arg-R where $X_8$ is Gly, Ala, Val, Leu, Ile, Ser, or Thr; $X_{12}$ is His, Trp, Phe, or Tyr; $X_{16}$ is Leu, Ser, Thr, Trp, His, Phe, Asp, Val, Glu, or Ala; $X_{22}$ is Gly, Asp, Glu, Gln, Asn, Lys, Arg, Cys, or Cya; $X_{23}$ is His, Asp, Lys, Glu, or Gln; $X_{26}$ is Asp, Lys, Glu, or His; $X_{30}$ is Ala, Glu, Asp, Ser, or His; $X_{35}$ is Thr, Ser, Lys, Arg, Trp, Tyr, Phe, Asp, Gly, Pro, His, or Glu; R is Lys, Arg, Thr, Ser, Glu, Asp, Trp, Tyr, Phe, His, —$NH_2$, Gly, Gly-Pro, Gly-Pro-$NH_2$, or is deleted, (e.g., provided that the polypeptide does not have the sequence of GLP-1(7-37)OH or GLP-1(7-36)-$NH_2$ and provided that the polypeptide is not $Gly^8$-GLP-1(7-37)OH, $Gly^8$-GLP-1(7-36)$NH_2$, $Val^8$-GLP-1(7-37)OH, $Val^8$-GLP-1(7-36)$NH_2$, $Leu^8$-GLP-1(7-37)OH, $Leu^8$-GLP-1(7-36)$NH_2$, $Ile^x$-GLP-1(7-37)OH, $Ile^8$-GLP-1(7-36)$NH_2$, $Ser^8$-GLP-1(7-37)OH, $Ser^8$-GLP-1(7-36)$NH_2$, $Thr^8$-GLP-1(7-37)OH, $Thr^8$-GLP-1(7-36)$NH_2$, $Ala^{16}$-GLP(7-37)OH, or $Ala^{16}$-GLP-1(7-36)$NH_2$).

In another embodiment, the polypeptide has the amino acid sequence:

(SEQ ID NO: 134)
His-$X_8$-Glu-Gly-Thr-Phe-Thr-Ser-Asp-Val-Ser-Ser-

Tyr-Leu-Glu-$X_{22}$-$X_{23}$-Ala-Ala-Lys-$X_{27}$-Phe-Ile-$X_{30}$-

Trp-Leu-Val-Lys-Gly-Arg-R where $X_8$ is Gly, Ala, Val, Leu, Ile, Ser, or Thr; $X_{22}$ is Gly, Asp, Glu, Gln, Asn, Lys, Arg, Cys, or Cya; $X_{23}$ is His, Asp, Lys, Glu, or Gln; $X_{27}$ is Ala, Glu, His, Phe, Tyr, Trp, Arg, or Lys; $X_{30}$ is Ala, Glu, Asp, Ser, or His; R is Lys, Arg, Thr, Ser, Glu, Asp, Trp, Tyr, Phe, His, —$NH_2$, Gly, Gly-Pro, or Gly-Pro-$NH_2$, or is deleted (e.g., provided that the polypeptide does not have the sequence of GLP-1(7-37)OH or GLP-1(7-36) $NH_2$ and provided that the polypeptide is not $Gly^8$-GLP-1(7-37)OH, $Gly^8$-GLP-1(7-36)$NH_2$, $Val^8$-GLP-1(7-37)OH, $Val^8$-GLP-1(7-36)$NH_2$, $Leu^8$-GLP-1(7-37)OH, $Leu^8$-GLP-1(7-36)$NH_2$, $Ile^x$-GLP-1(7-37)OH, $Ile^x$-GLP-1(7-36)$NH_2$, $Ser^8$-GLP-1(7-37)OH, $Ser^b$-GLP-1(7-36)$NH_2$, $Thr^8$-GLP-1(7-37) OH, $Thr^8$-GLP-1(7-36)$NH_2$, $Ala^{16}$-GLP-1(7-37)OH, $Ala^{16}$-Glp-1(7-36) $NH_2$, $Glu^{27}$-Glp-1(7-37)OH, or $Glu^{27}$-Glp-1(7-36)$NH_2$.

In another embodiment, the polypeptide has the amino acid sequence:

(SEQ ID NO: 135)
$X_7$-$X_8$-Glu-Gly-Thr-Phe-Thr-Ser-Asp-Val-Ser-Ser-Tyr-

Leu-Glu-$X_{22}$-Gln-Ala-Ala-Lys-Glu-Phe-Ile-Ala-Trp-

Leu-Val-Lys-Gly-Arg-R where $X_7$ is L-His, D-His, desamino-His, 2-amino-His, β-hydroxy-His, homo-His, α-fluoromethyl-His or α-methyl-His; $X_8$ is Gly, Ala, Val, Leu, Ile, Ser or Thr (e.g., Gly, Val, Leu, Ile, Ser, or Thr); $X_{22}$ is Asp, Glu, Gln, Asn, Lys, Arg, Cys, or Cya, and R is —$NH_2$ or Gly(OH).

In another embodiment, the GLP-1 compound has an amino acid other than alanine at position 8 and an amino acid other than glycine at position 22. Specific examples of GLP-1 compounds include [$Glu^{22}$]GLP-1 (7-37)OH, [$Asp^{22}$]GLP-1 (7-37)OH, [$Arg^{22}$]GLP-1 (7-37)OH, [$Lys^{22}$]GLP-1 (7-37)OH, [$Cya^{22}$]GLP-1 (7-37)OH, [$Val^8$,$Glu^{22}$]GLP-1 (7-37)OH, [$Val^8$,$Asp^{22}$]GLP-1 (7-37)OH, [$Val^8$,$Arg^{22}$]GLP-1 (7-37)OH, [$Val^8$,$Lys^{22}$]GLP-1 (7-37)OH, [$Val^8$,$Cya^{22}$]GLP-1 (7-37)OH, [$Gly^8$,$Glu^{22}$]GLP-1 (7-37)OH, [$Gly^8$,$Asp^{22}$]GLP-1 (7-37)OH, [$Gly^8$,$Arg^{22}$]GLP-1 (7-37)OH, [$Gly^8$,$Lys^{22}$]GLP-1 (7-37)OH, [$Gly^8$,$Cya^{22}$]GLP-1 (7-37) OH, [$Glu^{22}$]GLP-1 (7-36)$NH_2$, [$Asp^{22}$]GLP-1 (7-36)$NH_2$, [$Arg^{22}$]GLP-1 (7-36)$NH_2$, [$Lys^{22}$]GLP-1 (7-36)$NH_2$, [$Cya^{22}$]GLP-1 (7-36)$NH_2$, [$Val^8$,$Glu^{22}$]GLP-1 (7-36)$NH_2$, [$Val^8$, Asp²²]GLP-1 (7-36)NH₂, [Val⁸,Arg²²]GLP-1 (7-36)NH₂, [Val⁸,Lys²²]GLP-1 (7-36)NH₂, [Val⁸,Cya²²]GLP-1 (7-36)NH₂, [Gly⁸,Glu²²]GLP-1 (7-36)NH₂, [Gly⁸,Asp²²]GLP-1 (7-36)NH₂, [Gly⁸,Arg²²]GLP-1 (7-36)NH₂, [Gly⁸,Lys²²]GLP-1 (7-36)NH₂, [Gly⁸, Cya²²]GLP-1 (7-36)NH₂, [Val⁸, Lys²³]GLP-1 (7-37)OH, [Val⁸,Ala²⁷]GLP-1 (7-37)OH, [Val⁸,Glu³⁰]GLP-1 (7-37)OH, [Gly⁸,Glu³⁰]GLP-1 (7-37) OH, [Val⁸,His³⁵]GLP-1 (7-37)OH, [Val⁸,His³⁷]GLP-1 (7-3) OH, [Val⁸,Glu²²,Lys²²]GLP-1 (7-37)OH, [Val⁸,Glu²²,Glu²] GLP-1 (7-37)OH, [Val⁸,Glu²²,Ala²⁷]GLP-1 (7-37)OH, [Val⁸,Gly³⁴,Lys³]GLP-1 (7-37)OH, [Val⁸,His³⁷]GLP-1 (7-37)OH, [Gly⁸,His³⁷]GLP-1 (7-37)OH.

Other GLP-1 analogs are described in U.S. Pat. No. 7,101, 843 and include those having the formula:

(SEQ ID NO: 136)
X₇-X₈-Glu-Gly-Thr-X₁₂-Thr-Ser-Asp-X₁₆-Ser-X₁₈-X₁₉-

X₂₀-Glu-X₂₂-Gln-Ala-X₂₅-Lys-X₂₇-Phe-Ile-X₃₀-Trp-

Leu-X₃₃-Lys-Gly-Arg-X₃₇ wherein: $X_7$ is L-His, D-His, desamino-His, 2-amino-His, β-hydroxy-His, homohistidine, α-fluoromethyl-His, or α-methyl-His; $X_8$ is Ala, Gly, Val, Leu, Ile, Ser, or Thr; $X_{12}$ is Phe, Trp, or Tyr; $X_{16}$ is Val, Trp, Ile, Leu, Phe, or Tyr; $X_{18}$ is Ser, Trp, Tyr, Phe, Lys, Ile, Leu, or Val; $X_{19}$ is Tyr, Trp, or Phe; $X_{20}$ is Leu, Phe, Tyr, or Trp; $X_{22}$ is Gly, Glu, Asp, or Lys; $X_{25}$ is Ala, Val, Ile, or Leu; $X_{27}$ is Glu, Ile, or Ala; $X_{30}$ is Ala or Glu $X_{33}$ is Val, or Ile; and $X_{37}$ is Gly, His, NH₂, or is absent (e.g., provided that the compound does not have the sequence GLP-1(7-37)OH, GLP-1(7-36)—NH₂, [Gly⁸]GLP-1(7-37)OH, [Gly⁸]GLP-1(7-36)NH₂, [Val⁸]GLP-1(7-37)OH, [Val⁸]GLP-1(7-36)NH₂, [Leu⁸]GLP-1(7-37)OH, [Leu⁸]GLP-1(7-36)NH₂, [Ile⁸]GLP-1(7-37)OH, [Val⁸]GLP-1(7-36)NH₂, [Ser⁸]GLP-1(7-37)OH, [Ser⁸]GLP-1(7-36)NH₂, [Thr⁸]GLP-1(7-37)OH, [Thr⁸]GLP-1(7-36)NH₂, [Val⁸,Tyr¹²]GLP-1(7-37)OH, [Val⁸,Tyr¹²]GLP-1(7-36)NH₂, [Val⁸,Tyr¹⁶]GLP-1(7-37)OH, [Val⁸,Tyr¹⁶]GLP-1(7-36)NH₂, [Val⁸,Glu²²]GLP-1(7-37)OH, [Val⁸,Glu²²]GLP-1(7-36) NH₂, [Gly⁸,Glu²¹]GLP-1(7-37)OH, [Gly⁸,Glu²²]GLP-1(7-36)NH₂, [Val⁸,Asp²¹]GLP-1(7-37)OH, [Val⁸,Asp²¹]GLP-1 (7-36)NH₂, [Gly⁸,Asp²²]GLP-1(7-37)OH, [Gly⁸,Asp²²] GLP-1(7-36)NH₂, [Val⁸,Lys²¹]GLP-1(7-37)OH, [Val⁸, Lys²²]GLP-1(7-36)NH₂, [Gly⁸,Lys²²]GLP-1(7-37)OH, [Gly⁸,Lys²²]GLP-1(7-36)NH₂, [Leu⁸,Glu²²]GLP-1(7-37) OH, [Leu⁸,Glu²²]GLP-1(7-36)NH₂, [Gly⁸,Glu²²]GLP-1(7-37)OH, [Gly⁸,Glu²²]GLP-1(7-36)NH₂, [Leu⁸,Asp²¹]GLP-1 (7-37)OH, [Leu⁸,Asp²²]GLP-1(7-36)NH₂, [Gly⁸,Asp²²] GLP-1(7-37)OH, [Gly⁸,Asp²²]GLP-1(7-36)NH₂, [Leu⁸, Lys²²]GLP-1(7-37)OH, [Leu⁸,Lys²²]GLP-1(7-36)NH₂, [Ile⁸,Lys²²]GLP-1(7-37)OH, [Ile⁸,Lys²²]GLP-1(7-36)NH₂, [Ser⁸,Glu²¹]GLP-1(7-37)OH, [Ser⁸,Glu²²]GLP-1(7-36) NH₂, [Thr⁸,Glu²¹]GLP-1(7-37)OH, [Thr⁸,Glu²²]GLP-1(7-36)NH₂, [Ser⁸,Asp²¹]GLP-1(7-37)OH, [Ser⁸,Asp²¹]GLP-1 (7-36)NH₂, [Thr⁸,Asp²²]GLP-1(7-37)OH, [Thr⁸,Asp²²] GLP-1(7-36)NH₂, [Ser⁸,Lys²²]GLP-1(7-37)OH, [Ser⁸, Lys²²]GLP-1(7-36)NH₂, [Thr⁸,Lys²¹]GLP-1(7-37)OH, [Thr⁸,Lys²²]GLP-1(7-36)NH₂, [Glu²¹]GLP-1(7-37)OH, [Glu²¹]GLP-1(7-36)NH₂, [Asp²¹]GLP-1(7-37)OH, [Asp²¹] GLP-1(7-36)NH₂, [Lys²²]GLP-1(7-37)OH, [Lys²²]GLP-1 (7-36)NH₂, [Val⁸,Ala²⁷]GLP-1(7-37)OH, [Val⁸,Glu²², Ala²⁷]GLP-1(7-37)OH, [Val⁸,Glu³¹]GLP-1(7-37)OH, [Val⁸, Glu³¹]GLP-1(7-36)NH₂, [Gly⁸,Glu³]GLP-1(7-37)OH, [Gly⁸,Glu³]GLP-1(7-36)NH₂, [Leu⁸,Glu³]GLP-1(7-37)OH, [Leu⁸,Glu³]GLP-1(7-36)NH₂, [Ile⁸,Glu³]GLP-1(7-37)OH, [Leu⁸,Glu³¹]GLP-1(7-36)NH₂, [Ser⁸,Glu³]GLP-1(7-37) OH, [Ser⁸,Glu³]GLP-1(7-36)NH₂, [Thr⁸,Glu³]GLP-1(7-37) OH, [Thr⁸,Glu³]GLP-1(7-36)NH₂, [Val⁸,His³⁷]GLP-1(7-37) OH, [Val⁸,His³¹]GLP-1(7-36)NH₂, [Gly⁸,His³]GLP-1(7-37) OH, [Gly⁸,His³⁸]GLP-1(7-36)NH₂, [Leu⁸,His³⁷]GLP-1(7-37)OH, [Leu⁸,His³⁷]GLP-1(7-36)NH₂, [Ile⁸,His³¹]GLP-1 (7-37)OH, [Ile⁸,His³⁷]GLP-1(7-36)NH₂, [Ser⁸,His³⁷]GLP-1 (7-37)OH, [Ser⁸,His³⁷]GLP-1(7-36)NH₂, [Thr⁸,His³⁷]GLP-1(7-37)OH, [Thr⁸,His37]GLP-1(7-36)NH₂).

Other GLP-1 analogs described in U.S. Pat. No. 7,101,843 have the formula:

(SEQ ID NO: 137)
X₇-X₈-Glu-Gly-Thr-Phe-Thr-Ser-Asp-X₁₆-Ser-X₁₈-Tyr-

Leu-Glu-X₂₂-Gln-Ala-X₂₅-Lys-Glu-Phe-Ile-Ala-Trp-

Leu-X₃₃-Lys-Gly-Arg-X₃₇ wherein: $X_7$ is L-His, D-His, desamino-His, 2-amino-His, β-hydroxy-His, homohistidine, α-fluoromethyl-His, or α-methyl-His; $X_8$ is Gly, Ala, Val, Leu, Ile, Ser, or Thr; $X_{16}$ is Val, Phe, Tyr, or Trp; $X_{18}$ is Ser, Tyr, Trp, Phe, Lys, Ile, Leu, or Val; $X_{22}$ is Gly, Glu, Asp, or Lys; $X_{25}$ is Ala, Val, Ile, or Leu; $X_{33}$ is Val or Ile; and $X_{37}$ is Gly, NH₂, or is absent (e.g., provided that the GLP-1 compound does not have the sequence of GLP-1(7-37)OH, GLP-1(7-36)-NH₂, [Gly⁸]GLP-1(7-37)OH, [Gly⁸]GLP-1(7-36)NH₂, [Val⁸]GLP-1(7-37)OH, [Val⁸]GLP-1(7-36)NH₂, [Leu⁸]GLP-1(7-37)OH, [Leu⁸]GLP-1(7-36)NH₂, [Ile⁸]GLP-1(7-37)OH, [Ile⁸]GLP-1(7-36)NH₂, [Ser⁸]GLP-1(7-37)OH, [Ser⁸]GLP-1(7-36) NH₂, [Thr⁸]GLP-1(7-37)OH, [Thr⁸]GLP-1(7-36)NH₂, [Val⁸-Tyr¹⁶]GLP-1(7-37)OH, [Val⁸-Tyr¹⁶]GLP-1(7-36) NH₂, [Val⁸,Glu²²]GLP-1(7-37)OH, [Val⁸,Glu²²]GLP-1(7-36)NH₂, [Gly⁸,Glu²¹]GLP-1(7-37)OH, [Gly⁸,Glu²²]GLP-1 (7-36)NH₂, [Val⁸,Asp²¹]GLP-1(7-37)OH, [Val⁸,Asp²¹] GLP-1(7-36)NH₂, [Gly⁸,Asp²¹]GLP-1(7-37)OH, [Gly⁸, Asp²²]GLP-1(7-36)NH₂, [Val⁸,Lys²¹]GLP-1(7-37)OH, [Val⁸,Lys²¹]GLP-1(7-36)NH₂, [Gly⁸,Lys²¹]GLP-1(7-37) OH, [Gly⁸,Lys²¹]GLP-1(7-36)NH₂, [Leu⁸,Glu²²]GLP-1(7-37)OH, [Leu⁸,Glu²¹]GLP-1(7-36)NH₂, [Ile⁸,Glu²¹]GLP-1 (7-37)OH, [Ile⁸,Glu²¹]GLP-1(7-36)NH₂, [Leu⁸,Asp²¹] GLP1(7-37)OH, [Leu⁸,Asp²²]GLP-1(7-36)NH₂, [Ile⁸, Asp²²]GLP-1(7-37)OH, [Ile⁸,Asp²¹]GLP-1(7-36)NH₂, [Leu⁸,Lys²¹]GLP-1(7-37)OH, [Leu⁸,Lys²²]GLP-1(7-36) NH₂, [Ile⁸,Lys²²]GLP-1(7-37)OH, [Ile⁸,Lys²²]GLP-1(7-36) NH₂, [Ser⁸,Glu²¹]GLP-1(7-37)OH, [Ser⁸,Glu²¹]GLP-1(7-36)NH₂, [Thr⁸,Glu²¹]GLP-1(7-37)OH, [Thr⁸,Glu²¹]GLP-1 (7-36)NH₂, [Ser₈,Asp²¹]GLP-1(7-37)OH, [Ser⁸,Asp²¹] GLP-1(7-36)NH₂, [Thr⁸,Asp²²]GLP-1(7-37)OH, [Thr⁸, Asp²¹]GLP-1(7-36)NH₂, [Ser⁸,Lys²²]GLP-1(7-37)OH, [Ser⁸,Lys²¹]GLP-1(7-36)NH₂, [Thr⁸,Lys²²]GLP-1(7-37) OH, [Thr⁸,Lys²²]GLP-1(7-36)NH₂, [Glu²²]GLP-1(7-37) OH, [Glu²¹]GLP-1(7-36)NH₂, [Asp²¹]GLP-1(7-37)OH, [Asp²¹]GLP-1(7-36)NH₂, [Lys²¹]GLP-1(7-37)OH, [Lys21] GLP-1(7-36)NH₂).

GLP-1 analogs are also described in U.S. Pat. No. 7,238, 670 and have the structure:

A-X₁-X₂-X₃-X₄-X₅-X₆-X₇-X₈-X₉-Y-Z-B where each of $X_{1-9}$ is a naturally or nonnaturally occurring amino acid residue; Y and Z are amino acid residues; and one of the substitutions at the α-carbon atoms of Y and Z may each independently be substituted with a primary substituent group selected from the group consisting of hydrogen, alkyl, cycloalkyl, cycloalkylalkyl, heterocyclylalkyl, arylalkyl and heteroarylalkyl, heterocyclylalkyl said primary substituent optionally being substituted with a secondary substituent selected from a cycloalkyl, heterocyclyl, aryl, or heteroaryl group; any of said primary or secondary substituents may further be substituted with one or more of H, alkyl, cycloalkyl, arylalkyl, aryl, heterocyclyl, heteroaryl, alkenyl, alkynyl, halo, hydroxy, mercapto, nitro, cyano, amino, acylamino, azido, guanidino, amidino, carboxyl, carboxamido, carboxamido alkyl, formyl, acyl, carboxyl alkyl, alkoxy, aryloxy, arylalkyloxy, heteroaryloxy, heterocycleoxy, acyloxy, mercapto, mercapto alkyl, mercaptoaryl, mercapto acyl, halo, cyano, nitro, azido, amino, guanidino alkyl, guanidino acyl, sulfonic, sulfonamido, alkyl sulfonyl, aryl sulfonyl or phosphonic group; wherein, the primary or secondary substitutents may optionally be bridged by covalent bonds to form one or more fused cyclic or heterocyclic systems with each other; where, the other substitution at the alpha-carbon of Y may be substituted with H, $C_{1-6}$ alkyl, aminoalkyl, hydroxyalkyl or carboxyalkyl; where the other substitution at the alphα-carbon of Z may be substituted with hydrogen, $C_{1-12}$ alkyl, aminoalkyl, hydroxyalkyl, or carboxyalkyl;

A and B are optionally present, where A is present and A is H, an amino acid or peptide containing from about 1-15 amino acid residues, an R group, an R—C(O) (amide) group, a carbamate group RO—C(O), a urea $R_4R_5N$—C(O), a sulfonamido R—$SO_2$, or $R_4R_5N$—$SO_2$; where R is selected from the group consisting of hydrogen, $C_{1-12}$ alkyl, $C_{3-10}$ cycloalkyl, cycloalkylalkyl, heterocyclyl, heterocycloalkyl, aryl, heteroaryl, arylalkyl, aryloxyalkyl, heteroarylalkyl, and heteroaryloxyalkyl; $R_4$ and $R_5$ are each independently selected from the group consisting of H, alkyl, cycloalkyl, cycloalkylalkyl, heterocyclyl, heterocycloalkyl, aryl, heteroaryl, arylalkyl, aryloxyalkyl, heteroarylalkyl, and heteroaryloxyalky; where the α-amino group of $X_1$ is substituted with H or an alkyl group, said alkyl group may optionally form a ring with A; where B is present and B is $OR_1$, $NR_1R_2$, or an amino acid or peptide containing from 1 to 15 amino acid residues (e.g., 1 to 10 or 1 to 5) terminating at the C-terminus as a carboxamide, substituted carboxamide, an ester, a free carboxylic acid, or an amino-alcohol; where $R_1$ and $R_2$ are independently chosen from H, $C_{1-12}$ alkyl, $C_{3-10}$ cycloalkyl, cycloalkylalkyl, heterocyclyl, heterocycloalkyl, aryl, heteroaryl, arylalkyl, aryloxyalkyl, heteroarylalkyl or heteroaryloxyalkyl.

Exemplary substitutions on the α-carbon atoms of Y and Z include heteroarylarylmethyl, arylheteroarylmethyl, and biphenylmethyl forming biphenylalanine residues, any of which is also optionally substituted with one or more, hydrogen, alkyl, cycloalkyl, arylalkyl, aryl, heterocyclyl, heteroaryl, alkenyl, alkynyl, halo, hydroxy, mercapto, nitro, cyano, amino, acylamino, azido, guanidino, amidino, carboxyl, carboxamido, carboxamido alkyl, formyl, acyl, carboxyl alkyl, alkoxy, aryloxy, arylalkyloxy, heteroaryloxy, heterocycleoxy, acyloxy, mercapto, mercapto alkyl, mercaptoaryl, mercapto acyl, halo, cyano, nitro, azido, amino, guanidino alkyl, guanidino acyl, sulfonic, sulfonamido, alkyl sulfonyl, aryl sulfonyl and phosphonic group.

Other embodiments include isolated polypeptides where the other substitution at the α-carbon of Y is substituted with H, methyl, or ethyl; and where the other substitution at the α-carbon of Z is substituted with H, methyl, or ethyl.

Further embodiments include isolated polypeptides as described above where $X_1$ is naturally or non-naturally occurring amino acid residue in which one of the substitutions at the α-carbon is a primary substituent selected from the group consisting of heterocyclylalkyl, heteroaryl, heteroarylkalkyl and arylalkyl, said primary substituent optionally being substituted with secondary substituent selected from heteroaryl or heterocyclyl; and in which the other substitution at the α-carbon is H or alkyl; $X_2$ is naturally or normaturally occurring amino acid residue in which one of the substitutions at the α-carbon is an alkyl or cycloalkyl where the alkyl group may optionally form a ring with the nitrogen of $X_2$; and wherein the other substitution at the α-carbon is H or alkyl; $X_3$ is a naturally or normaturally occurring amino acid residue in which one of the substitutions at the α-carbon is a carboxyalkyl, bis-carboxyalkyl, sulfonylalkyl, heteroalkyl, or mercaptoalkyl; and where the other substitution at the α-carbon is hydrogen or alkyl; $X_4$ is a naturally or normaturally occurring amino acid residue in which the α-carbon is not substituted, or in which one of the substitutions at the α-carbon is aminoalkyl, carboxyalkyl heteroarylalkyl, or heterocycylalkyl; $X_5$ is a naturally or normaturally occurring amino acid residue in which one of the substitutions at the α-carbon is an alkyl or hydroxyalkyl, and in which the other substitution at the α-carbon is hydrogen or alkyl; $X_6$ is a naturally or normaturally occurring amino acid residue in which one of the substitutions at the α-carbon is $C_{1-12}$ alkyl, aryl, heteroaryl, heterocyclyl, cycloalkylalkyl, heterocyclylalkyl, arylalkyl, or heteroarylalkyl group, and the other substitution at the α-carbon is H or alkyl; $X_7$ is a naturally or normaturally occurring amino acid residue in which one of the substitutions at the α-carbon is a hydroxylalkyl group; $X_8$ is a naturally or normaturally occurring amino acid residue in which one of the substitutions at the α-carbon is $C_{1-12}$ alkyl, hydroxylalkyl, heteroarylalkyl, or carboxamidoalkyl, and the other substitution at the α-carbon is H or alkyl; $X_9$ is a naturally or normaturally occurring amino acid residue in which one of the substitutions at α-carbon is carboxylalkyl, bis-carboxylalkyl, carboxylaryl, sulfonylalkyl, carboxylamidoalkyl, or heteroarylalkyl; and where A is H, an amino acid or peptide containing from about 1 to about 5 amino acid residues, an R group, an R—C(O) amide group, a carbamate group RO—C(O), a urea $R_4R_5N$—C(O), a sulfonamido R—$SO_2$ or a $R_4R_5N$—$SO_2$.

In certain embodiments, $X_1$ is His, D-His, N-Methyl-His, D-N-Methyl-His, 4-ThiazolylAla, or D-4-ThiazolylAla; $X_2$ is Ala, D-Ala, Pro, Gly, D-Ser, D-Asn, Nma, D-Nma, 4-Thio-Pro, 4-Hyp, L-2-Pip, L-2-Azt, Aib, S- or R-Iva and Acc3; $X_3$ is Glu, N-Methyl-Glu, Asp, D-Asp, His, Gla, Adp, Cys, or 4-ThiazolyAla; $X_4$ is Gly, His, Lys, or Asp; $X_5$ is Thr, D-Thr, Nle, Met, Nva, or L-Aoc; $X_6$ is Phe, Tyr, Tyr(Bzl), Tyr(3-$NO_2$), Nle, Trp, Phe(penta-fluoro), D-Phe(penta-fluoro), Phe (2-fluoro), Phe(3-fluoro), Phe(4-fluoro), Phe(2,3-di-fluoro), Phe(3,4-di-fluoro), Phe(3,5-di-fluoro), Phe(2,6-di-fluoro), Phe(3,4,5-tri-fluoro), Phe(2-iodo), Phe(2-OH), Phe(2-OMe), Phe(3-OMe), Phe(3-cyano), Phe(2-chloro), Phe(2-$NH_2$), Phe(3-$NH_2$), Phe(4-$NH_2$), Phe(4-$NO_2$), Phe(4-Me), Phe(4-allyl), Phe(n-butyl), Phe(4-cyclohexyl), Phe(4-cyclohexyloxy), Phe (4-phenyloxy), 2-Nal, 2-pyridylAla, 4-thiazolylAla, 2-Thi, α-Me-Phe, D-α-Me-Phe, α-Et-Phe, D-α-Et-Phe, α-Me-Phe (2-fluoro), D-α-Me-Phe(2-fluoro), α-Me-Phe(2,3-di-fluoro), D-α-Me-Phe(2,3-di-fluoro), α-Me-Phe(2,6-di-fluoro), D-α-Me-Phe(2,6-di-fluoro), α-Me-Phe(penta-fluoro) and D-α-Me-Phe(penta-fluoro); $X_7$ is Thr, D-Thr, Ser, or hSer; $X_8$ is Ser, hSer, His, Asn, or α-Me-Ser; and $X_9$ is Asp, Glu, Gla, Adp, Asn, or His.

Additional embodiments include those where Y is Bip, D-Bip, L-Bip(2-Me), D-Bip(2-Me), L-Bip(2'-Me), L-Bip(2-Et), D-Bip(2-Et), L-Bip(3-Et), L-Bip(4-Et), L-Bip(2-n-propyl), L-Bip(2-n-propyl, 4-OMe), L-Bip(2-n-propyl,2'-Me), L-Bip(3-Me), L-Bip(4-Me), L-Bip(2,3-di-Me), L-Bip(2,4-di-Me), L-Bip(2,6-di-Me), L-Bip(2,4-di-Et), L-Bip(2-Me, 2'-Me), L-Bip(2-Et, 2'-Me), L-Bip(2-Et, 2'-Et), L-Bip(2-Me, 4-OMe), L-Bip(2-Et,4-OMe), D-Bip(2-Et,4-OMe), L-Bip(3-OMe), L-Bip(4-OMe), L-Bip(2,4,6-tri-Me), L-Bip(2,3-di-OMe), L-Bip(2,4-di-OMe), L-Bip(2,5-di-OMe), L-Bip(3,4- di-OMe), L-Bip(2-Et,4,5-di-OMe), L-Bip(3,4-Methylene-di-oxy), L-Bip(2-Et, 4,5-Methylene-di-oxy), L-Bip(2-CH$_2$OH, 4-OMe), L-Bip(2-Ac), L-Bip(3-NH—Ac), L-Bip(4-NH—Ac), L-Bip(2,3-di-chloro), L-Bip(2,4-di-chloro), L-Bip(2,5-di-chloro), L-Bip(3,4-di-chloro), L-Bip(4-fluoro), L-Bip(3,4-di-fluoro), L-Bip(2,5-di-fluoro), L-Bip(3-n-propyl), L-Bip(4-n-propyl), L-Bip(2-iso-propyl), L-Bip(3-iso-propyl), L-Bip(4-iso-propyl), L-Bip(4-tert-butyl), L-Bip(3-phenyl), L-Bip(2-chloro), L-Bip(3-chloro), L-Bip(2-fluoro), L-Bip(3-fluoro), L-Bip(2-CF$_3$), L-Bip(3-CF$_3$), L-Bip(4-CF$_3$), L-Bip(3-NO$_2$), L-Bip(3-OCF$_3$), L-Bip(4-OCF$_3$), L-Bip(2-OEt), L-Bip(3-OEt), L-Bip(4-OEt), L-Bip(4-SMe), L-Bip(2-OH), L-Bip(3-OH), L-Bip(4-OH), L-Bip(2-CH$_2$—COOH), L-Bip(3-CH$_2$—COOH), L-Bip(4-CH$_2$—COOH), L-Bip(2-CH$_2$—NH$_2$), L-Bip(3-CH$_2$—NH$_2$), L-Bip(4-CH$_2$—NH$_2$), L-Bip(2-CH$_2$—OH), L-Bip(3-CH$_2$—OH), L-Bip(4-CH$_2$—OH), L-Phe[4-(1-propargyl)], L-Phe[4-(1-propenyl)], L-Phe[4-n-butyl], L-Phe[4-cyclohexyl], Phe(4-phenyloxy), L-Phe(penta-fluoro), L-2-(9,10-dihydrophenan-threnyl)-Ala, 4-(2-benzo(b)furan)-Phe, 4-(4-Dibenzofuran)-Phe, 4-(4-phenoxathiin)-Phe, 4-(2-Benzo(b)thiophene)-Phe, 4-(3-thiophene)-Phe, 4-(3-Quinoline)-Phe, 4-(2-naphthyl)-Phe, 4-(1-Naphthyl)-Phe, 4-(4-(3,5-dimethylisoxazole))-Phe, 4-(2,4-dimethoxypyrimidine)-Phe, homoPhe, Tyr(Bzl), Phe(3,4-di-chloro), Phe(4-Iodo), 2-Naphthyl-Ala, L-α-Me-Bip, or D-α-Me-Bip; Z is L-Bip, D-Bip, L-Bip(2-Me), D-Bip (2-Me), L-Bip(2'-Me), L-Bip(2-Et), D-Bip(2-Et), L-Bip(3-Me), L-Bip(4-Me), L-Bip(3-OMe), L-Bip(4-OMe), L-Bip(4-Et), L-Bip(2-n-propyl,2'-Me), L-Bip(2,4-di-Me), L-Bip(2-Me, 2'-Me), L-Bip(2-Me,4-OMe), L-Bip(2-Et, 4-OMe), D-Bip(2-Et,4-OMe), L-Bip(2,6-di-Me), L-Bip(2,4,6-tri-Me), L-Bip(2,3,4,5,-tetra-Me), L-Bip(3,4-di-OMe), L-Bip(2,5-di-OMe), L-Bip(3,4-Methylene-di-oxy), L-Bip(3-NH—Ac), L-Bip(2-iso-propyl), L-Bip(4-iso-propyl), L-Bip(2-Phenyl), L-Bip(4-Phenyl), L-Bip(2-fluoro), L-Bip(4-CF$_3$), L-Bip(4-OCF$_3$), L-Bip(2-OEt), L-Bip(4-OEt), L-Bip(4-SMe), L-Bip(2-CH$_2$—COOH), D-Bip(2-CH$_2$—COOH), L-Bip(2'-CH$_2$—COOH), L-Bip(3-CH$_2$—COOH), L-Bip(4-CH$_2$—COOH), L-Bip(2-CH$_2$—NH$_2$), L-Bip(3-CH$_2$—NH$_2$), L-Bip(4-CH$_2$—NH$_2$), L-Bip(2-CH$_2$—OH), L-Bip(3-CH$_2$—OH), L-Bip(4-CH$_2$—OH), L-Phe(3-Phenyl), L-Phe[4-n-Butyl], L-Phe[4-cyclohexyl], Phe(4-Phenyloxy), L-Phe(penta-fluoro), L-2-(9,10-Dihydrophenanthrenyl)-Ala, 4-(3-Pyridyl)-Phe, 4-(2-Naphthyl)-Phe, 4-(1-naphthyl)-Phe, 2-naphthyl-Ala, 2-fluorenyl-Ala, L-α-Me-Bip, D-α-Me-Bip, L-Phe(4-NO$_2$), or L-Phe(4-Iodo); A is H, acetyl, β-Ala, Ahx, Gly, Asp, Glu, Phe, Lys, Nva, Asn, Arg, Ser, Thr, Val, Trp, Tyr, caprolactam, Bip, Ser(Bzl), 3-pyridylAla, Phe(4-Me), Phe (penta-fluoro), 4-methylbenzyl, 4-fluorobenzyl, n-propyl, n-hexyl, cyclohexylmethyl, 6-hydroxypentyl, 2-thienylmethyl, 3-thienylmethyl, penta-fluorobenzyl, 2-naphthylmethyl, 4-biphenylmethyl, 9-anthracenylmethyl, benzyl, (S)-(2-amino-3-phenyl)propyl, methyl, 2-aminoethyl, or (S)-2-aminopropyl; and B is OH, NH$_2$, Trp-NH$_2$, 2-naphthylAla-NH$_2$, Phe(penta-fluoro)-NH$_2$, Ser(Bzl)-NH$_2$, Phe(4-NO$_2$)—NH$_2$, 3-pyridylAla-NH$_2$, Nva-NH$_2$, Lys-NH$_2$, Asp-NH$_2$, Ser-NH$_2$, His-NH$_2$, Tyr-NH$_2$, Phe-NH$_2$, L-Bip-NH$_2$, D-Ser-NH$_2$, Gly-OH, beta.-Ala-OH, GABA-OH, or APA-OH.

In certain embodiments, when A is not present, and X$_1$ is an R group, an R—C(O) (amide) group, a carbamate group RO—C(O), a urea R$_4$R$_5$N—C(O), a sulfonamido R—SO$_2$, or a R$_4$R$_5$N—SO$_2$; wherein R is H, C$_{1-12}$ alkyl, C$_{3-10}$ cycloalkyl, cycloalkylalkyl, heterocyclyl, heterocycloalkyl, aryl, heteroaryl, arylalkyl, aryloxyalkyl, heteroarylalkyl, heteroary-loxyalkyl, or heteroarylalkoxyalkyl; and where R$_4$ and R$_5$ are each independently H, C$_{1-12}$ alkyl, C$_{3-10}$ cycloalkyl, cycloalkylalkyl, heterocyclyl, heterocycloalkyl, aryl, heteroaryl, arylalkyl, aryloxyalkyl, heteroarylalkyl, or heteroaryloxyalky.

In certain embodiments, when B is not present and Z is OR$_1$, NR$_1$R$_2$, or an amino-alcohol; where R$_1$ and R$_2$ are independently H, C$_{1-12}$ alkyl, C$_{3-10}$ cycloalkyl, cycloalkylalkyl, heterocycle, heterocycloalkyl, aryl, heteroaryl, arylalkyl, aryloxyalkyl, heteroarylalkyl, or heteroaryloxyalkyl. In certain embodiments, X$_1$ (where applicable), X$_2$, and X$_3$ are N—H or N-alkylated, (e.g., N-methylated) amino acid residues. The polypeptide may be a 10-mer to 15-mer and capable of binding to and activating the GLP-1 receptor.

ABBREVIATIONS

Nal=naphthylalanine
pGly=pentylglycine
t-BuG or =t-butylglycine
TPro=thioproline
HPro=homoproline
NmA=N-methylalanine
Cya=cysteic acid
Thi=β 2-Thienyl-Ala
hSer=homoserine
Aib=a-aminoisobutyric acid
Bip=biphenylalanine
Nle=norleucine
Ahx=2-aminohexanoic acid
Nva=norvaline Modified Forms of GLP-1 Analogs Any of the peptide GLP-1 analogs described herein may be modified (e.g., as described herein or as known in the art. As described in U.S. Pat. No. 6,924,264, the polypeptide can be bound to a polymer to increase its molecular weight. Exemplary polymers include polyethylene glycol polymers, polyamino acids, albumin, gelatin, succinyl-gelatin, (hydroxypropyl)-methacrylamide, fatty acids, polysaccharides, lipid amino acids, and dextran.

In one case, the polypeptide is modified by addition of albumin (e.g., human albumin), or an analog or fragment thereof, or the Fc portion of an immunoglobulin. Such an approach is described, for example, in U.S. Pat. No. 7,271,149.

In one example, the polypeptide is modified by addition of a lipophilic substituent, as described in PCT Publication WO 98/08871. The lipophilic substituent may include a partially or completely hydrogenated cyclopentanophenathrene skeleton, a straight-chain or branched alkyl group; the acyl group of a straight-chain or branched fatty acid (e.g., a group including CH$_3$(CH$_2$)$_n$CO— or HOOC(CH$_2$)$_m$CO—, where n or m is 4 to 38); an acyl group of a straight-chain or branched alkane a,ω-dicarboxylic acid; CH$_3$(CH$_2$)$_p$((CH$_2$)$_q$,COOH) CHNH—CO(CH$_2$)$_2$CO—, where p and q are integers and p+q is 8 to 33; CH$_3$(CH$_2$)$_r$CO—NHCH(COOH)(CH$_2$)$_2$CO—, where r is 10 to 24; CH$_3$(CH$_2$)$_s$CO—NHCH((CH$_2$)$_2$COOH)CO—, where s is 8 to 24; COOH(CH$_2$)$_u$CO—, where t is 8 to 24; —NHCH(COOH)(CH$_2$)$_4$NH—CO(CH$_2$)$_u$—CH$_3$, where u is 8 to 18; —NHCH(COOH)(CH$_2$)$_4$NH—COCH((CH$_2$)$_2$COOH)NH—CO(CH$_2$)$_w$CH$_3$, where w is 10 to 16; —NHCH(COOH)(CH$_2$)$_4$NH—CO(CH$_2$)$_2$CH (COOH)NH—CO(CH$_2$)$_x$CH$_3$, where x is 10 to 16; or —NHCH(COOH)(CH$_2$)$_4$NH—CO(CH$_2$)$_2$CH(COOH) NHCO(CH$_2$)$_y$CH$_3$, where y is 1 to 22.

In other embodiments, the GLP-1 peptide is modified by addition of a chemically reactive group such as a maleimide group, as described in U.S. Pat. No. 6,593,295. These groups can react with available reactive functionalities on blood components to form covalent bonds and can extending the effective therapeutic in vivo half-life of the modified insulinotropic peptides. To form covalent bonds with the functional group on a protein, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxy-sulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA).

Primary amines are the principal targets for NHS esters. Accessible α-amine groups present on the N-termini of proteins and the ε-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the invention, the functional group on the protein will be a thiol group and the chemically reactive group will be a maleimido-containing group such as gamma-maleimide-butrylamide (GMBA or MPA). Such maleimide containing groups are referred to herein as maleido groups.

The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl is formed, which cannot be cleaved under physiological conditions.

Peptide Vectors

The compounds of the invention can feature any of polypeptides described herein, for example, any of the peptides described in Table 1 (e.g., Angiopep-1 or Angiopep-2), or a fragment or analog thereof. In certain embodiments, the polypeptide may have at least 35%, 40%, 50%, 60%, 70%, 80%, 90%, 95%, 99%, or even 100% identity to a polypeptide described herein. The polypeptide may have one or more (e.g., 2, 3, 4, 5, 6, 7, 8, 9, 10, 11, 12, 13, 14, or 15) substitutions relative to one of the sequences described herein. Other modifications are described in greater detail below.

The invention also features fragments of these polypeptides (e.g., a functional fragment). In certain embodiments, the fragments are capable of efficiently being transported to or accumulating in a particular cell type (e.g., liver, eye, lung, kidney, or spleen) or are efficiently transported across the BBB. Truncations of the polypeptide may be 1, 2, 3, 4, 5, 6, 7, 8, 9, 10, 11, 12, or more amino acids from either the N-terminus of the polypeptide, the C-terminus of the polypeptide, or a combination thereof. Other fragments include sequences where internal portions of the polypeptide are deleted.

Additional polypeptides may be identified by using one of the assays or methods described herein. For example, a candidate polypeptide may be produced by conventional peptide synthesis, conjugated with paclitaxel and administered to a laboratory animal. A biologically-active polypeptide conjugate may be identified, for example, based on its ability to increase survival of an animal injected with tumor cells and treated with the conjugate as compared to a control which has not been treated with a conjugate (e.g., treated with the unconjugated agent). For example, a biologically active polypeptide may be identified based on its location in the parenchyma in an in situ cerebral perfusion assay.

Assays to determine accumulation in other tissues may be performed as well. Labelled conjugates of a polypeptide can be administered to an animal, and accumulation in different organs can be measured. For example, a polypeptide conjugated to a detectable label (e.g., a near-IR fluorescence spectroscopy label such as Cy5.5) allows live in vivo visualization. Such a polypeptide can be administered to an animal, and the presence of the polypeptide in an organ can be detected, thus allowing determination of the rate and amount of accumulation of the polypeptide in the desired organ. In other embodiments, the polypeptide can be labelled with a radioactive isotope (e.g., $^{125}$I). The polypeptide is then administered to an animal. After a period of time, the animal is sacrificed and the organs are extracted. The amount of radioisotope in each organ can then be measured using any means known in the art. By comparing the amount of a labeled candidate polypeptide in a particular organ relative to the amount of a labeled control polypeptide, the ability of the candidate polypeptide to access and accumulate in a particular tissue can be ascertained. Appropriate negative controls include any peptide or polypeptide known not to be efficiently transported into a particular cell type (e.g., a peptide related to Angiopep that does not cross the BBB, or any other peptide).

Additional sequences are described in U.S. Pat. No. 5,807,980 (e.g., SEQ ID NO:102 herein), U.S. Pat. No. 5,780,265 (e.g., SEQ ID NO:103), U.S. Pat. No. 5,118,668 (e.g., SEQ ID NO:105). An exemplary nucleotide sequence encoding an aprotinin analog atgagaccag atttctgcct cgagccgccg tacactgggc cctgcaaagc tcgtatcatc cgttacttct acaatgcaaa ggcaggcctg tgtcagacct tcgtatacgg cggctgcaga gctaagcgta acaacttcaa atccgcggaa gactgcatgc gtacttgcgg tggtgcttag; SEQ ID NO:6; Genbank accession No. X04666). Other examples of aprotinin analogs may be found by performing a protein BLAST (Genbank) using the synthetic aprotinin sequence (or portion thereof) disclosed in International Application No. PCT/CA2004/000011. Exemplary aprotinin analogs are also found under accession Nos. CAA37967 (GI:58005) and 1405218C (GI:3604747).

Modified Polypeptides

The peptide vectors and peptide GLP-1 agonists used in the invention may have a modified amino acid sequence. In certain embodiments, the modification does not destroy significantly a desired biological activity (e.g., ability to cross the BBB or GLP-1 agonist activity). The modification may reduce (e.g., by at least 5%, 10%, 20%, 25%, 35%, 50%, 60%, 70%, 75%, 80%, 90%, or 95%), may have no effect, or may increase (e.g., by at least 5%, 10%, 25%, 50%, 100%, 200%, 500%, or 1000%) the biological activity of the original polypeptide. The modified peptide may have or may optimize a characteristic of a polypeptide, such as in vivo stability, bioavailability, toxicity, immunological activity, immunological identity, and conjugation properties.

Modifications include those by natural processes, such as posttranslational processing, or by chemical modification techniques known in the art. Modifications may occur anywhere in a polypeptide including the polypeptide backbone, the amino acid side chains and the amino- or carboxy-terminus. The same type of modification may be present in the same or varying degrees at several sites in a given polypeptide, and a polypeptide may contain more than one type of modification. Polypeptides may be branched as a result of ubiquitination, and they may be cyclic, with or without branching. Cyclic, branched, and branched cyclic polypeptides may result from posttranslational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to fiavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide can also include an amino acid insertion, deletion, or substitution, either conservative or non-conservative (e.g., D-amino acids, desamino acids) in the polypeptide sequence (e.g., where such changes do not substantially alter the biological activity of the polypeptide). In particular, the addition of one or more cysteine residues to the amino or carboxy terminus of any of the polypeptides of the invention can facilitate conjugation of these polypeptides by, e.g., disulfide bonding. For example, Angiopep-1 (SEQ ID NO:67), Angiopep-2 (SEQ ID NO:97), or Angiopep-7 (SEQ ID NO:112) can be modified to include a single cysteine residue at the amino-terminus (SEQ ID NOS: 71, 113, and 115, respectively) or a single cysteine residue at the carboxy-terminus (SEQ ID NOS: 72, 114, and 116, respectively). Amino acid substitutions can be conservative (i.e., wherein a residue is replaced by another of the same general type or group) or non-conservative (i.e., wherein a residue is replaced by an amino acid of another type). In addition, a non-naturally occurring amino acid can be substituted for a naturally occurring amino acid (i.e., non-naturally occurring conservative amino acid substitution or a non-naturally occurring non-conservative amino acid substitution).

Polypeptides made synthetically can include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogs may be generated by substitutional mutagenesis and retain the biological activity of the original polypeptide. Examples of substitutions identified as "conservative substitutions" are shown in Table 2. If such substitutions result in a change not desired, then other type of substitutions, denominated "exemplary substitutions" in Table 3, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe),
(2) neutral hydrophilic: Cysteine (Cys), Serine (Ser), Threonine (Thr)
(3) acidic/negatively charged: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro);
(6) aromatic: Tryptophan (Trp), Tyrosine (Tyr), Phenylalanine (Phe), Histidine (His),
(7) polar: Ser, Thr, Asn, Gln
(8) basic positively charged: Arg, Lys, His, and;
(9) charged: Asp, Glu, Arg, Lys, His Other amino acid substitutions are listed in Table 3.

TABLE 2

Amino acid substitutions

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Polypeptide Derivatives and Peptidomimetics

In addition to polypeptides consisting of naturally occurring amino acids, peptidomimetics or polypeptide analogs are also encompassed by the present invention and can form the peptide vectors or GLP-1 agonists used in the compounds of the invention. Polypeptide analogs are commonly used in the pharmaceutical industry as non-peptide drugs with properties analogous to those of the template polypeptide. The non-peptide compounds are termed "peptide mimetics" or peptidomimetics (Fauchere et al., *Infect. Immun.* 54:283-287, 1986 and Evans et al., *J. Med. Chem.* 30:1229-1239, 1987). Peptide mimetics that are structurally related to therapeutically useful peptides or polypeptides may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —CH$_2$NH—, —CH$_2$S—, —CH$_2$—CH$_2$—, —CH=CH— (cis and trans), —CH$_2$SO—, —CH(OH)CH$_2$—, —COCH$_2$— etc., by methods well known in the art (Spatola, *Peptide Backbone Modifications, Vega Data,* 1:267, 1983; Spatola et al., *Life Sci.* 38:1243-1249, 1986; Hudson et al.,

*Int. J. Pept. Res.* 14:177-185, 1979; and Weinstein, 1983, Chemistry and Biochemistry, of Amino Acids, Peptides and Proteins, Weinstein eds, Marcel Dekker, New York). Such polypeptide mimetics may have significant advantages over naturally occurring polypeptides including more economical production, greater chemical stability, enhanced pharmacological properties (e.g., half-life, absorption, potency, efficiency), reduced antigenicity, and others.

While the peptide vectors described herein may efficiently cross the BBB or target particular cell types (e.g., those described herein), their effectiveness may be reduced by the presence of proteases. Likewise, the effectiveness of GLP-1 agonists used in the invention may be similarly reduced. Serum proteases have specific substrate requirements, including L-amino acids and peptide bonds for cleavage. Furthermore, exopeptidases, which represent the most prominent component of the protease activity in serum, usually act on the first peptide bond of the polypeptide and require a free N-terminus (Powell et al., *Pharm. Res.* 10:1268-1273, 1993). In light of this, it is often advantageous to use modified versions of polypeptides. The modified polypeptides retain the structural characteristics of the original L-amino acid polypeptides, but advantageously are not readily susceptible to cleavage by protease and/or exopeptidases.

Systematic substitution of one or more amino acids of a consensus sequence with D-amino acid of the same type (e.g., an enantiomer; D-lysine in place of L-lysine) may be used to generate more stable polypeptides. Thus, a polypeptide derivative or peptidomimetic as described herein may be all L-, all D-, or mixed D, L polypeptides. The presence of an N-terminal or C-terminal D-amino acid increases the in vivo stability of a polypeptide because peptidases cannot utilize a D-amino acid as a substrate (Powell et al., *Pharm. Res.* 10:1268-1273, 1993). Reverse-D polypeptides are polypeptides containing D-amino acids, arranged in a reverse sequence relative to a polypeptide containing L-amino acids. Thus, the C-terminal residue of an L-amino acid polypeptide becomes N-terminal for the D-amino acid polypeptide, and so forth. Reverse D-polypeptides retain the same tertiary conformation and therefore the same activity, as the L-amino acid polypeptides, but are more stable to enzymatic degradation in vitro and in vivo, and thus have greater therapeutic efficacy than the original polypeptide (Brady and Dodson, *Nature* 368:692-693, 1994 and Jameson et al., *Nature* 368:744-746, 1994). In addition to reverse-D-polypeptides, constrained polypeptides comprising a consensus sequence or a substantially identical consensus sequence variation may be generated by methods well known in the art (Rizo et al., *Ann. Rev. Biochem.* 61:387-418, 1992). For example, constrained polypeptides may be generated by adding cysteine residues capable of forming disulfide bridges and, thereby, resulting in a cyclic polypeptide. Cyclic polypeptides have no free N- or C-termini. Accordingly, they are not susceptible to proteolysis by exopeptidases, although they are, of course, susceptible to endopeptidases, which do not cleave at polypeptide termini. The amino acid sequences of the polypeptides with N-terminal or C-terminal D-amino acids and of the cyclic polypeptides are usually identical to the sequences of the polypeptides to which they correspond, except for the presence of N-terminal or C-terminal D-amino acid residue, or their circular structure, respectively.

A cyclic derivative containing an intramolecular disulfide bond may be prepared by conventional solid phase synthesis while incorporating suitable S-protected cysteine or homocysteine residues at the positions selected for cyclization such as the amino and carboxy termini (Sah et al., *J. Pharm. Pharmacol.* 48:197, 1996). Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure or (2) by removal of the polypeptide from the support along with complete side chain de-protection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S-alkyl bonds can be prepared by conventional solid phase chemistry while incorporating an amino acid residue with a suitable amino-protected side chain, and a suitable S-protected cysteine or homocysteine residue at the position selected for cyclization.

Another effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al., *Pharm. Res.* 10:1268-1273, 1993). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified polypeptides consisting of polypeptides bearing an N-terminal acetyl group and/or a C-terminal amide group.

Also included by the present invention are other types of polypeptide derivatives containing additional chemical moieties not normally part of the polypeptide, provided that the derivative retains the desired functional activity of the polypeptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives.

Longer polypeptide sequences which result from the addition of additional amino acid residues to the polypeptides described herein are also encompassed in the present invention. Such longer polypeptide sequences can be expected to have the same biological activity and specificity (e.g., cell tropism) as the polypeptides described above. While polypeptides having a substantial number of additional amino acids are not excluded, it is recognized that some large polypeptides may assume a configuration that masks the effective sequence, thereby preventing binding to a target (e.g., a member of the LRP receptor family such as LRP or LRP2). These derivatives could act as competitive antagonists. Thus, while the present invention encompasses polypeptides or derivatives of the polypeptides described herein having an extension, desirably the extension does not destroy the cell targeting activity of the polypeptides or its derivatives.

Other derivatives included in the present invention are dual polypeptides consisting of two of the same, or two different polypeptides, as described herein, covalently linked to one another either directly or through a spacer, such as by a short stretch of alanine residues or by a putative site for proteolysis (e.g., by cathepsin, see e.g., U.S. Pat. No. 5,126,249 and European Patent No. 495 049). Multimers of the polypeptides described herein consist of a polymer of molecules formed from the same or different polypeptides or derivatives thereof.

The present invention also encompasses polypeptide derivatives that are chimeric or fusion proteins containing a polypeptide described herein, or fragment thereof, linked at its amino- or carboxy-terminal end, or both, to an amino acid sequence of a different protein. Such a chimeric or fusion protein may be produced by recombinant expression of a nucleic acid encoding the protein. For example, a chimeric or fusion protein may contain at least 6 amino acids shared with one of the described polypeptides which desirably results in a chimeric or fusion protein that has an equivalent or greater functional activity.

Assays to Identify Peptidomimetics

As described above, non-peptidyl compounds generated to replicate the backbone geometry and pharmacophore display (peptidomimetics) of the polypeptides described herein often possess attributes of greater metabolic stability, higher potency, longer duration of action, and better bioavailability.

Peptidomimetics compounds can be obtained using any of the numerous approaches in combinatorial library methods known in the art, including biological libraries, spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer, or small molecule libraries of compounds (Lam, *Anticancer Drug Des.* 12:145, 1997). Examples of methods for the synthesis of molecular libraries can be found in the art, for example, in: DeWitt et al. (*Proc. Natl. Acad. Sci. USA* 90:6909, 1993); Erb et al. (*Proc. Natl. Acad. Sci. USA* 91:11422, 1994); Zuckermann et al. (*J. Med. Chem.* 37:2678, 1994); Cho et al. (*Science* 261:1303, 1993); Carell et al. (*Angew. Chem., Int. Ed. Engl.* 33:2059, 1994 and ibid 2061); and in Gallop et al. (*Med. Chem.* 37:1233, 1994). Libraries of compounds may be presented in solution (e.g., Houghten, *Biotechniques* 13:412-421, 1992) or on beads (Lam, *Nature* 354:82-84, 1991), chips (Fodor, *Nature* 364:555-556, 1993), bacteria or spores (U.S. Pat. No. 5,223,409), plasmids (Cull et al., *Proc. Natl. Acad. Sci. USA* 89:1865-1869, 1992) or on phage (Scott and Smith, *Science* 249:386-390, 1990), or luciferase, and the enzymatic label detected by determination of conversion of an appropriate substrate to product.

Once a polypeptide as described herein is identified, it can be isolated and purified by any number of standard methods including, but not limited to, differential solubility (e.g., precipitation), centrifugation, chromatography (e.g., affinity, ion exchange, and size exclusion), or by any other standard techniques used for the purification of peptides, peptidomimetics, or proteins. The functional properties of an identified polypeptide of interest may be evaluated using any functional assay known in the art. Desirably, assays for evaluating downstream receptor function in intracellular signaling are used (e.g., cell proliferation).

For example, the peptidomimetics compounds of the present invention may be obtained using the following three-phase process: (1) scanning the polypeptides described herein to identify regions of secondary structure necessary for targeting the particular cell types described herein; (2) using conformationally constrained dipeptide surrogates to refine the backbone geometry and provide organic platforms corresponding to these surrogates; and (3) using the best organic platforms to display organic pharmocophores in libraries of candidates designed to mimic the desired activity of the native polypeptide. In more detail the three phases are as follows. In phase 1, the lead candidate polypeptides are scanned and their structure abridged to identify the requirements for their activity. A series of polypeptide analogs of the original are synthesized. In phase 2, the best polypeptide analogs are investigated using the conformationally constrained dipeptide surrogates. Indolizidin-2-one, indolizidin-9-one and quinolizidinone amino acids ($I^2aa$, $I^9aa$ and Qaa respectively) are used as platforms for studying backbone geometry of the best peptide candidates. These and related platforms (reviewed in Halab et al., *Biopolymers* 55:101-122, 2000 and Hanessian et al., *Tetrahedron* 53:12789-12854, 1997) may be introduced at specific regions of the polypeptide to orient the pharmacophores in different directions. Biological evaluation of these analogs identifies improved lead polypeptides that mimic the geometric requirements for activity. In phase 3, the platforms from the most active lead polypeptides are used to display organic surrogates of the pharmacophores responsible for activity of the native peptide. The pharmacophores and scaffolds are combined in a parallel synthesis format. Derivation of polypeptides and the above phases can be accomplished by other means using methods known in the art.

Structure function relationships determined from the polypeptides, polypeptide derivatives, peptidomimetics or other small molecules described herein may be used to refine and prepare analogous molecular structures having similar or better properties. Accordingly, the compounds of the present invention also include molecules that share the structure, polarity, charge characteristics and side chain properties of the polypeptides described herein.

In summary, based on the disclosure herein, those skilled in the art can develop peptides and peptidomimetics screening assays which are useful for identifying compounds for targeting an agent to particular cell types (e.g., those described herein). The assays of this invention may be developed for low-throughput, high-throughput, or ultra-high throughput screening formats. Assays of the present invention include assays amenable to automation.

Linkers

The GLP-1 agonist may be bound to the vector peptide either directly (e.g., through a covalent bond such as a peptide bond) or may be bound through a linker. Linkers include chemical linking agents (e.g., cleavable linkers) and peptides.

In some embodiments, the linker is a chemical linking agent. The GLP-1 agonist and vector peptide may be conjugated through sulfhydryl groups, amino groups (amines), and/or carbohydrates or any appropriate reactive group. Homobifunctional and heterobifunctional cross-linkers (conjugation agents) are available from many commercial sources. Regions available for cross-linking may be found on the polypeptides of the present invention. The cross-linker may comprise a flexible arm, e.g., 2, 3, 4, 5, 6, 7, 8, 9, 10, 11, 12, 13, 14, or 15 carbon atoms. Exemplary cross-linkers include BS3 ([Bis(sulfosuccinimidyl)suberate]; BS3 is a homobifunctional N-hydroxysuccinimide ester that targets accessible primary amines), NHS/EDC (N-hydroxysuccinimide and N-ethyl-'(dimethylaminopropyl)carbodimide;

NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups).

To form covalent bonds, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA).

Primary amines are the principal targets for NHS esters. Accessible α-amine groups present on the N-termini of proteins and the ε-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the invention, the functional group on the protein will be a thiol group and the chemically reactive group will be a maleimido-containing group such as gamma-maleimidebutrylamide (GMBA or MPA). Such maleimide containing groups are referred to herein as maleido groups.

The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed.

In other embodiments, the linker includes at least one amino acid (e.g., a peptide of at least 2, 3, 4, 5, 6, 7, 10, 15, 20, 25, 40, or 50 amino acids). In certain embodiments, the linker is a single amino acid (e.g., any naturally occurring amino acid such as Cys). In other embodiments, a glycine-rich peptide such as a peptide having the sequence [Gly-Gly-Gly-Gly-Ser]$_n$ (SEQ ID NO:138) where n is 1, 2, 3, 4, 5 or 6 is used, as described in U.S. Pat. No. 7,271,149. In other embodiments, a serine-rich peptide linker is used, as described in U.S. Pat. No. 5,525,491. Serine rich peptide linkers include those of the formula [X-X-X-X-Gly]$_y$ (SEQ ID NO:139), where up to two of the X are Thr, and the remaining X are Ser, and y is 1 to 5 (e.g., Ser-Ser-Ser-Ser-Gly (SEQ ID NO:140), where y is greater than 1). In some cases, the linker is a single amino acid (e.g., any amino acid, such as Gly or Cys).

Examples of suitable linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. In one particular embodiment, the further linker is succinic acid which, e.g., forms an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a N$^ε$-acylated lysine residue.

GLP-1 Agonist Activity Assay

Determination of whether a compound has GLP-1 agonist activity can be performed using any method known in the art. Cyclic AMP (cAMP) production from cells expressing a GLP-1 receptor (e.g., a human receptor) can be measured in the presence and in the absence of a compound, where an increase in cAMP production indicates the compound to be a GLP-1 agonist.

In one example described in U.S. patent application Publication No. 2008/0207507, baby hamster kidney (BHK) cells expressing the cloned human GLP-1 receptor (BHK-467-12A) were grown in DMEM media with the addition of 100 IU/ml penicillin, 100 µg/ml streptomycin, 5% fetal calf serum, and 0.5 mg/mL Geneticin G-418 (Life Technologies). The cells were washed twice in phosphate buffered saline and harvested with Versene. Plasma membranes were prepared from the cells by homogenisation with an Ultraturrax in buffer 1 (20 mM HEPES-Na, 10 mM EDTA, pH 7.4). The homogenate was centrifuged at 48,000×g for 15 min at 4° C. The pellet was suspended by homogenization in buffer 2 (20 mM HEPES-Na, 0.1 mM EDTA, pH 7.4), then centrifuged at 48,000×g for 15 min at 4° C. The washing procedure was repeated one more time. The final pellet was suspended in buffer 2 and used immediately for assays or stored at −80° C.

The functional receptor assay was carried out by measuring cAMP as a response to stimulation by the insulinotropic agent. cAMP formed was quantified by the AlphaScreen™ cAMP Kit (Perkin Elmer Life Sciences). Incubations were carried out in half-area 96-well microtiter plates in a total volume of 50 µL buffer 3 (50 mM Tris-HCl, 5 mM HEPES, 10 mM MgCl$_2$, pH 7.4) and with the following additions: 1 mM ATP, 1 µM GTP, 0.5 mM 3-isobutyl-1-methylxanthine (IBMX), 0.01% Tween-20, 0.1% BSA, 6 µg membrane preparation, 15 µg/ml acceptor beads, 20 µg/ml donor beads preincubated with 6 nM biotinyl-cAMP. Compounds to be tested for agonist activity were dissolved and diluted in buffer 3. GTP was freshly prepared for each experiment. The plate was incubated in the dark with slow agitation for three hours at room temperature followed by counting in the Fusion™ instrument (Perkin Elmer Life Sciences). Concentration-response curves were plotted for the individual compounds and EC$_{50}$ values estimated using a four-parameter logistic model with Prism v. 4.0 (GraphPad, Carlsbad, Calif.).

Therapeutic Applications

The compounds of the invention can be used in any therapeutic application where a GLP-1 agonist activity in the brain, or in particular tissues, is desired. GLP-1 agonist activity is associated with stimulation of insulin secretion (i.e., to act as an incretin hormone) and inhibition glucagon secretion, thereby contributing to limit postprandial glucose excursions. GLP-1 agonists can also inhibit gastrointestinal motility and secretion, thus acting as an enterogastrone and part of the "ileal brake" mechanism. GLP-1 also appears to be a physiological regulator of appetite and food intake. Because of these actions, GLP-1 and GLP-1 receptor agonists can be used for therapy of metabolic disorders, as reviewed in, e.g., Kinzig et al., J Neurosci 23:6163-6170, 2003. Such disorders include obesity, hyperglycemia, dyslipidemia, hypertriglyceridemia, syndrome X, insulin resistance, IGT, diabetic dyslipidemia, hyperlipidemia, a cardiovascular disease, and hypertension.

GLP-1 is also has neurological effects including sedative or anti-anxiolytic effects, as described in U.S. Pat. No. 5,846, 937. Thus, GLP-1 agonists can be used in the treatment of anxiety, aggression, psychosis, seizures, panic attacks, hysteria, or sleep disorders. GLP-1 agonists can also be used to treat Alzheimer's disease, as GLP-1 agonists have been shown to protect neurons against amyloid-β peptide and glutamate-induced apoptosis (Perry et al., Curr Alzheimer Res 2:377-85, 2005).

Other therapeutic uses for GLP-1 agonists include improving learning, enhancing neuroprotection, and alleviating a symptom of a disease or disorder of the central nervous system, e.g., through modulation of neurogenesis, and e.g., Parkinson's Disease, Alzheimer's Disease, Huntington's Disease, ALS, stroke, ADD, and neuropsychiatric syndromes (U.S. Pat. No. 6,969,702 and U.S. patent application No. 2002/0115605). Stimulation of neurogenesis using GLP-1 agonists has been described, for example, in Bertilsson et al., J Neurosci Res 86:326-338, 2008.

Still other therapeutic uses include converting liver stem/progenitor cells into functional pancreatic cells (U.S. patent application Publication No. 2005/0053588); preventing beta-cell deterioration (U.S. Pat. Nos. 7,259,233 and 6,569,832) and stimulation of beta-cell proliferation (U.S. patent application Publication No. 2003/0224983); treating obesity (U.S. Pat. No. 7,211,557); suppressing appetite and inducing satiety (U.S. patent application Publication No. 2003/0232754); treating irritable bowel syndrome (U.S. Pat. No. 6,348,447); reducing the morbidity and/or mortality associated with myocardial infarction (U.S. Pat. No. 6,747,006) and stroke (PCT Publication No. WO 00/16797); treating acute coronary syndrome characterized by an absence of Q-wave myocardial infarction (U.S. Pat. No. 7,056,887); attenuating post-surgical catabolic changes (U.S. Pat. No. 6,006,753); treating hibernating myocardium or diabetic cardiomyopathy (U.S. Pat. No. 6,894,024); suppressing plasma blood levels of norepinepherine (U.S. Pat. No. 6,894,024); increasing urinary sodium excretion, decreasing urinary potassium concentration (U.S. Pat. No. 6,703,359); treating conditions or disorders associated with toxic hypervolemia, e.g., renal failure, congestive heart failure, nephrotic syndrome, cirrhosis, pulmonary edema, and hypertension (U.S. Pat. No. 6,703,359); inducing an inotropic response and increasing cardiac contractility (U.S. Pat. No. 6,703,359); treating polycystic ovary syndrome (U.S. Pat. No. 7,105,489); treating respiratory distress (U.S. patent application Publication No. 2004/0235726); improving nutrition via a non-alimentary route, i.e., via intravenous, subcutaneous, intramuscular, peritoneal, or other injection or infusion (U.S. Pat. No. 6,852,690); treating nephropathy (U.S. patent application Publication No. 2004/0209803); treating left ventricular systolic dysfunction, e.g., with abnormal left ventricular ejection fraction (U.S. Pat. No. 7,192,922); inhibiting antro-duodenal motility, e.g., for the treatment or prevention of gastrointestinal disorders such as diarrhea, postoperative dumping syndrome and irritable bowel syndrome, and as premedication in endoscopic procedures (U.S. Pat. No. 6,579,851); treating critical illness polyneuropathy (CIPN) and systemic inflammatory response syndrome (SIRS) (U.S. patent application Publication No. 2003/0199445); modulating triglyceride levels and treating dyslipidemia (U.S. patent application Publication Nos. 2003/0036504 and 2003/0143183); treating organ tissue injury caused by reperfusion of blood flow following ischemia (U.S. Pat. No. 6,284,725); treating coronary heart disease risk factor (CHDRF) syndrome (U.S. Pat. No. 6,528,520); and others.

Administration and Dosage

The present invention also features pharmaceutical compositions that contain a therapeutically effective amount of a compound of the invention. The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer (*Science* 249:1527-1533, 1990).

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a subject with a clinically determined predisposition or increased susceptibility to a metabolic disorder or neurological disease. Compositions of the invention can be administered to the patient (e.g., a human) in an amount sufficient to delay, reduce, or preferably prevent the onset of clinical disease. In therapeutic applications, compositions are administered to a subject (e.g., a human) already suffering from disease (e.g., a metabolic disorder such as those described herein, or a neurological disease) in an amount sufficient to cure or at least partially arrest the symptoms of the condition and its complications. An amount adequate to accomplish this purpose is defined as a "therapeutically effective amount," an amount of a compound sufficient to substantially improve some symptom associated with a disease or a medical condition. For example, in the treatment of a metabolic disorder (e.g., those described herein), an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Exendin-4 is typically taken twice daily at either 5 µg or 10 µg per dose for treatment of diabetes. The compounds of the invention may be administered in equivalent doses of as specified for exendin-4, may be administered in higher equivalent doses (e.g., 10%, 25%, 50%, 100%, 200%, 500%, 1000% greater doses), or can be administered in lower equivalent doses (e.g., 90%, 75%, 50%, 40%, 30%, 20%, 15%, 12%, 10%, 8%, 7%, 6%, 5%, 4%, 3%, 2%, 1%, 0.5%, or 0.1% of the equivalent dose). Amounts effective for this use may depend on the severity of the disease or condition and the weight and general state of the patient, but generally range from about 0.05 µg to about 1000 µg (e.g., 0.5-100 µg) of an equivalent amount of exendin-4 the agent or agents per dose per patient. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. Because certain compounds of the invention exhibit an enhanced ability to cross the BBB, the dosage of the compounds of the invention can be lower than (e.g., less than or equal to about 90%, 75%, 50%, 40%, 30%, 20%, 15%, 12%, 10%, 8%, 7%, 6%, 5%, 4%, 3%, 2%, 1%, 0.5%, or 0.1% of) the equivalent dose of required for a therapeutic effect of the unconjugated GLP-1 agonist. The agents of the invention are administered to a subject (e.g. a mammal, such as a human) in an effective amount, which is an amount that produces a desirable result in a treated subject (e.g. reduction in glycemia, reduced weight gain, increased weight loss, and reduced food intake). Therapeutically effective amounts can also be determined empirically by those of skill in the art.

The patient may also receive an agent in the range of about 0.05 to 1,000 µg equivalent dose as compared to exendin-4 per dose one or more times per week (e.g., 2, 3, 4, 5, 6, or 7 or more times per week), 0.1 to 2,500 (e.g., 2,000, 1,500, 1,000, 500, 100, 10, 1, 0.5, or 0.1) µg dose per week. A patient may also receive an agent of the composition in the range of 0.1 to 3,000 µg per dose once every two or three weeks.

Single or multiple administrations of the compositions of the invention comprising an effective amount can be carried out with dose levels and pattern being selected by the treating physician. The dose and administration schedule can be determined and adjusted based on the severity of the disease or condition in the patient, which may be monitored throughout the course of treatment according to the methods commonly practiced by clinicians or those described herein.

The compounds of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

EXAMPLE 1

Synthesizing GLP-1 Agonist-Angiopep Conjugates

Figure 2:
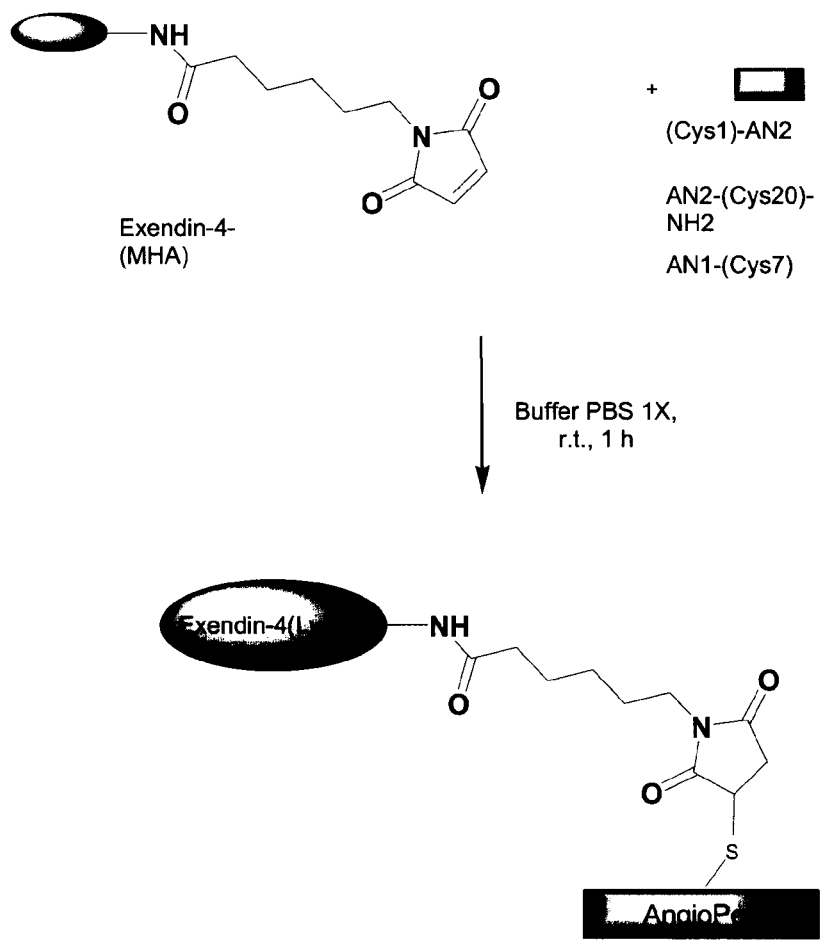
FIG. 2 is a schematic diagram of the synthetic scheme used to conjugate Cys-AngioPep2, Angiopep-2-Cys-NH$_2$, and Angiopep-1 to [Lys$^{39}$-MHA]exendin-4.

The exemplary GLP-1 conjugates, exendin-4-cysAn2 N-terminal, and Exendin-4-cysAn2 C-terminal, and Angiopep-1/Exendin 4 conjugates were made by conjugating [Lys (maleimido hexanoic acid)$^{39}$]exendin-4 to the sulfide in cys-An2 (SEQ ID NO:113), in An2-cys (SEQ ID NO:114), or in Angiopep-1 (SEQ ID NO:67) in 1×PBS buffer for 1 hour. This resulted in production of exendin-4/Angiopep conjugates, as shown in FIG. 2.

Figure 3:
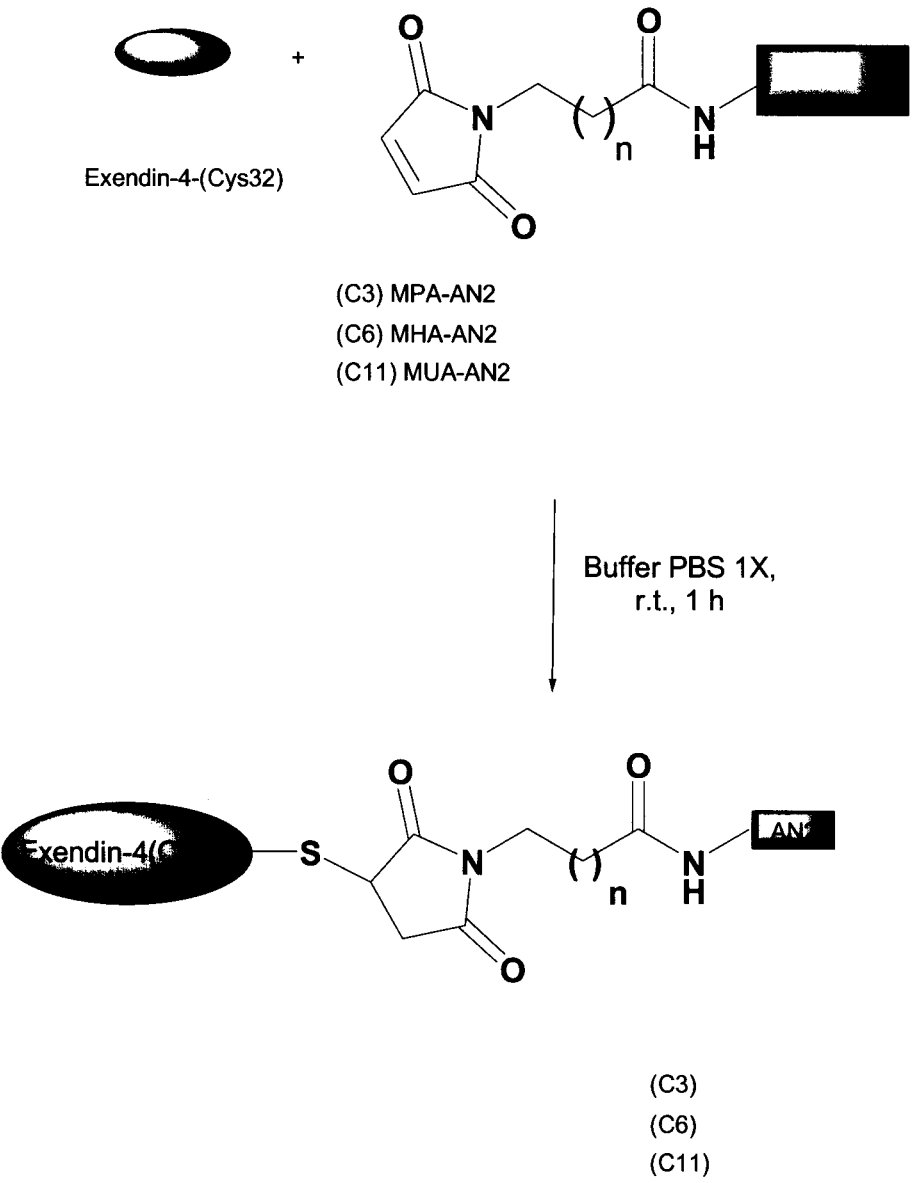
FIG. 3 is a schematic diagram of the synthetic scheme used to conjugate [Cys$^{32}$]exendin-4 to (maleimido propionic acid (MPA))-Angiopep-2, (maleimido hexamoic acid (MHA))-Angiopep-2, and (maleimido undecanoic acid (MUA))-Angiopep-2.

A second set of exendin-4/Angiopep conjugates was made by reacting Angiopep-2 having maleimido propionic acid (MPA), maleimido hexanoic acid (MHA), or maleimido undecanoic acid (MUA) bound to its N-terminus with [Cys$^{32}$] Exendin-4 to form a conjugate, as shown in FIG. 3.

EXAMPLE 2

Brain Uptake of Exendin-4/Angiopep-2 Conjugates In Situ

To measure brain uptake of the exendin-4/Angiopep-2 conjugates, we used an in situ perfusion assay. The assay, which is described in U.S. patent application Publication No. 2006/0189515, is performed as follows. The uptake of labeled exendin-4 and the exendin-4/Angiopep-2 conjugates was measured using the in situ brain perfusion method adapted in our laboratory for the study of drug uptake in the mouse brain (Dagenais et al., J Cereb Blood Flow Metab. 20:381-6, 2000; Cisternino et al., Pharm Res 18, 183-190, 2001). Briefly, the right common carotid artery of mice anesthetized with ketamine/xylazine (140/8 mg/kg i.p.) was exposed and ligated at the level of the bifurcation of the common carotid, rostral to the occipital artery. The common carotid was then catheterized rostrally with polyethylene tubing filled with heparin (25 U/ml) and mounted on a 26-gauge needle. The syringe containing the perfusion fluid ([$^{125}$I]-proteins or [$^{125}$I]-peptides in Krebs/bicarbonate buffer at pH 7.4, gassed with 95% $O_2$ and 5% $CO_2$) was placed in an infusion pump (Harvard pump PHD 2000; Harvard Apparatus) and connected to the catheter. Prior to the perfusion, the contralateral blood flow contribution was eliminated by severing the heart ventricles. The brain was perfused for 5 min at a flow rate of 1.15 ml/min. After perfusion of radiolabeled molecules, the brain was further perfused for 60 s with Krebs buffer, to wash away excess [$^{125}$I]-proteins. Mice were then decapitated to terminate perfusion and the right hemisphere was isolated on ice before being subjected to capillary depletion. Aliquots of homogenates, supernatants, pellets, and perfusates were taken to measure their contents and to evaluate the apparent volume of distribution.

Figure 4:
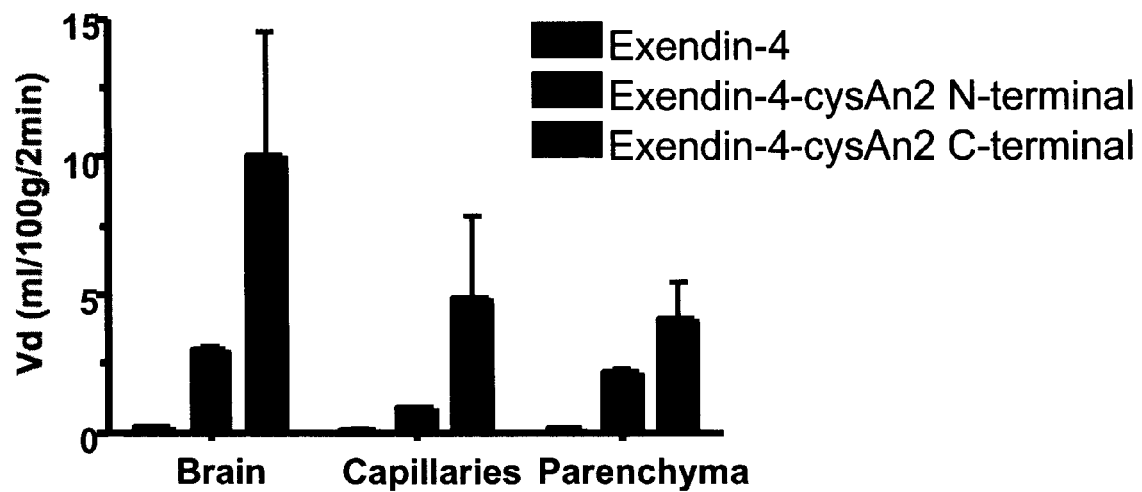
FIG. 4 is a graph showing transport of exendin-4 (left) and exendin-4/Angiopep-2 (N-terminal, center; c-terminal, right) across the BBB. The total amount in the brain, along with the amounts in the capillaries and the parenchyma are shown.

From these experiments, brain distribution of both exendin-4/Angiopep-2 conjugates was increased 15-50 fold over that of unconjugated exendin-4. The brain distribution of exendin-4 was observed at 0.2 ml/100 g/2 min, whereas the conjugate modified at its N-terminal was observed at 3 ml/100 g/2 min, and the conjugate modified at its C-terminal was observed at 10 ml/100 g/2 min. Results are shown in FIG. 4.

EXAMPLE 3

Treatment of Obese Mice with Exendin-4/Angiopep-2 Conjugates

Obese mice (ob/ob mice) were administered the [$Lys^{39}$-MHA]exendin-4/Angiopep-2-Cys-$NH_2$ conjugate (Exen-An2).
In Vivo Study to Determine the Efficacy of Exendin-4-Angiopep-2 Conjugate

| Groups | Dose (µg/kg) | Dose (nmol/kg) | Dose (µg/mouse) | mice/group | Q1D × 28 days (Total amount µg) |
|---|---|---|---|---|---|
| Control | 0 | 0 | 0 | 5 | 0 |
| Exendin-4 | 3 | 0.72 | 0.18 | 5 | 20.16 |
|  | 30 | 7.2 | 1.8 | 5 | 201.6 |
| Exen-An2 | 4.8 | 0.72 | 0.288 | 5 | 32.256 |
|  | 48 | 7.2 | 2.88 | 5 | 322.56 |

Figure 5:
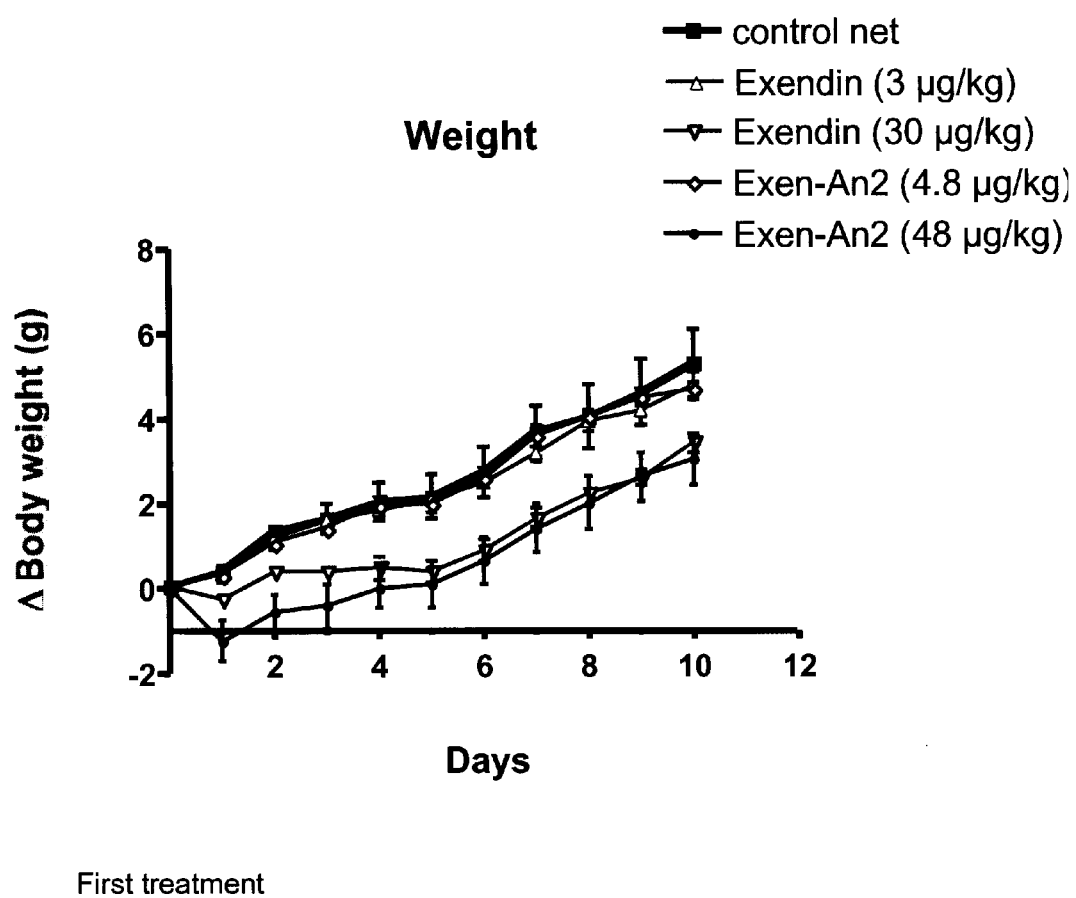
FIG. 5 is a graph showing increase in weight of (ob/ob) mice following administration of a control, exendin-4, or the [Lys$^{39}$-MHA]exendin-4/Angiopep-2-Cys-NH$_2$ conjugate (Exen-An2). Both exendin-4 and Ex-An2 were observed to reduce weight gain as compared to the animals receiving the control.
Figure 6:
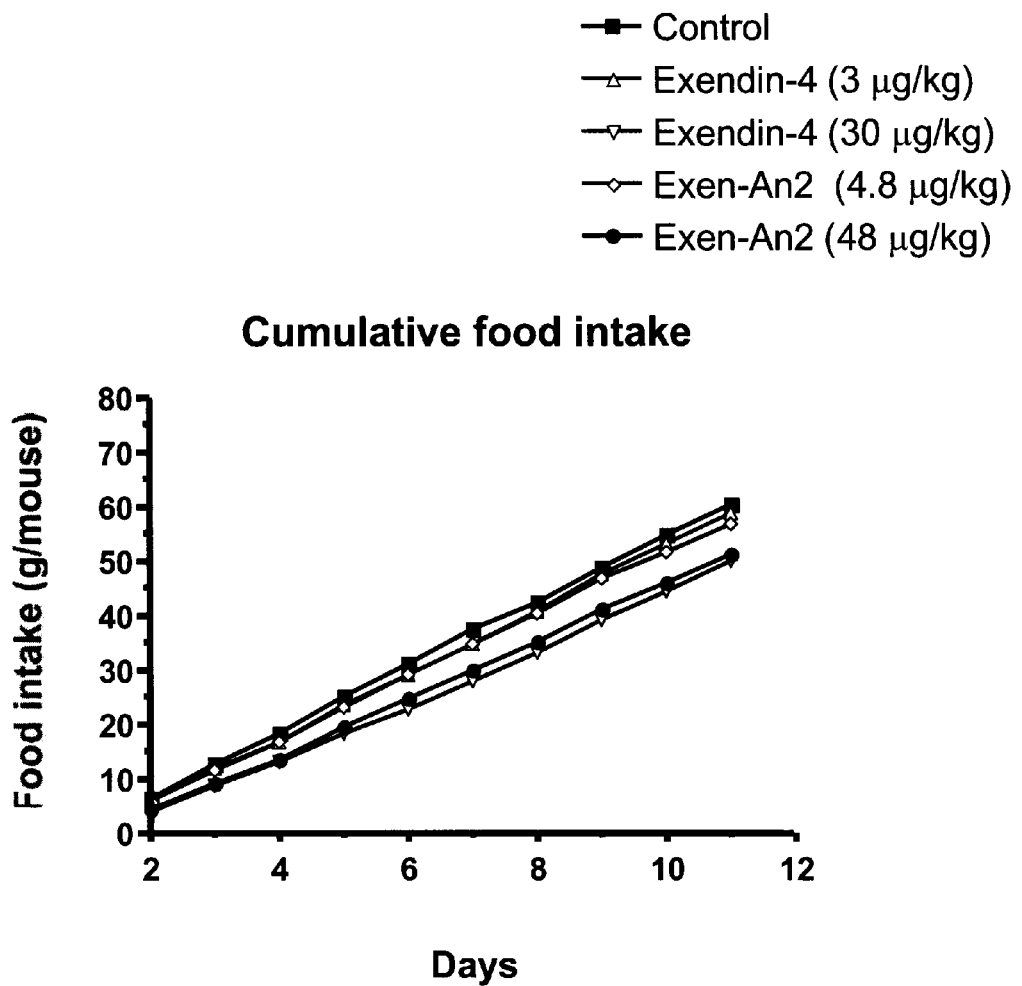
FIG. 6 is a graph showing total food consumption by (ob/ob) mice, where the mice were administered a control, exendin-4, or the Exen-An2. Both exendin-4 and Exen-An2 were observed to reduce food intake as compared to the animals receiving the control.

A 1.6 µg/kg dose of Exen-An2 is equivalent to a 1 µg/kg dose of exendin-4. The body weight of each mouse was measured daily. Food intake was estimated based on the mean values for each group, and glycemia was measured one hour following treatment. After 10 days of treatment, body weight gain and food intake of mice treated at the higher doses of either exendin-4 or the conjugate are lower than the control (FIG. 5). Food intake was also reduced in the mice receiving the higher doses of either exendin-4 or the conjugate (FIG. 6) as compared to the control.

Figure 7:
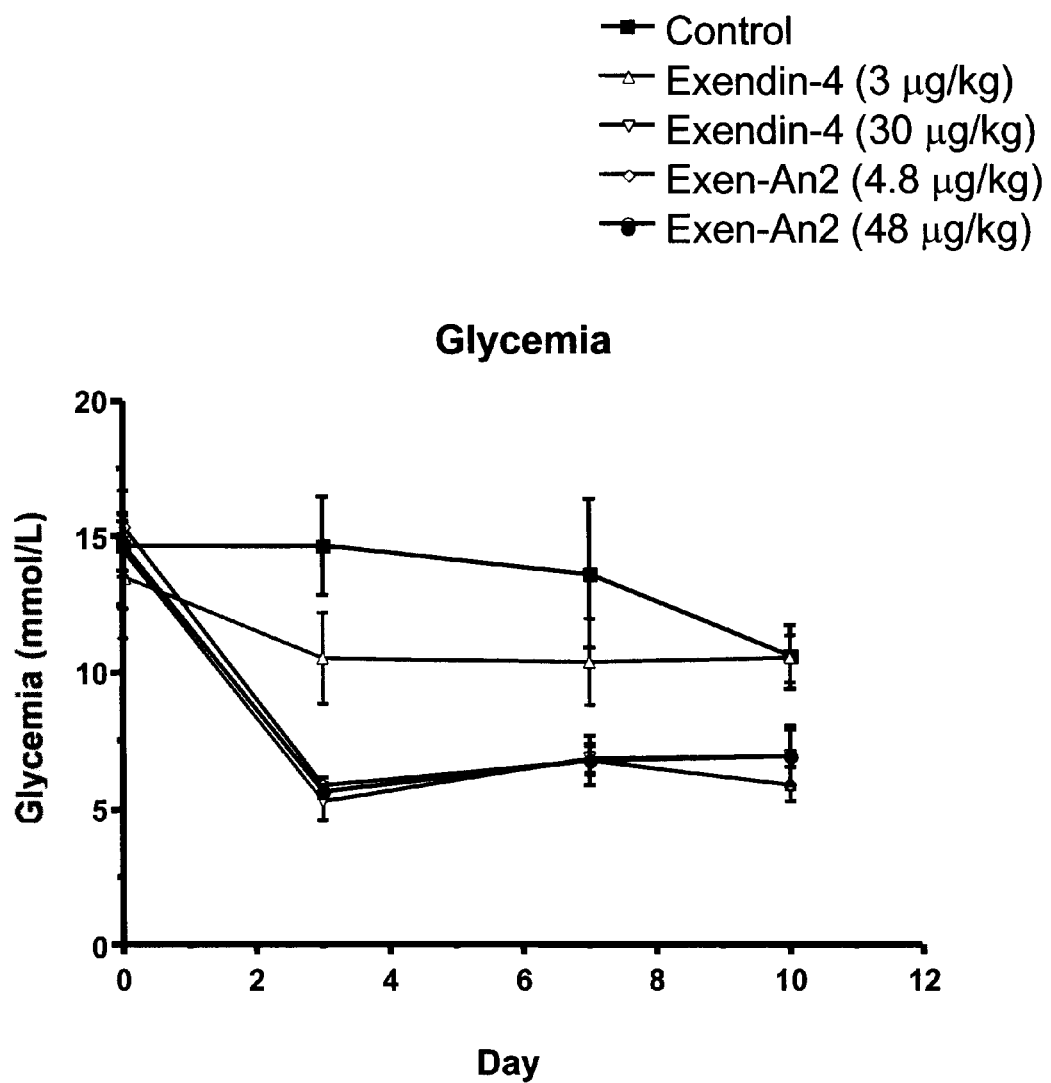
FIG. 7 is a graph showing reduction in glycemia following administration of two doses of exendin-4 (3 µg/kg and 30 µg/kg) and equivalent doses of Exen-An2 (4.8 µg/kg and 48 µg/kg). A similar reduction in glycemia at the lower dose of Exen-An2, as compared to the higher dose of exendin-4, was observed. During this experiment, one mouse in the control group died at day 12.

Glycemia measurements showed that the lower dose of the conjugate had the same effect as the higher doses of either exendin-4 or Exen-An2 (FIG. 7). Thus, a similar effect of 1/10 the dosage on glycemia is observed using the conjugate, as compared to exendin-4.

EXAMPLE 4

Generation of an Exendin-4-Angioep-2 Dimer Conjugate

Figure 8A:
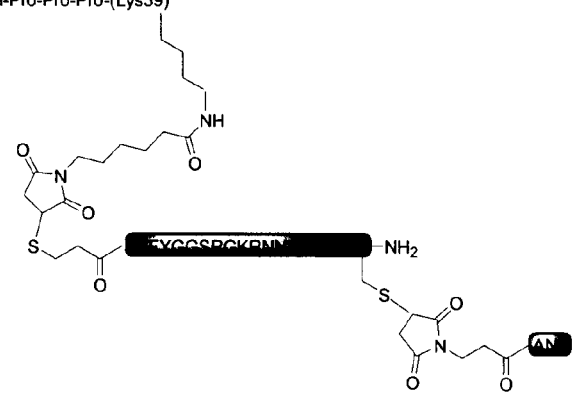
FIG. 8A is a schematic diagram showing the structure of an Exendin-4-Angiopep-2 dimer conjugate (Ex4(Lys39 (MHA))-AN2-AN2). The compound has the structure HGEGTFTSDLSKQMEEEAVR-LFIEWLKNGGPSSGAPPPK(MHA)-TFFYGGSRGKRN-NFKTEEYC-(MPA)-TFFYGGSRGKRNNFKTEEY-OH (SEQ ID NOS:117, 74, and 97, respectively), where MHA is maleimido hexanoic acid and MPA is maleimido propionic acid.
Figure 8B:
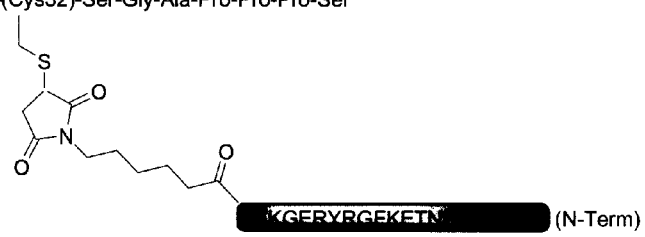
FIG. 8B is a schematic structure of an Exendin-4-scramble-Angiopep-2 (Ex4(Cys32)-ANS4 (N-Term) or Exen-S4) that was used a control. This compound has the structure HGEGTFTSDLSKQMEEEAVR-LFIEWLKNGGPCSGAPPPS-(MHA)-GYKGERYRG-FKETNFNTFS-OH (SEQ ID NOS:118 and 119, respectively), where MHA is maleimido hexanoic acid.

Using the conjugation chemistry described herein or similar chemistry, an Exendin-4-Angiopep-2 dimer was generated having the structure shown in FIG. 8A. Briefly, the amine group in the C-terminal lysine of [$Lys^{39}$]Exendin-4 was conjugated to an Angiopep-2 dimer through an MHA linker at the N-terminal threonine of the first Angiopep-2 peptide. A N-Succinimidyl-5-acetylthiopropionate (SATP) linker was attached to an Angiopep-2-Cys peptide at its N-terminus. Through this cysteine, the Angiopep-2-Cys peptide was conjugated to a second Angiopep-2 peptide, which had been modified to contain an MPA linker. The dimer was the linked to the [$Lys^{39}$]Exendin-4 through an MHA linker A control molecule (Exen-S4) was also generated using a scrambed form of Angiopep-2 conjugated at its N-terminal to the cysteine of [$Cys^{32}$]Exendin-4 through an MHA linker (FIG. 8B). These conjugates were prepared as trifluoroacetate (TFA) salts.

EXAMPLE 5

Characterization of an Exendin-4-Angiopep-2 Dimer Conjugate

Brain uptake of the exemplary GLP-1 agonist, exendin-4, was measured in situ when unconjugated, conjugated to a single Angiopep-2, conjugated to a scrambled Angiopep-2 (S4), or conjugated to a dimeric form of Angiopep-2. The experiments were performed as described in Example 2 above.

Figure 9:
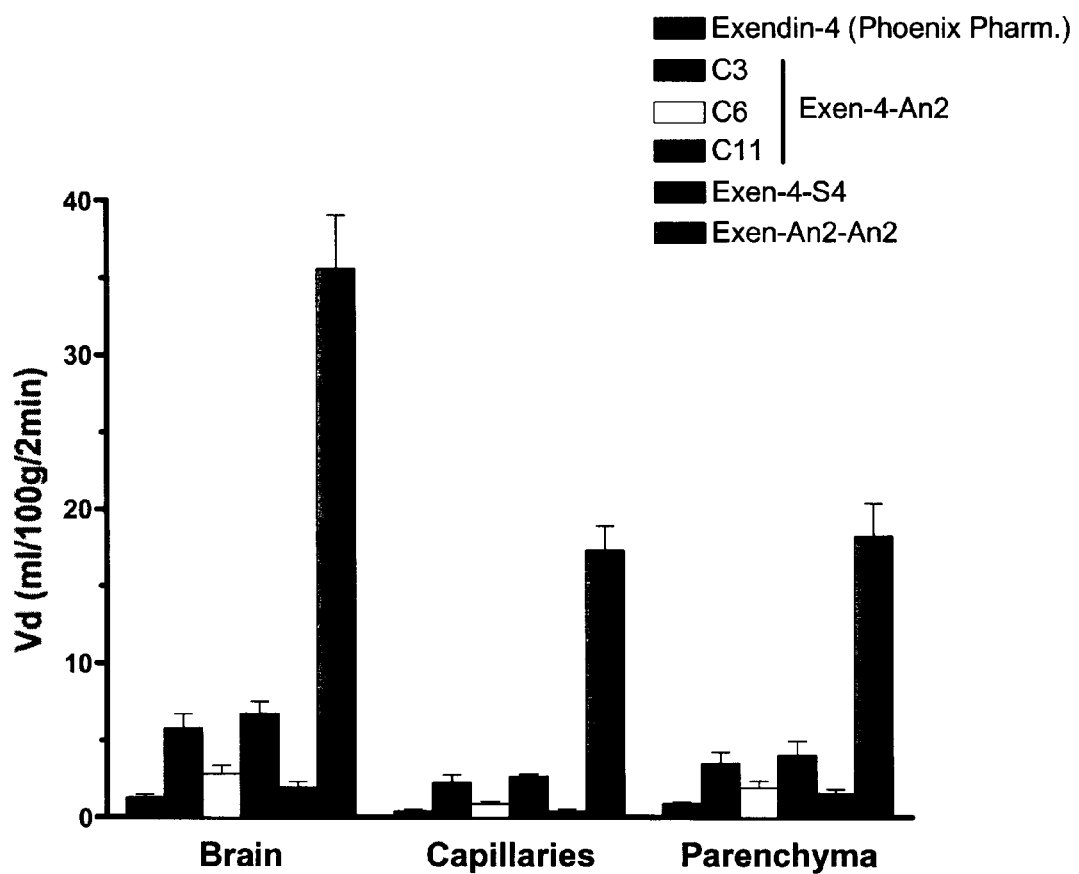
FIG. 9 is a graph showing the ability of, from left to right, Exendin-4; Exendin-4-Angiopep-2 conjugates C3, C6, and C11; Exen-S4; and Exendin-4 when conjugated to a dimeric form of Angiopep-2, to cross the BBB.

From these results, we observed that conjugation of the exendin-4 analog to the dimeric form of Angiopep-2 results in a conjugate with a surprisingly greater ability to cross the BBB as compared to either the unconjugated exendin-4 or to the exendin-4 conjugated to a single Angiopep-2 (FIG. 9).

Figure 10:
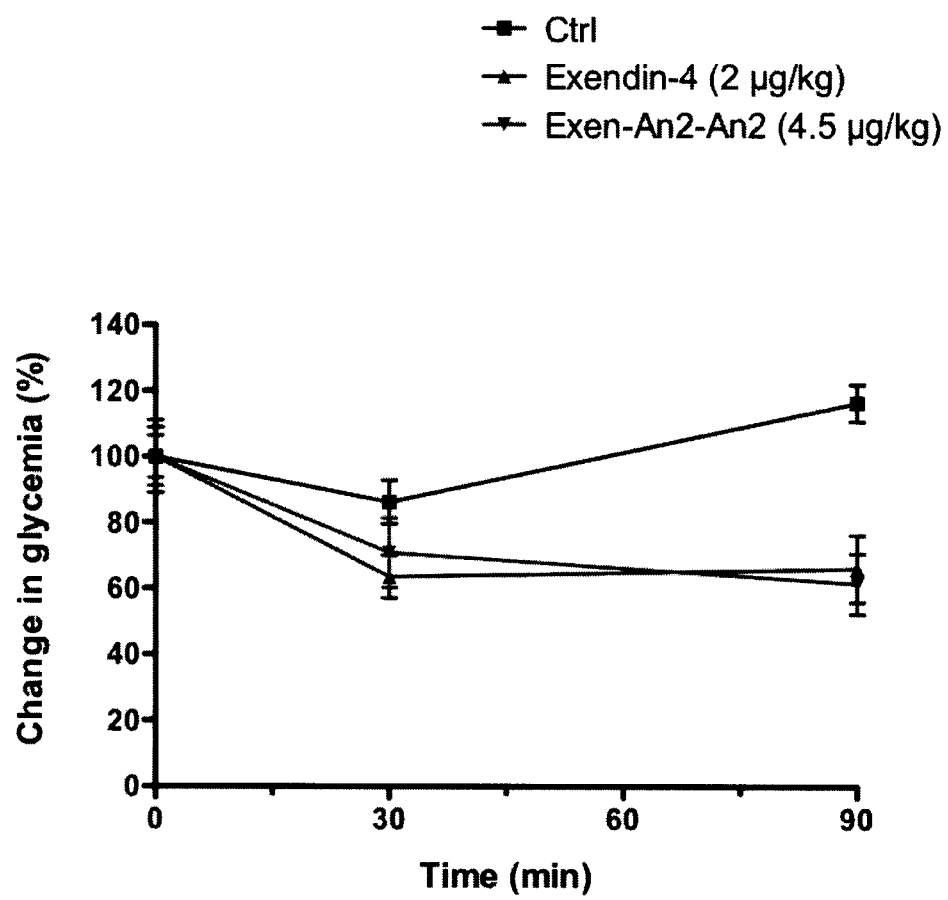
FIG. 10 is a graph showing the ability of Exendin-4 and Exen-An2-An2 to reduce glycemia in mice.

We also tested the ability of the exendin-4-Angiopep-2 dimer conjugate to reduce glycemia in DIO mice. Mice were injected with a bolus containing a control, exendin-4, or the exendin-4-Angiopep-2 dimer conjugate. Mice receiving either exendin-4 or the conjugate exhibited reduced glycemia as compared to mice receiving the control (FIG. 10).

EXAMPLE 6

Characterization of an Exendin-4-Angiopep-2 Dimer Conjugate

Brain uptake of the exemplary GLP-1 agonist, exendin-4, was measured in situ when unconjugated, conjugated to a single Angiopep-2, conjugated to S4, or conjugated to a dimeric form of Angiopep-2. The experiments were performed as described in Example 2 above.

From these results, we observed that conjugation of the exendin-4 analog to the dimeric form of Angiopep-2 results in a conjugate with a surprisingly greater ability to cross the BBB as compared to either the unconjugated exendin-4 or to the exendin-4 conjugated to a single Angiopep-2 (FIG. 8).

We also tested the ability of the exendin-4-Angiopep-2 dimer conjugate to reduce glycemia in DIO mice. Mice were injected with a bolus containing a control, exendin-4, or the exendin-4-Angiopep-2 dimer conjugate. Mice receiving either exendin-4 or the conjugate exhibited reduced glycemia as compared to mice receiving the control (FIG. 9).

Other Embodiments

All patents, patent applications, including U.S. Provisional application No. 61/105,618, filed Oct. 15, 2008, and publications mentioned in this specification are herein incorporated by reference to the same extent as if each independent patent, patent application, or publication was specifically and individually indicated to be incorporated by reference.

What is claimed is:

1. A compound having the structure:

123 124
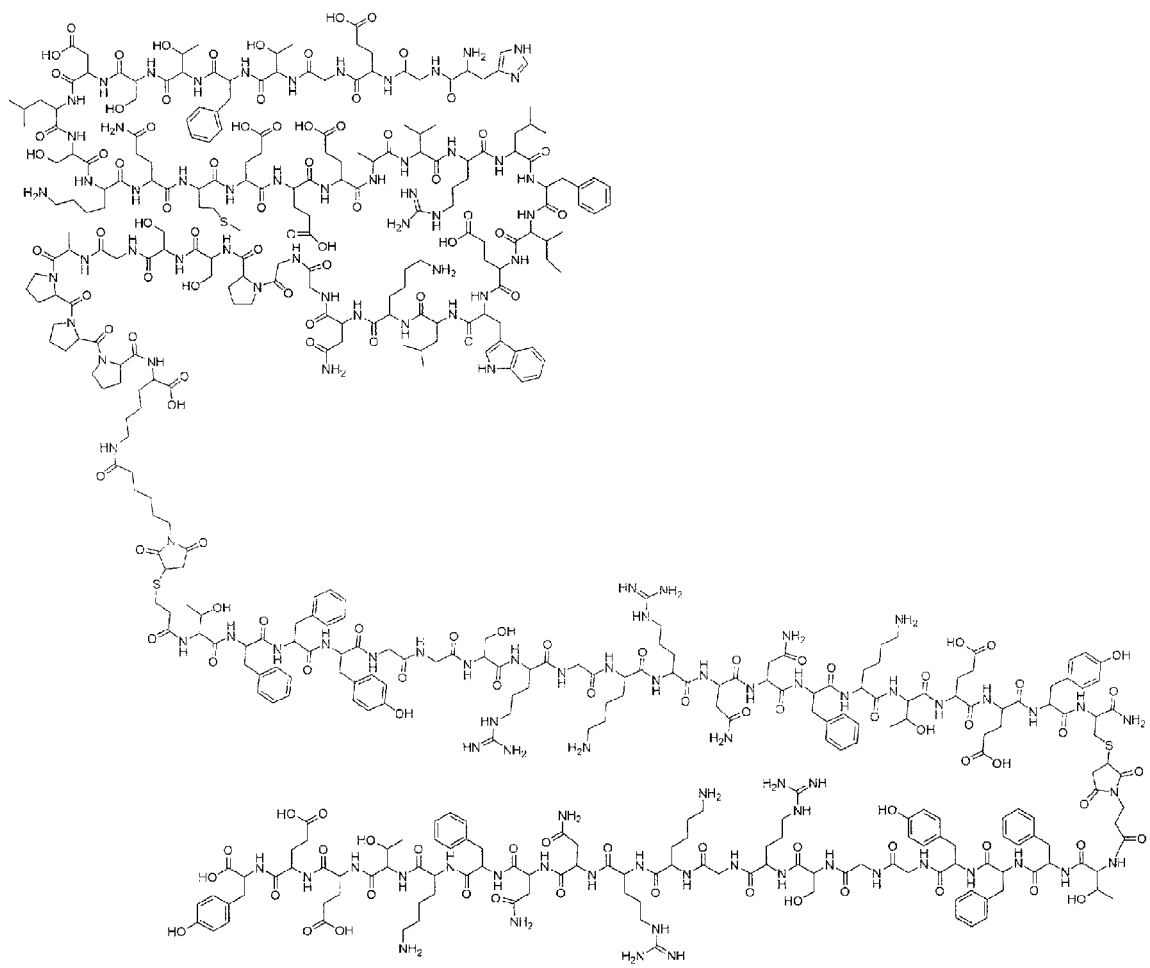

or a pharmaceutically acceptable salt thereof.

2. A method of making the compound of claim 1, said method comprising synthesizing said compound on solid support.

3. A method of treating a subject having a metabolic disorder, said method comprising administering the compound of claim 1 in an amount sufficient to treat said disorder, wherein said metabolic disorder is diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, or hyperlipidemia.

4. The method of claim 1, wherein said amount sufficient is less than 50% of the amount required for an equivalent dose of the GLP-1 agonist when not conjugated to the peptide vector.

5. The method of claim 1, wherein said disorder is diabetes, or obesity.

6. A method of reducing food intake by, or reducing body weight of, a subject, said method comprising administering the compound of claim 1 to a subject in an amount sufficient to reduce food intake or reduce body weight.

7. The method of claim 6, wherein said subject is overweight or obese.

8. A method of increasing GLP-1 receptor activity in a subject, said method comprising administering the compound of claim 1 to a subject in an amount sufficient to increase GLP-1 receptor activity.

* * * * *